(12) United States Patent
Jacques et al.

(10) Patent No.: US 10,029,988 B2
(45) Date of Patent: Jul. 24, 2018

(54) HDAC INHIBITORS

(71) Applicant: BIOMARIN PHARMACEUTICAL INC., Novato, CA (US)

(72) Inventors: Vincent Jacques, Somerville, MA (US); James R. Rusche, Framingham, MA (US)

(73) Assignee: BIOMARIN PHARMACEUTICAL INC., Novato, CA (US)

(*) Notice: Subject to any disclaimer, the term of this patent is extended or adjusted under 35 U.S.C. 154(b) by 0 days.

(21) Appl. No.: 14/773,472

(22) PCT Filed: Mar. 14, 2014

(86) PCT No.: PCT/US2014/027633
§ 371 (c)(1),
(2) Date: Sep. 8, 2015

(87) PCT Pub. No.: WO2014/143666
PCT Pub. Date: Sep. 18, 2014

(65) Prior Publication Data
US 2016/0031823 A1    Feb. 4, 2016

Related U.S. Application Data

(60) Provisional application No. 61/863,235, filed on Aug. 7, 2013, provisional application No. 61/800,170, filed on Mar. 15, 2013.

(51) Int. Cl.
*C07D 231/56* (2006.01)
*C07D 401/06* (2006.01)

(52) U.S. Cl.
CPC ......... *C07D 231/56* (2013.01); *C07D 401/06* (2013.01)

(58) Field of Classification Search
None
See application file for complete search history.

(56) References Cited

U.S. PATENT DOCUMENTS

| | | | |
|---|---|---|---|
| 4,174,958 A | 11/1979 | Pilgram | |
| 4,855,422 A | 8/1989 | Grimminger et al. | |
| 6,710,060 B2 | 3/2004 | Yamamoto et al. | |
| 8,329,946 B2 | 12/2012 | Schreiber et al. | |
| 8,957,066 B2 | 2/2015 | Jacques et al. | |
| 9,096,549 B2 * | 8/2015 | van Duzer ........... | C07D 235/06 |
| 2004/0029885 A1 | 2/2004 | Bauer et al. | |
| 2004/0106599 A1 | 6/2004 | Delorme et al. | |
| 2004/0142859 A1 | 7/2004 | Steffan et al. | |
| 2004/0142953 A1 | 7/2004 | Delorme et al. | |
| 2004/0147569 A1 | 7/2004 | Suzuki et al. | |
| 2004/0215601 A1 | 10/2004 | Liu et al. | |
| 2006/0166990 A1 | 7/2006 | Ottosen et al. | |
| 2007/0049603 A1 | 3/2007 | Miknis et al. | |
| 2009/0306077 A1 | 12/2009 | Mogi et al. | |
| 2010/0056522 A1 | 3/2010 | Yoneda et al. | |
| 2010/0063045 A1 | 3/2010 | Mogi et al. | |
| 2010/0196502 A1 | 8/2010 | Kozikowski et al. | |
| 2010/0298358 A1 | 11/2010 | Lu et al. | |
| 2012/0094971 A1 | 4/2012 | Rusche et al. | |
| 2013/0210899 A1 | 8/2013 | Wood | |
| 2013/0317003 A1 | 11/2013 | Jacques et al. | |

FOREIGN PATENT DOCUMENTS

| | | |
|---|---|---|
| CN | 1632700 A | 6/2005 |
| CN | 101648922 A | 2/2010 |
| EP | 1390491 A1 | 2/2004 |
| EP | 2125023 B2 | 10/2013 |
| JP | 11269140 | 10/1999 |
| JP | 11269146 | 10/1999 |
| JP | 11302173 | 11/1999 |
| JP | 2000256194 A | 9/2000 |
| JP | 2003137866 A | 5/2003 |
| JP | 2004035485 A | 2/2004 |
| JP | 2007001885 A | 1/2007 |
| KR | 2010117391 | 7/2012 |
| WO | WO-2000/035877 | 6/2000 |
| WO | WO-2001/038322 | 5/2001 |
| WO | WO-2002/018335 | 3/2002 |

(Continued)

OTHER PUBLICATIONS

Alberini, Transcription factors in long-term memory and synaptic plasticity. *Physiol. Rev.* 89(1): 121-45 (2009).
Andrews et al., Anti-malarial effect of histone deacetylation inhibitors and mammalian tumour cytodifferentiating agents. *Int. J. Parasitol.* 30(6): 761-8 (2000).
Andrews et al., Design and campaign synthesis of piperidine- and thiazole-based histone deacetylase inhibitors. *Bioorg. Med. Chem. Lett.* 18(8): 2580-4 (2008).
Andrews et al., Potent antimalarial activity of histone deacetylase inhibitor analogues. *Antimicrob. Agents Chemother.* 52(4): 1454-61.

(Continued)

*Primary Examiner* — Kamal Saeed
(74) *Attorney, Agent, or Firm* — Marshall, Gerstein & Borun LLP

(57) ABSTRACT

Disclosed herein are compounds of formula (I), and methods of inhibiting histone deacetylase ("HDAC") enzymes (e.g., HDAC1, HDAC2, and HDAC3) using compounds of formula (I).

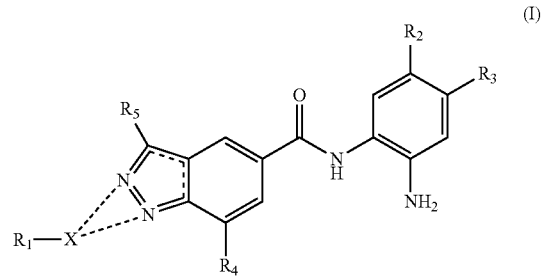

(I)

28 Claims, No Drawings

(56) References Cited

FOREIGN PATENT DOCUMENTS

| WO | WO-2002/090534 | | 11/2002 |
|---|---|---|---|
| WO | WO-2003/011851 | | 2/2003 |
| WO | WO-2003/013484 | | 2/2003 |
| WO | WO-2003/024448 | | 3/2003 |
| WO | WO-2003/076422 | | 9/2003 |
| WO | WO-2003/087057 | | 10/2003 |
| WO | WO-2003/092686 | | 11/2003 |
| WO | WO-2004/005513 | A2 | 1/2004 |
| WO | WO-2004/035525 | A1 | 4/2004 |
| WO | WO-2004/039318 | A2 | 5/2004 |
| WO | WO-2004/041273 | A1 | 5/2004 |
| WO | WO-2004/052838 | A1 | 6/2004 |
| WO | WO-2004/058234 | A2 | 7/2004 |
| WO | WO-2004/069133 | A2 | 8/2004 |
| WO | WO-2004/069823 | A1 | 8/2004 |
| WO | WO-2004/071400 | A2 | 8/2004 |
| WO | WO-2004/072068 | A1 | 8/2004 |
| WO | WO-2004/087693 | A1 | 10/2004 |
| WO | WO-2005/002552 | A2 | 1/2005 |
| WO | WO-2005/003127 | A1 | 1/2005 |
| WO | WO-2005/030144 | A2 | 4/2005 |
| WO | WO-2005/030704 | A1 | 4/2005 |
| WO | WO-2005/030705 | A1 | 4/2005 |
| WO | WO-2005/035551 | A2 | 4/2005 |
| WO | WO-2005/055928 | A2 | 6/2005 |
| WO | WO-2005/058803 | A1 | 6/2005 |
| WO | WO-2005/087724 | A2 | 9/2005 |
| WO | WO-2005/092899 | A1 | 10/2005 |
| WO | WO-2005/121073 | A1 | 12/2005 |
| WO | WO-2006/001958 | A2 | 1/2006 |
| WO | WO-2006/005955 | A1 | 1/2006 |
| WO | WO-2006/014618 | A2 | 2/2006 |
| WO | WO-2006/033943 | A2 | 3/2006 |
| WO | WO-2006/062580 | A1 | 6/2006 |
| WO | WO-2006/065703 | A1 | 6/2006 |
| WO | WO-2006/066133 | A2 | 6/2006 |
| WO | WO-2006/070192 | A1 | 7/2006 |
| WO | WO-2006/097474 | A1 | 9/2006 |
| WO | WO-2006/102760 | A1 | 10/2006 |
| WO | WO-2006/104983 | A1 | 10/2006 |
| WO | WO-2006/105979 | A1 | 10/2006 |
| WO | WO-2006/115845 | A1 | 11/2006 |
| WO | WO-2006/122319 | A1 | 11/2006 |
| WO | WO-2007/002248 | A2 | 1/2007 |
| WO | WO-2007/011626 | A2 | 1/2007 |
| WO | WO-2007/022638 | A1 | 3/2007 |
| WO | WO-2007/039403 | A1 | 4/2007 |
| WO | WO-2007/039404 | A1 | 4/2007 |
| WO | WO-2007/044565 | A2 | 4/2007 |
| WO | WO-2007/045844 | A1 | 4/2007 |
| WO | WO-2007/055942 | A2 | 5/2007 |
| WO | WO-2007/058927 | A1 | 5/2007 |
| WO | WO-2007/061880 | A1 | 5/2007 |
| WO | WO-2007/082873 | A1 | 7/2007 |
| WO | WO-2007/082874 | A1 | 7/2007 |
| WO | WO-2007/082876 | A1 | 7/2007 |
| WO | WO-2007/082878 | A1 | 7/2007 |
| WO | WO-2007/082882 | A1 | 7/2007 |
| WO | WO-2007/084390 | A2 | 7/2007 |
| WO | WO-2007/087129 | A2 | 8/2007 |
| WO | WO-2007/087130 | A2 | 8/2007 |
| WO | WO-2007/100657 | A2 | 9/2007 |
| WO | WO-2007/113289 | A1 | 10/2007 |
| WO | WO-2007/118137 | A1 | 10/2007 |
| WO | WO-2007/136605 | A2 | 11/2007 |
| WO | WO-2008/006793 | A1 | 1/2008 |
| WO | WO-2008/010985 | A1 | 1/2008 |
| WO | WO-2008/033743 | A1 | 3/2008 |
| WO | WO-2008/033747 | A2 | 3/2008 |
| WO | WO-2008/074132 | A1 | 6/2008 |
| WO | WO-2008/084218 | A1 | 7/2008 |
| WO | WO-2008/089436 | A2 | 7/2008 |
| WO | WO-2008/109994 | A1 | 9/2008 |
| WO | WO-2008/112913 | A1 | 9/2008 |
| WO | WO-2008/113255 | A1 | 9/2008 |
| WO | WO-2008122115 | A1 | 10/2008 |
| WO | WO-2009/002495 | A1 | 12/2008 |
| WO | WO-2009/002534 | A1 | 12/2008 |
| WO | WO-2009/004427 | A2 | 1/2009 |
| WO | WO-2009/015237 | A1 | 1/2009 |
| WO | WO-2009/020589 | A1 | 2/2009 |
| WO | WO-2009/024825 | A1 | 2/2009 |
| WO | WO-2009/025785 | A2 | 2/2009 |
| WO | WO-2009/027746 | A1 | 3/2009 |
| WO | WO-2009/033281 | A1 | 3/2009 |
| WO | WO-2009/036057 | A1 | 3/2009 |
| WO | WO-2009/037001 | A2 | 3/2009 |
| WO | WO-2009/045440 | A1 | 4/2009 |
| WO | WO-2009/053808 | A2 | 4/2009 |
| WO | WO-2009/063054 | A1 | 5/2009 |
| WO | WO-2009/079391 | A1 | 6/2009 |
| WO | WO-2009/086012 | A1 | 7/2009 |
| WO | WO-2009/112522 | A1 | 9/2009 |
| WO | WO-2009/156484 | A2 | 12/2009 |
| WO | WO-2010/009139 | A2 | 1/2010 |
| WO | WO-2010/009155 | A2 | 1/2010 |
| WO | WO-2010/009166 | A1 | 1/2010 |
| WO | WO-2010/014611 | A1 | 2/2010 |
| WO | WO-2010/028192 | A1 | 3/2010 |
| WO | WO-2010/028213 | A2 | 3/2010 |
| WO | WO-2010/031708 | A2 | 3/2010 |
| WO | WO-2010/038081 | A2 | 4/2010 |
| WO | WO-2010/043953 | A2 | 4/2010 |
| WO | WO-2010/049182 | A2 | 5/2010 |
| WO | WO-2010/094678 | A1 | 8/2010 |
| WO | WO-2010/126811 | A1 | 11/2010 |
| WO | WO-2010/126851 | A1 | 11/2010 |
| WO | WO-2010/127152 | A2 | 11/2010 |
| WO | WO-2010/131922 | A2 | 11/2010 |
| WO | WO-2010/144371 | A1 | 12/2010 |
| WO | WO-2010/144378 | A2 | 12/2010 |
| WO | WO-2012/016081 | A2 | 2/2012 |
| WO | WO-2012/118782 | A1 | 9/2012 |
| WO | WO-2013/113841 | A1 | 8/2013 |

OTHER PUBLICATIONS

Annemieke et al., Histone deacetylases (HDACs): characterization of the classical HDAC family. *Biochem J.* 370(Pt 3): 737-49 (2003).
Archin et al., Administration of vorinostat disrupts HIV-1 latency in patients on antiretroviral therapy. *Nature*, 487(7408): 482-5 (2012).
Ashton et al., New low-density lipoprotein receptor upregulators acting via a novel mechanism. *J Med. Chem.* 39(17): 3343-56 (1996).
Bayomi, Synthesis and ring transformation of pyrrolo[2,3-d][1,3]oxazine to pyrrolo[2,3-d]pyrimidines. *Arch. Pharm. Res.* 13(1): 97-100 (1990).
Bayomi, Synthesis and ring transformation of pyrrolo[2,3-d][1,3]oxazine to pyrrolo[2,3-d]pyrimidines. *Journal of the Chinese Chemical Society*, 39(1): 101-4 (1992).
Bioassay of 4-Chloro-o-phenylenediamine for possible carcinogenicity. National Cancer Institute Carcinogenesis Technical Report Series, 63: 1-50 (1978).
Blackwell et al., Effect of histone deacetylase inhibitors on HIV production in latently infected, resting CD4(+) Tcells from infected individuals receiving effective antiretroviral therapy. *J. Infect. Dis.* 206(5): 765-9 (2012).
Blazkova et al., Effect of histone deacetylase inhibitors on HIV production in latently infected, resting CD4(+) T cells from infected individuals receiving effective antiretroviral therapy. *J. Infect. Dis.* 206(5): 765-9 (2012).
Boev et al., Synthesis of new polydentate tweezers ligands of amido-amine type. *Russian Journal of Org. Chem.* 43(2): 297-304 (2007).
Campuzano et al., Friedreich's ataxia: autosomal recessive disease caused by an intronic GAA triplet repeat expansion. *Science*, 271(5254): 1423-7 (1996).
CAS Science IP, Search Report dated Dec. 17, 2010, 125 pages.
CAS Science IP, Search Report dated Dec. 17, 2010, 97 pages.
CAS Science IP, Search Report dated Dec. 20, 2010, 284 pages.

(56) References Cited

OTHER PUBLICATIONS

CAS Science IP, Search Report dated Dec. 20, 2010, 860 pages.
Charles et al., Synthesis of substituted benzamides and benzimidazoles as anthelmintic and antimicrobial agents. *Pharmazie*, 37(6): 413-15 (1982).
Charrier et al., Antiproliferative activities of a library of hybrids between indanones and HDAC inhibitor SAHA and MS-275 analogue. *Bioorg Med Chem Lett*. 17(22):6142-6 (2007).
Charton et al., Synthesis and biological evaluation of benzimidazole derivatives as potent AMP-activated protein kinase activators. *Bioorg Med Chem*. 14(13): 4490-518 (2006).
Chen et al., Discovering benzamide derivatives as glycogen phosphorylase inhibitors and their binding site at the enzyme. *Bioorg Med Chem*. 15(21): 6763-74 (2007).
Chen et al., Pyrrolopyridazine MEK inhibitors. *Bioorg Med Chem Lett*. 16(3): 628-32 (2006).
Chou et al., Pimelic diphenylamide 106 is a slow, tight-binding inhibitor of class I histone deacetylases. *J. Biol. Chem*. 283(51): 35402-9 (2008).
Coxon et al., Structure of the reaction product of 4-hydroxy-2,3-dioxo-4-phenylbutanoic acid 1,4-lactone with o-phenylenediamine. *Carbohydrate Res*. 142(1): 1-10 (1985).
Dahn et al., Reductones and tricarbonyl compds. XXI. Reactions of dehydroascorbic acid and of other 2,3-dioxobutyrolactones with o-phenylenediamine. *Helvetica Chimica Acta*. 47(7):1860-70 (1964).
Dessalew, QSAR study on aminophenylbenzamides and acrylamides as histone deacetylase inhibitors: an insight into the structural basis of antiproliferative activity. *Med Chem Res*. 16(7/9): 449-60 (2007).
Dokmanovic et al., Histone deacetylase inhibitors: overview and perspectives. *Mol. Cancer Res*. 5(10):981-9 (2007).
El Ashry et al., Reaction of dehydro-L-ascorbic acid analogs with o-phenylenediamine. *Carbohydrate Res*. 153(1): 146-9 (1986).
Examination Report issued in European Patent Application No. EP 12751918.9, dated Oct. 17, 2014.
Farag et al., Studies with polyfunctionally substituted heterocycles. Novel syntheses of pyrazolyl-1,2,4-triazoles and pyrazolo[5,1-c][1,2,4]triazines. *J. Chemical Res. Synopses*, (1):10-1 (1994).
Finnin et al., Structures of a histone deacetylase homologue bound to the TSA and SAHA inhibitors. *Nature*, 401(6749): 188-93 (1999).
Fournel et al., MGCD0103, a novel isotype-selective histone deacetylase inhibitor, has broad spectrum antitumor activity in vitro and in vivo. *Mol. Cancer Ther*. 7(4): 759-68 (2008).
Frechette et al., 4-(Heteroarylaminomethyl)-N-(2-aminophenyl)-benzamides and their analogs as a novel class of histone deacetylase inhibitors. *Bioorg Med Chem Lett*. 18(4):1502-6 (2008).
Gilley et al., 2-Nitrophenyl isocyanide as a versatile convertible isocyanide: rapid access to a fused γ lactam13-lactone bicycle. *J Org Chem*. 73(11): 4198-204 (2008).
Goebel et al., Characterization of new PPARγ agonists: analysis of telmisartan's structural components. *Chem. Med. Chem*. 4(3): 445-56 (2009).
Guan et al., HDAC2 negatively regulates memory formation and synaptic plasticity. *Nature*, 459(7243): 55-60 (2009).
Habib et al., Synthetic approaches and biological evaluation of some new sulfonate ester-containing quinazoline derivatives as potentially active antimicrobial agents. *Bollettino Chimico Farmaceutico*, 134(4): 209-15 (1995).
Hamblett et al., The discovery of 6-amino nicotinamides as potent and selective histone deacetylase inhibitors. *Bioorg Med Chem Lett*. 17(19): 5300-9 (2007).
Hasegawa et al., Novel naphthalene derivatives as inhibitors of human immunoglobulin e antibody production. *J Med Chem*. 40(4): 395-407 (1997).
Hassan et al., Condensed pyrroles: N1-benzyl-2,5,6-trimethylpyrrolo[2,3-d]-1,3-oxazin-4-ones and N1-benzyl -2,5,6-trimethyl-3-substituted-pyrrolo[2,3-d]pyrimidin-4-ones. *Indian Journal of Chemistry, Section B: Organic Chemistry Including Medicinal Chemistry*, 39B(10): 764-8 (2000).
Heidebrecht Jr et al., Exploring the pharmacokinetic properties of phosphorus-containing selective HDAC 1 and 2 inhibitors (SHI-1:2). *Bioorg. Med. Chem. Lett*. 19(7): 2053-8 (2009).
Herman et al., Histone deacetylase inhibitors reverse gene silencing in Friedreich's ataxia. *Nat. Chem. Bio*. 2(10): 551-8 (2006).
Huang et al., N-(2-Aminophenyl)-2-anilinobenzamide. *Acta Crystallographica*, 65(5): o1108-17 (2009).
Hubbs et al., Amino acid derivatives as histone deacetylase inhibitors. *Bioorg Med Chem Lett*. 18(1): 34-8 (2008).
International Preliminary Report on Patentability and Written Opinion; Patent Cooperation Treaty, PCT application No. PCT/US2009/055952; dated Mar. 8, 2011.
International Preliminary Report on Patentability in International Application No. PCT/US2012/26874; dated Sep. 3, 2013.
International Search Report and Written Opinion of the International Searching Authority in connection with International Application No. PCT/US2009/055952, United States Patent Office, dated Dec. 15, 2009.
International Search Report and Written Opinion of the International Searching Authority in connection with International Application No. PCT/US2012/26874, United States Patent Office, dated Jun. 13, 2012.
International Search Report and Written Opinion of the International Searching Authority in connection with International Application No. PCT/US2014/027347, United States Patent Office, dated Aug. 28, 2014.
International Search Report and Written Opinion of the International Searching Authority in connection with International Application No. PCT/US2014/027633, United States Patent Office, dated Mar. 14, 2014.
Ismail et al., Behavior of 2-substituted 6,8-dibromo-3,1-benzoxazin-4-ones towards o-phenylenediamine and anthranilic acid; a case of unusual cleavage of 6,8-dibromo-2-methyl-3,1-benzoxazin-4-one. *Tetrahedron*, 44(12): 3757-60 (1988).
Jazouli et al., a short and efficient synthesis of 2'-deoxybenzo- and pyridoimidazole C-nucleosides. *Tetrahedron Left*. 44(31): 5807-10 (2003).
Katayev et al., Anion binding by pyrrole-pyridine-based macrocyclic polyamides. *Supramolecular Chem*. 20(7): 619-24 (2008).
Katayev et al., Bipyrrole- and dipyrromethane-based amido-imine hybrid macrocycles. new receptors for oxoanions. *J. Org. Chem*. 72(8): 2886-96 (2007).
Katayev et al., Expanding sapphyrin: towards selective phosphate binding. *Chem Eur J*. 14(29): 9065-73 (2008).
Katritzky et al., Azlactones as Polymer Components and Intermediates. *J. Polymer Sci.: Part A: Polymer Chem*. 27: 1781-90 (1989).
Kattar et al., Parallel medicinal chemistry approaches to selective HDAC1/HDAC2 inhibitor (SHI-1:2) optimization. *Bioorg. Med. Chem. Lett*. 19(4): 1168-72 (2009).
Khan et al., Determination of the class and isoform selectivity of small-molecule histone deacetylase inhibitors. *Biochem. J*. 409(2): 581-9 (2008).
Kitagawa et al., Effects of a novel histone deacetylase inhibitor, N-(2-aminophenyl) benzamide, on a reversible hypertrophy induced by isoproterenol in in situ rat hearts. *J. Pharmacological Sci*. 104(2): 167-75 (2007).
Kiyokawa et al., New orally bioavailable 2-aminobenzamide-type histone deacetylase inhibitor possessing a (2-hydroxyethyl)(4-(thiophen-2-yl)benzyl)amino group. *Bioorg Med Chem*. 18(11): 3925-33 (2010).
Korshak et al., the effect of chemical defects in macromolecules on the thermal stability of pyrrones. *Academy of Sciences of the USSR*, 200: 865-8 (1971).
Kuroda et al., Further development of a robust workup process for solution-phase high-throughput library synthesis to address environmental and sample tracking issues. *Bioorg Med Chem*. 8(4): 505-12 (2006).
Li et al., Design, synthesis and bioevaluation of novel benzamides derivatives as HDAC inhibitors. *Bioorg. Med. Chem. Lett*. 23(1): 179-82 (2013).

(56) References Cited

OTHER PUBLICATIONS

Lu et al., Zn2+-chelating, motif-tethered, short-chain fatty acids as a novel class of histone deacetylase inhibitors. *J Med Chem.* 47(2): 467-74 (2004).

Mahboobi et al., Design of chimeric histone deacetylase- and tyrosine kinase-inhibitors: a series of imatinib hybrides as potent inhibitors of wild-type and mutant BCR-ABL, PDGF-Rb, and histone deacetylases. *J Med Chem.* 52(8): 2265-79 (2009).

Mai et al., Novel uracil-based 2-aminoanilide and 2-aminoanilide-like derivatives: Histone deacetylase inhibition and in-cell activities. *Bioorg. Med. Chem. Left.* 18(8): 2530-5 (2008).

Malvaez et al., HDAC3-selective inhibitor enhances extinction of cocaine-seeking behavior in a persistent manner. PNAS, 6 pages (2013).

McQuown et al., HDAC3 is a critical negative regulator of long-term memory formation. *J. Neurosci.* 31(2): 764-74 (2011).

Methot et al., Exploration of the internal cavity of histone deacetylase (HDAC) with selective HDAC1/HDAC2 inhibitors (SHI-1:2). *Bioorg Med Chem Left.* 18(3): 973-8 (2008).

Methot et al., SAR profiles of spirocyclic nicotinamide derived selective HDAC1/HDAC2 inhibitors (SHI-1:2). *Bioorg. Med. Chem. Left.* 18(23): 6104-9 (2008).

Moradei et al., Novel aminophenyl benzamide-type histone deacetylase inhibitors with enhanced potency and selectivity. *J Med Chem.* 50(23): 5543-6 (2007).

Moradei et al., Substituted N-(2-aminophenyl)-benzamides, (E)-N-(2-aminophenyl)-acrylamides and their analogues: Novel classes of histone deacetylase inhibitors. *Bioorg. Med. Chem. Left.* 16(15): 4048-52 (2006).

Nagaoka et al., Synthesis and cancer antiproliferative activity of new histone deacetylase inhibitors: hydrophilic hydroxamates and 2-aminobenzamide-containing derivatives. *European J. Med. Chem.* 41(6): 697-708 (2006).

o-Phenylenediamine [MAK Value Documentation, 1999]. *The MAK Collection for Occupational Health and Safety*, 216-235 (2012).

Oliva et al., Chromogenic charge transfer cleft-type tetrahydrobenzoxanthene enantioselective receptors for dinitrobenzoylamino acids. *J. Org. Chem.* 69(20): 6883-5 (2004).

Paquin et al., Design and synthesis of 4-[(s-triazin-2-ylamino)methyl]-N-(2-aminophenyl)benzamides and their analogs as a novel class of histone deacetylase inhibitors. *Bioorg. Med. Chem. Lett.* 18(3):1067-71 (2008).

Patnaik, A Comprehensive Guide to the Hazardous Properties of Chemical Substances. 3rd ed. 257-8 (2006).

Pigro et al., Readily available carbohydrate-derived imines and amides as chiral ligands for asymmetric catalysis. *Tetrahedron*, 58(27): 5459-66 (2002).

Rabilloud et al., Condensation reactions between o-phenylenediamine and 2-substituted 1,3-ibenzoxazin-4-ones. *Bulletin de la Societe Chimique de France*, (11-12, Pt. 2): 2682-6 (1975).

Raeppel et al., SAR and biological evaluation of analogues of a small molecule histone deacetylase inhibitor N-(2-aminophenyl)-44(4-(pyridin-3-yl)pyrimidin-2-ylamino)methyl)benzamide (MGCD0103). *Bioorg. Med. Chem. Left.* 19(3): 644-9 (2009).

Rai et al., HDAC inhibitors correct frataxin deficiency in a Friedreich ataxia mouse mode. *Plos ONE*, 3(4): 1-8 (2008).

Reddy et al., Synthesis of chiral benzimidazole-pyrrolidine derivatives and their application in organocatalytic aldol and Michael addition reactions. *Synthetic Communications*, 37(24):4289-99 (2007).

Sagara et al., Identification of a novel 4-aminomethylpiperidine class of M3 muscarinic receptor antagonists and structural insight into their M3 selectivity. *J. Med. Chem.* 49(19): 5653-63 (2006).

Salisbury et al., Optimization of activity-based probes for proteomic profiling of histone deacetylase complexes. *J. Am. Chem. Soc.* 130(7): 2184-94 (2008).

Saruta et al., Sarcoma produced by subdermal administration of metaphenylenediamine and metaphenylenediamine hydrochloride. *Kyushu J. Med. Sci.* 13: 175-9 (1962).

Savarino et al., 'Shock and kill' effects of class I-selective histone deacetylase inhibitors in combination with the glutathione synthesis inhibitor buthionine sulfoximine in cell line models for HIV-1 quiescence. *Retrovirology*, 6: 52-62 (2009).

Schroeder et al., a selective HDAC 1/2 inhibitor modulates chromatin and gene expression in brain and alters mouse behavior in two mood-related tests. *PLoS ONE*, 8(8): e71323 (2013).

Siliphaivanh et al., Design of novel histone deacetylase inhibitors. *Bioorg. Med. Chem. Left.* 17(16): 4619-24 (2007).

Sontag, Carcinogenicity of substituted-benzenediamines (phenylenediamines) in rats and mice Carcinogenicity of substituted-benzenediamines (phenylenediamines) in rats and mice. *J. Natl. Cancer Inst.* 66(3): 591-602 (1981).

Stefanko et al., Modulation of long-term memory for object recognition via HDAC inhibition. *Proc. Natl. Acad. Sci. USA*, 106(23): 9447-52 (2009).

Stubbs et al., Selective inhibition of HDAC1 and HDAC2 is a potential therapeutic option for B-ALL, *Clin. Cancer Res.* 21(10): 2348-58 (2010).

Supplementary European Search Report, Appl. No. 09812248.4 dated Aug. 20, 2012.

Thomas et al., The HDAC inhibitor 4b ameliorates the disease phenotype and transcriptional abnormalities in Huntington's disease transgenic mice. *Proc. Natl. Acad. Sci. USA*, 105(40): 15564-9 (2008).

Tsujimoto et al., Condensation of o-phenylenediamine with dehydro-L-ascorbic acid derivatives and analogs. *Carbohydrate Res.* 138(1): 148-52 (1985).

Turitsyna et al., Azomethine dyes. II. Indoaniline dyes, derivatives of 1-hydroxy-2-naphthanilide. *Zhurnal Obshchei Khimii*, 26: 2546-54 (1956). English Summary.

Vaisburg et al., N-(2-Amino-phenyl)-4-(heteroarylmethyl)-benzamides as new histone deacetylase inhibitors. *Bioorg. Med. Chem. Left.* 17(24): 6729-33 (2007).

Valente et al., Pyrrole-based hydroxamates and 2-ainoanilides: histone deacetylase inhibition and cellular activities. *Chem. Med. Chem.* 4(9): 1411-5 (2009).

Vannini et al., Substrate binding to histone deacetylases as shown by the crystal structure of the HDAC8-substrate complex. *EMBO Reports*, 8: 879-84 (2007).

Vattipalli et al., Synthesis and 13-adrenergic blocking activity of naphthyloxypropylamines. *Indian J Chem. Section B: Organic Chemistry Including Medicinal Chemistry*, 47B(10): 1587-90 (2008).

Wagner, 3-Alkyl-3-allyl-2,4-diketo-1,2,4,5-tetrahydro-3H-benzo-1,5-diazepines and their hydration products. *Roczniki Chemii*, 48(7-8): 1289-96 (1974).

Wang et al., Immunomodulatory effects of deacetylase inhibitors: therapeutic targeting of FOXP3+ regulatory T cells. *Nat. Rev. Drug. Disc.* 8(12): 969-81 (2009).

Wang et al., Monoacylation of unprotected symmetrical diamines with resin-bound benzoic acids. *Tetrahedron Lett.* 45(35): 6645-8 (2004).

Wang et al., N-Hydroxy-1,2-disubstituted-1H-benzimidazol-5-yl acrylamides as novel histone deacetylase inhibitors: Design, synthesis, SAR studies, and in vivo antitumor activity. *Bioorg Med. Chem. Left.* 19(5): 1403-18 (2009).

Wang et al., Screening on in vitro anti-tumor activities of novel synthetic compounds targeting histone deacetylase. *Jiefangjun Yaoxue Xuebao*, 25(6): 482-5 (English Abstract) (2009).

Weisburger et al., Testing of twenty-one environmental aromatic amines or derivatives for long-term toxicity or carcinogenicity. *J. Environ. Pathol. Toxicol.* 2(2): 325-56 (1978).

Wilen et al., Strategies in optical resolutions. *Tetrahedron*, 33(21): 2725-2736 (1977).

Witter et al., Optimization of biaryl selective HDAC1&2 inhibitors (Shi-1:2). *Bioorg Med Chem Left.* 18(2): 726-31 (2008).

Zhu et al., Investigation on the isoform selectivity of histone deacetylase inhibitors using chemical feature based pharmacophore and docking approaches. *European J Med Chem.* 45(5): 1777-91 (2010).

\* cited by examiner

HDAC INHIBITORS

CROSS REFERENCE TO RELATED APPLICATIONS

The benefit of U.S. Provisional Application No. 61/800,170, filed Mar. 15, 2013, and U.S. Provisional Application No. 61/863,235, filed Aug. 7, 2013, is claimed, the disclosures of which are each incorporated by reference in their entirety.

TECHNICAL FIELD

This disclosure is directed generally to compounds which can inhibit histone deacetylase ("HDAC") enzymes (e.g., HDAC1, HDAC2, and HDAC3).

BACKGROUND

To date, 18 HDACs have been identified in humans and there is increasing evidence that the 18 histone deacetylases (HDAC) in humans are not redundant in function. HDACs are classified into three main groups based on their homology to yeast proteins. Class I includes HDAC1, HDAC2, HDAC3, and HDAC8 and have homology to yeast RPD3. HDAC4, HDAC5, HDAC7, and HDAC9 belong to class IIa and have homology to yeast HDAC1. HDAC6 and HDAC10 contain two catalytic sites and are classified as class IIb, whereas HDAC11 has conserved residues in its catalytic center that are shared by both class I and class II deacetylases and is placed in class IV. These HDACs contain zinc in their catalytic site and are inhibited by compounds like trichostatin A (TSA) and vorinostat [suberoylanilide hydroxamic acid (SAHA)]. Class III HDACs are known as sirtuins. They have homology to yeast Sir2, require $NAD^+$ as cofactor, and do not contain zinc in the catalytic site. In general, HDAC inhibitors of zinc-dependent HDACs include a Zn-binding group, as well as a surface recognition domain.

HDACs are involved in the regulation of a number of cellular processes. Histone acetyltransferases (HATs) and HDACs acetylate and deacetylate lysine residues on the N termini of histone proteins thereby affecting transcriptional activity. They have also been shown to regulate post-translational acetylation of at least 50 non-histone proteins such as α-tubulin (see for example Kahn, N et al Biochem J 409 (2008) 581, Dokmanovic, M et al Mol Cancer Res 5 (2007) 981).

Altering gene expression through chromatin modification can be accomplished by inhibiting histone deacetylase (HDAC) enzymes. There is evidence that histone acetylation and deacetylation are mechanisms by which transcriptional regulation in a cell—a major event in cell differentiation, proliferation, and apoptosis—is achieved. It has been hypothesized that these effects occur through changes in the structure of chromatin by altering the affinity of histone proteins for coiled DNA in the nucleosome. Hypoacetylation of histone proteins is believed to increase the interaction of the histone with the DNA phosphate backbone. Tighter binding between the histone protein and DNA can render the DNA inaccessible to transcriptional regulatory elements and machinery. HDACs have been shown to catalyze the removal of acetyl groups from the ε-amino groups of lysine residues present within the N-terminal extension of core histones, thereby leading to hypoacetylation of the histones and blocking of the transcriptional machinery and regulatory elements.

Inhibition of HDAC, therefore can lead to histone deacetylase-mediated transcriptional derepression of tumor suppressor genes. For example, cells treated in culture with HDAC inhibitors have shown a consistent induction of the kinase inhibitor p21, which plays an important role in cell cycle arrest. HDAC inhibitors are thought to increase the rate of transcription of p21 by propagating the hyperacetylated state of histones in the region of the p21 gene, thereby making the gene accessible to transcriptional machinery. Further, non-histone proteins involved in the regulation of cell death and cell-cycle also undergo lysine acetylation and deacetylation by HDACs and histone acetyl transferase (HATs).

This evidence supports the use of HDAC inhibitors in treating various types of cancers. For example, vorinostat (suberoylanilide hydroxamic acid (SAHA)) has been approved by the FDA to treat cutaneous T-cell lymphoma and is being investigated for the treatment of solid and hematological tumors. Further, other HDAC inhibitors are in development for the treatment of acute myelogenous leukemia, Hodgkin's disease, myelodysplastic syndromes and solid tumor cancers. Selective HDAC 1/2 inhibitors may also be useful in treating B-cell acute lymphoblastic leukemia (B-ALL) (Stubbs, et al., Selective Inhibition of HDAC1 and HDAC2 is a Potential Therapeutic Option for B-ALL, Molecular Pharmacology, Drug Resistance: Poster II, Poster Board II-780 (Dec. 5, 2010) and Witter et al., Bioorg. Med. Chem. Lett., 18:726-731 (2008) and Fournel et al., Mol. Cancer Ther. 7(4):759-68 (2008)).

HDAC inhibitors have also been shown to inhibit pro-inflammatory cytokines, such as those involved in autoimmune and inflammatory disorders (e.g. TNF-α). For example, the HDAC inhibitor MS275 was shown to slow disease progression and joint destruction in collagen-induced arthritis in rat and mouse models. Other HDAC inhibitors have been shown to have efficacy in treating or ameliorating inflammatory disorders or conditions in in vivo models or tests for disorders such as Crohn's disease, colitis, and airway inflammation and hyper-responsiveness. HDAC inhibitors have also been shown to ameliorate spinal cord inflammation, demyelination, and neuronal and axonal loss in experimental autoimmune encephalomyelitis (see for example Wanf L. et al., Nat Rev Drug Disc, 8:969 (2009)).

Triplet repeat expansion in genomic DNA is associated with many neurological conditions (e.g., neurodegenerative and neuromuscular diseases) including myotonic dystrophy, spinal muscular atrophy, fragile X syndrome, Huntington's disease, spinocerebellar ataxias, amyotrophic lateral sclerosis, Kennedy's disease, spinal and bulbar muscular atrophy, Friedreich's ataxia and Alzheimer's disease. Triplet repeat expansion may cause disease by altering gene expression. For example, in Huntington's disease, spinocerebellar ataxias, fragile X syndrome, and myotonic dystrophy, expanded repeats lead to gene silencing. In Friedreich's ataxia, the DNA abnormality found in 98% of FRDA patients is an unstable hyper-expansion of a GAA triplet repeat in the first intron of the frataxin gene (see Campuzano et al., Science 271:1423 (1996)), which leads to frataxin insufficiency resulting in a progressive spinocerebellar neurodegeneration. Since they can affect transcription and potentially correct transcriptional dysregulation, HDAC inhibitors have been tested and have been shown to positively affect neurodegenerative diseases (see Herman D et al, Nat Chem Bio 2 551 (2006) for Friedreich's ataxia, Thomas E A et al, Proc Natl Acad Sci USA 105 15564 (2008) for Huntington's disease).

HDAC inhibitors may also play a role in cognition-related conditions and diseases. It has indeed become increasingly evident that transcription is likely a key element for long-term memory processes (Alberini C M, Physiol Rev 89 121 (2009)) thus highlighting another role for CNS-penetrant HDAC inhibitors. Although studies have shown that treatment with non-specific HDAC inhibitors such as sodium butyrate can lead to long-term memory formation (Stefanko D P et al, Proc Natl Acad Sci USA 106 9447 (2009)), little is known about the role of specific isoforms. A limited number of studies have shown that, within class I HDACs, main target of sodium butyrate, the prototypical inhibitor used in cognition studies, HDAC2 (Guan J-S et al, Nature 459 55 (2009)) and HDAC3 (McQuown S C et al, J Neurosci 31 764 (2011)) have been shown to regulate memory processes and as such are interesting targets for memory enhancement or extinction in memory-affecting conditions such as, but not limited to, Alzheimer's disease, post-traumatic stress disorder or drug addiction.

HDAC inhibitors, e.g., HDAC1 and/or HDAC 2 selective inhibitors, may also be useful to treat sickle cell disease (SCD) and β-thalassemia (bT). They may also be useful in treating mood disorders or brain disorders with altered chomatin-mediated neuroplasticity (Schoreder, et al., PLoS ONE 8(8): e71323 (2013)).

HDAC inhibitors may also be useful to treat infectious disease such as viral infections. For example, treatment of HIV infected cells with HDAC inhibitors and anti-retroviral drugs can eradicate virus from treated cells (Blazkova j et al J Infect Dis. 2012 Sep. 1; 206(5):765-9; Archin N M et al Nature 2012 Jul. 25, 487(7408):482-5).

SUMMARY

This disclosure features compounds having formula (I), or a pharmaceutically acceptable salt thereof:

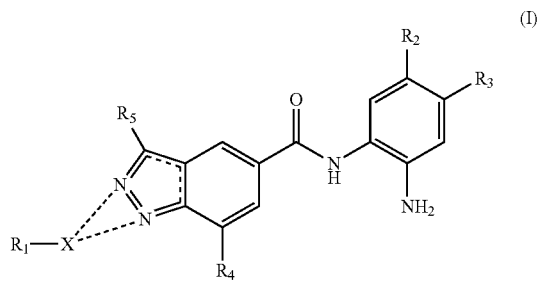

(I)

compositions (e.g., pharmaceutical compositions) containing the same and methods of using the same. For purposes of clarification, formula (I) encompasses both formulas (Ia) and (Ib) below:

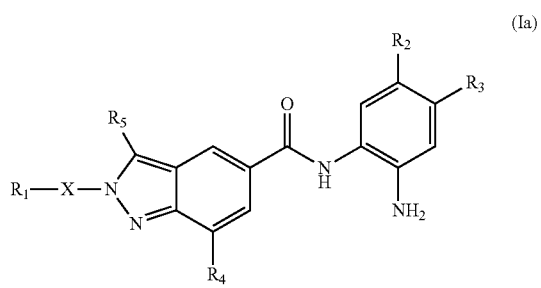

(Ia)

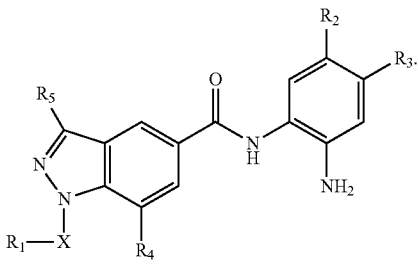

(Ib)

The formula (I) compounds described herein inhibit histone deacetylase ("HDAC") enzymes (e.g., HDAC1, HDAC2, and HDAC3). While not wishing to be bound by theory, it is believed that the ortho-amino ($NH_2$) benzamide portion of the formula (I) compounds interacts with (e.g., binds to) the zinc in zinc-dependent HDACs.

As the skilled artisan will appreciate, however, cleavage of the amide bond in the formula (I) compounds (e.g., during metabolism of the formula (I) compounds, often studied using in vitro metabolism of the formula (I) compounds in the presence of hepatocytes) can potentially lead to liberation of o-phenylenediamine (OPD). OPD is an organic compound having the chemical formula shown below.

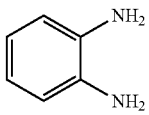

OPD is a known animal carcinogen and a suspected human carcinogen. It is mainly used as a chemical intermediate in the synthesis of dyes, pigments and fungicides. OPD is a relatively unstable molecule even in its solid state. OPD can cause acute poisoning in animals leading to tremors, convulsions, salivation and respiratory depression [1]. Although OPD is recognized as an animal carcinogen, studies to establish its relevance to humans, and effects of single and repeated OPD exposure in humans are inconclusive [2]. Adverse effects of OPD such as genotoxicity, reproductive toxicity, allergenic reactions and carcinogenicity are reported in several animal studies [1]. Sontag et al (1981) reported that a 78 week-long oral OPD administration lead to significant increase in liver tumors in male rats—5 out of 16 rats were found to be affected in a group administered with a 16000 mg/kg high dose of OPD, while 5 out of 17 were detected with tumors in a 8000 mg/kg low dose group [3, 4]. An article from NCI, described tumor formation on urinary bladder and fore stomach of both male and female rats, and hepatocellular carcinoma in both sexes of mice after dosing with OPD [5]. It also reports OPD as a definitive carcinogen in Fischer 344 rats and B6C3FI mice [5].

In contrast, studies by Saruta et al (1962) indicated no tumors were formed due to subcutaneous administration of OPD to rats. Groups of 5 rats were administered with a low dose of 45 mg/kg every second day for 11 months and a high dose of 90 mg/kg every second day for 5 months. Tumors were not detected in either of the groups [1, 6]. Nonetheless OPD is classified as a suspected human carcinogen by ACGIH in 1989 [2].

The inventors have found, however, that formula (I) compound metabolites are substantially free of OPD when formula (I) compounds are subjected to conditions intended to mimic in vivo metabolism pathways. As used herein, the term "substantially free of OPD" means that OPD was not detected by LC-MS/MS after (i) incubating a formula (I) compound with human, monkey, dog and rat hepatocytes and (ii) treating the metabolite milieu with an acidic solution of phenylglyoxal in an organic solvent (this addition leads to quantitative formation of 2-phenylquinoxaline, which can be easily quantified with a low lower limit of quantitation (LLOQ)). See the Examples section.

In some embodiments, the formula (I) compounds described herein exhibit additional attributes, e.g., valuable to development as pharmaceutically useful compounds by demonstrating relatively reduced plasma-protein binding (e.g., less than 99% binding, e.g., from 65% to 95% binding, e.g., from 75% to 95% binding, e.g., 75% binding). Accordingly, in one aspect, a compound having formula (I), or a pharmaceutically acceptable salt thereof, are featured:

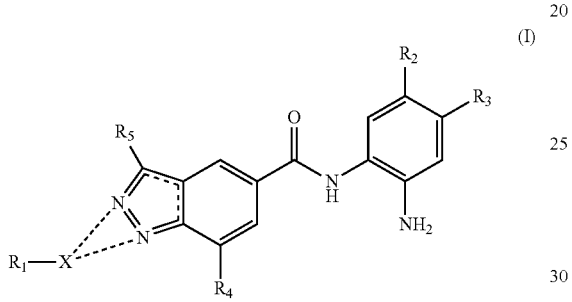

(I)

in which:
$R_1$—X is attached to only one of the ring nitrogen atoms;
X is:
(i) —Y—[C($R^a$)$_2$]$_a$-A-[C($R^b$)$_2$]$_b$—B—;
(ii) direct bond; or
(iii) C=O, C($R^j$)$_2$—C(=O), C(=O)—C($R^j$)$_2$, SO$_2$—N$R^k$, N$R^k$—SO$_2$, C(=O)N$R^k$ or N$R^k$—C(=O);
wherein:
Y is bond, C$R^c$=C$R^d$, O, N$R^e$, or S(O)$_m$;
each of A and B is, independently, a bond, O, N$R^f$, or S(O)$_m$;
a is 1, 2, or 3;
b is 0, 1, 2, or 3;
m is 0, 1, or 2;
each occurrence of $R^a$ and $R^b$ is independently selected from H, F, OH, C1-C6 alkyl, C3-C6 cycloalkyl, NH$_2$, OCO—(C1-C6 alkyl), OCO—(C3-C6 cycloalkyl), C1-C6 alkoxy, C1-C6 fluoroalkoxy, and cyano; or
one or more of the following can apply with respect to $R^a$ and $R^b$:
any two $R^a$, together with the carbons to which each is attached, together form C3-C6 cycloalkyl or heterocyclyl including 3-6 ring atoms, in which one of the heterocyclyl ring atoms is selected from O, S(O)$_m$ and N$R^g$; or
one $R^a$ and one $R^b$, together with the carbons to which each is attached, form C3-C6 cycloalkyl or heterocyclyl including 3-6 ring atoms, in which one of the heterocyclyl ring atoms is selected from O; S(O)m and N$R^g$; or
any two $R^b$, together with the carbons to which each is attached, form C3-C6 cycloalkyl or heterocyclyl including 3-6 ring atoms, in which one of the ring atoms is selected from O; S(O)m and N$R^g$;

each of $R^c$ and $R^d$ is independently selected from H, F, OH, C1-C6 alkyl, C3-C5 cycloalkyl, NH$_2$, OCO—(C1-C6 alkyl), OCO—(C3-C5 cycloalkyl), C1-C6 alkoxy, C1-C6 fluoroalkoxy, and cyano;
or $R^c$ and $R^d$, together with the carbons to which each is attached form a C5-C7 cycloalkyl or heterocyclyl including 3-6 ring atoms, in which from 1-2 of the heterocyclyl ring atoms are independently selected from O, S(O)$_m$ and N$R^g$;
each occurrence of $R^e$, $R^f$, $R^g$ and $R^{g'}$ is independently selected from H, C1-C6 alkyl, —C(=O)H, —C(=O)$R^h$, C(=O)O(C1-C6 alkyl), C(=O)N($R^i$)$_2$, and SO$_2$—$R^h$; wherein $R^h$ is selected from C1-C6 alkyl, CH$_2$-(heteroaryl including 5-10 ring atoms), CH$_2$—(C6-C10 aryl), and C6-C10 aryl; and each occurrence of $R^i$ is independently selected from H, C1-C6 alkyl, CH$_2$-(heteroaryl including 5-10 ring atoms), CH$_2$—(C6-C10 aryl), and C6-C10 aryl;
each occurrence of $R^j$ is independently selected from H, F, OH, C1-C6 alkyl, C3-C6 cycloalkyl, NH$_2$, OCO—(C1-C6 alkyl), OCO—(C3-C6 cycloalkyl), C1-C6 alkoxy, C1-C6 fluoroalkoxy, and cyano;
or $R^j$—C—$R^j$ together form C3-C6 cycloalkyl or heterocyclyl including 3-6 ring atoms, in which one of the heterocyclyl ring atoms is selected from O; S(O)m and N$R^{j'}$;
each occurrence of $R^{j'}$ and $R^k$ is independently selected from H, C1-C6 alkyl, —C(=O)H, —C(=O)$R^m$, C(=O)O(C1-C6 alkyl), C(=O)N($R^n$)$_2$, and SO$_2$—$R^m$, wherein $R^m$ is selected from C1-C6 alkyl, CH$_2$-(heteroaryl including 5-10 ring atoms), CH$_2$—(C6-C10 aryl), and C6-C10 aryl; and each occurrence of $R^n$ is independently selected from H, C1-C6 alkyl, CH$_2$-(heteroaryl including 5-10 ring atoms), CH$_2$—(C6-C10 aryl), and C6-C10 aryl, and wherein the aryl and heteroaryl portion in $R^m$ and $R^n$ can be optionally substituted with 1-3 independently selected substituents F, C1-C6 alkyl, fluoro C1-C6 alkyl, C3-C6 cycloalkyl, C1-C6 alkoxy, C1-C6 fluoroalkoxy, or cyano;
further wherein:
(a) when each of A and B is a bond, and b is 0, then X has the following formula: —Y—[C($R^a$)$_2$]$_a$—;
(b) when b is 0 or 1, then A and B cannot both be heteroatoms; and
(c) when A or B serves as the point of connection of X to the nitrogen ring atoms, then A or B cannot be a heteroatom;
R1 is:
(i) monocyclic or bicyclic heteroaryl including from 5-10 ring atoms, which is optionally substituted with from 1-3 $R^o$; wherein from 1-4 of the ring atoms are a heteroatom independently selected from O, N, N—H, N—$R^o$, and S;
(ii) C6-C10 aryl, which is optionally substituted with from 1-3 $R^o$; or
(iii) C3-C10 cycloalkyl or C3-C10 cycloalkenyl, each of which is optionally substituted with from 1-6 $R^o$;
(iv) heterocyclyl including from 3-10 ring atoms, which is optionally substituted with from 1-6 $R^o$; wherein from 1-4 of the ring atoms are a heteroatom independently selected from O, N, N—H, N—$R^o$, and S;

(v) hydrogen;
R4 is H or R° and each occurrence of R° is independently selected from the group consisting of: halogen; C1-C6 alkyl; fluoro(C1-C6)alkyl; hydroxyl; hydroxy($C_1$-$C_4$) alkyl; C1-C6 alkoxy; fluoro(C1-C6)alkoxy; (C1-C6 alkyl)C(O)—; (C1-C6 alkyl)NH—; (C1-C6 alkyl)$_2$N—; —N*(R°')$_2$, wherein R°'—N*—R°' together form a saturated ring having 5 or 6 ring atoms, in which 1 or 2 ring atoms are optionally a heteroatom independently selected from NH, N(C1-C6 alkyl), O, or S; formyl; formyl($C_1$-$C_4$) alkyl; cyano; cyano($C_1$-$C_4$) alkyl; benzyl; benzyloxy; (heterocyclyl)-(C0-C6) alkyl, wherein the heterocyclyl portion includes 5 or 6 ring atoms, in which 1 or 2 of the ring atoms are a heteroatom independently selected from NH, N(alkyl), O, or S, and when said alkyl portion is present, said alkyl portion serves as the point of attachment to R, and when the alkyl portion is not present, a heterocyclyl carbon ring atom serves as the point of attachment of the heterocyclyl to R1; phenyl; heteroaryl including from 5-6 ring atoms, wherein from 1-4 of the ring atoms are a heteroatom independently selected from O, N, N—H, N—R°", and S, each of which is optionally substituted with from 1-3 R°"; SO$_2$—(C1-C6)alkyl; SO—(C1-C6)alkyl; and nitro;
  each occurrence of R°" is independently selected from the group consisting of: halogen; C1-C6 alkyl; fluoro(C1-C6)alkyl; hydroxyl; hydroxy($C_1$-$C_4$)alkyl; C1-C6 alkoxy; fluoro(C1-C6)alkoxy; (C1-C6 alkyl)C(O)—; (C1-C6 alkyl)NH—; (C1-C6 alkyl)$_2$N—; formyl; formyl($C_1$-$C_4$) alkyl; cyano; cyano($C_1$-$C_4$) alkyl; benzyl; benzyloxy; (heterocyclyl)-(C0-C6) alkyl, wherein the heterocyclyl portion includes 5 or 6 ring atoms, in which 1 or 2 of the ring atoms are a heteroatom independently selected from NH, N(C1-C6alkyl), O, or S, and when said alkyl portion is present, said alkyl portion serves as the point of attachment to R1; and when the alkyl portion is not present, a heterocyclyl carbon ring atom serves as the point of attachment of the heterocyclyl to R1; phenyl; heteroaryl including from 5-6 ring atoms, wherein from 1-4 of the ring atoms are a heteroatom independently selected from O, N, N—H, N—(C1-C6 alkyl), and S; SO$_2$—(C1-C6)alkyl; SO—(C1-C6)alkyl; and nitro;
R5 is selected from the group consisting of: hydrogen, halogen; C1-C6 alkyl; fluoro(C1-C6)alkyl; hydroxyl; hydroxy($C_1$-$C_4$)alkyl; (C1-C6 alkyl)C(O)—; formyl; formyl($C_1$-$C_4$) alkyl; cyano; cyano($C_1$-$C_4$) alkyl; benzyl; (heterocyclyl)-(C0-C6)alkyl, wherein the heterocyclyl portion includes 5 or 6 ring atoms, in which 1 or 2 of the ring atoms are a heteroatom independently selected from NH, N(C1-C6alkyl), O, or S, and when said alkyl portion is present, said alkyl portion serves as the point of attachment to R1; and when the alkyl portion is not present, a heterocyclyl carbon ring atom serves as the point of attachment of the heterocyclyl to R1; phenyl; heteroaryl including from 5-6 ring atoms, wherein from 1-4 of the ring atoms are a heteroatom independently selected from O, N, N—H, N—$R^{q''}$, and S, each of which is optionally substituted with from 1-3 $R^{q''}$; SO$_2$—(C1-C6)alkyl; SO—(C1-C6)alkyl; and nitro;
R2 is selected from H, F, Cl, CF$_3$, CF$_2$CF$_3$, CH$_2$CF$_3$, OCF$_3$, OCHF$_2$, phenyl; or phenyl substituted with 1-3 R°; and
R3 is H, F, or Cl.

In another aspect, a compound of the formula (Ia) is featured.

In another aspect, a compound of the formula (Ib) is featured.

In a further aspect, the formula (I) compounds specifically described herein (or a salt, e.g., a pharmaceutically acceptable salt thereof) are featured (e.g., compounds A1-A24, or A1-A15, e.g., A1, A2, A3, A4, A5, A6, A7, A11, A12, A13, A14, A15, A16, A17, A18, A19, A20, A21, A22, A23, or A24).

In one aspect, a composition (e.g., a pharmaceutical composition) is featured, which includes a compound of formula (I) or a salt (e.g., a pharmaceutically acceptable salt) thereof as defined anywhere herein and a pharmaceutically acceptable carrier. In some embodiments, the composition can include an effective amount of the compound or its pharmaceutically acceptable salt. In some embodiments, the composition can further include an additional therapeutic agent.

In another aspect, a dosage form is featured, which includes from about 0.05 milligrams to about 2,000 milligrams (e.g., from about 0.1 milligrams to about 1,000 milligrams, from about 0.1 milligrams to about 500 milligrams, from about 0.1 milligrams to about 250 milligrams, from about 0.1 milligrams to about 100 milligrams, from about 0.1 milligrams to about 50 milligrams, or from about 0.1 milligrams to about 25 milligrams) of a compound of formula (I) or a salt (e.g., a pharmaceutically acceptable salt) thereof as defined anywhere herein. The dosage form can further include a pharmaceutically acceptable carrier and/or an additional therapeutic agent.

Provided herein are methods for inhibiting one (or more) HDACs (e.g., HDAC1 or HDAC2; e.g., HDAC3) or more than one HDAC (e.g., HDAC1 and HDAC2; e.g., HDAC1 and HDAC3; e.g., HDAC2 or HDAC3; e.g., HDAC1, HDAC2, and HDAC3) with a compound of formula (I) or a salt (e.g., a pharmaceutically acceptable salt) thereof as defined anywhere herein. In some embodiments, the methods can include, e.g., contacting one (or more) HDACs (e.g., HDAC1 or HDAC2; e.g., HDAC3) in a sample (e.g., a cell or tissue) with a compound of formula (I) or a salt (e.g., a pharmaceutically acceptable salt) thereof as defined anywhere herein. In other embodiments, the methods can include administering a compound of formula (I) or a salt (e.g., a pharmaceutically acceptable salt) thereof as defined anywhere herein to a subject (e.g., a mammal, such as a human). Accordingly, in yet another aspect, provided are methods of screening for compounds that inhibit (e.g., selectively inhibit) one or more HDACs (e.g., HDAC1 or HDAC2; e.g., HDAC3, e.g., HDAC1 and HDAC2; e.g., HDAC1 and HDAC3; e.g., HDAC2 or HDAC3; e.g., HDAC1, HDAC2, and HDAC3).

In one aspect, a method of selectively inhibiting HDAC3 is featured, which includes contacting an HDAC3 in a sample (e.g., a cell or tissue) with a compound of formula (I) or a salt (e.g., a pharmaceutically acceptable salt) thereof as defined anywhere herein; or administering a compound of formula (I) or a salt (e.g., a pharmaceutically acceptable salt) thereof as defined anywhere herein to a subject (e.g., a mammal, such as a human).

In one aspect, a method of selectively inhibiting HDAC1 or HDAC2 (e.g., HDAC1) is featured, which includes contacting HDAC1 or HDAC2 (e.g., HDAC1) in a sample (e.g., a cell or tissue) with a compound of formula (I) or a salt (e.g., a pharmaceutically acceptable salt) thereof as defined anywhere herein; or administering a compound of formula (I) or a salt (e.g., a pharmaceutically acceptable salt) thereof as defined anywhere herein to a subject (e.g., a mammal, such as a human).

In one aspect, a method of selectively inhibiting HDAC1, HDAC2, and HDAC3 is featured, which includes contacting HDAC1, HDAC2, and HDAC3 in one or more samples (e.g., a cell or tissue) with a compound of formula (I) or a salt (e.g., a pharmaceutically acceptable salt) thereof as defined anywhere herein; or administering a compound of formula (I) or a salt (e.g., a pharmaceutically acceptable salt) thereof as defined anywhere herein to a subject (e.g., a mammal, such as a human).

In one aspect, methods of treating (e.g., controlling, relieving, ameliorating, alleviating, or slowing the progression of) or methods for preventing (e.g., delaying the onset of or reducing the risk of developing) a disease or disorder mediated by HDAC1 or HDAC2 in a subject (e.g., a mammal, such as a human) in need thereof are featured, which include administering a compound of formula (I) or a salt (e.g., a pharmaceutically acceptable salt) thereof as defined anywhere herein to the subject.

In one aspect, methods of treating (e.g., controlling, relieving, ameliorating, alleviating, or slowing the progression of) or methods for preventing (e.g., delaying the onset of or reducing the risk of developing) a disease or disorder mediated by HDAC3 in a subject (e.g., a mammal, such as a human) in need thereof are featured, which include administering a compound of formula (I) or a salt (e.g., a pharmaceutically acceptable salt) thereof as defined anywhere herein to the subject.

In one aspect, methods of treating (e.g., controlling, relieving, ameliorating, alleviating, or slowing the progression of) or methods for preventing (e.g., delaying the onset of or reducing the risk of developing) a disease or disorder mediated by two or more HDACs (e.g., HDAC1 and HDAC2; e.g., HDAC1 and HDAC3; e.g., HDAC2 or HDAC3; e.g., HDAC1, HDAC2, and HDAC 3) in a subject (e.g., a mammal, such as a human) in need thereof are featured, which include administering a compound of formula (I) or a salt (e.g., a pharmaceutically acceptable salt) thereof as defined anywhere herein to the subject.

In one aspect, featured are methods of treating (e.g., controlling, relieving, ameliorating, alleviating, or slowing the progression of) or methods for preventing (e.g., delaying the onset of or reducing the risk of developing) a neurological disorder such as Friedreich's ataxia, myotonic dystrophy, spinal muscular atrophy, fragile X syndrome, Huntington's disease, spinocerebellar ataxia, Kennedy's disease, amyotrophic lateral sclerosis, spinal and bulbar muscular atrophy, and Alzheimer's disease; a cancer (e.g. cutaneous T cell lymphoma, B cell lymphomas, and colorectal cancer, and B-cell acute lymphoblastic leukemia); an inflammatory disease (e.g.,psoriasis, rheumatoid arthritis, and osteoarthritis); a memory impairment condition; mood disorder, brain disorder associated with chromatin-mediated neuroplasticity, post-traumatic stress disorder; a drug addiction; sickle cell anemia, β-thalassemia (bT), a *Plasmodium falciparum* infection (e.g., malaria) as well as other parasite infections in a subject (e.g., a mammal, such as a human) in need thereof, which include administering a compound of formula (I) or a salt (e.g., a pharmaceutically acceptable salt) thereof as defined anywhere herein to the subject.

In one aspect, a compound of formula (I) or a salt (e.g., a pharmaceutically acceptable salt) thereof as defined anywhere herein for use in medicine is featured.

In one aspect, featured is a compound of formula (I) or a salt (e.g., a pharmaceutically acceptable salt) thereof as defined anywhere herein for the treatment of: a disease or disorder mediated by HDAC1 or HDAC2; a disease or disorder mediated by HDAC3; a disease or disorder mediated by HDAC3 and HDAC1 or HDAC2; a disease or disorder mediated by HDAC1 and HDAC2 and HDAC3; a neurological disorder such as Friedreich's ataxia, myotonic dystrophy, spinal muscular atrophy, fragile X syndrome, Huntington's disease, spinocerebellar ataxia, Kennedy's disease, amyotrophic lateral sclerosis, Niemann Pick disease, Pitt Hopkins disease, spinal and bulbar muscular atrophy, and Alzheimer's disease; a cancer (e.g. cutaneous T cell lymphoma, B cell lymphomas, and colorectal cancer); an inflammatory disease (e.g., psoriasis, rheumatoid arthritis, and osteoarthritis); a memory impairment condition; post-traumatic stress disorder; a drug addiction; an infectious disease such as HIV; a *Plasmodium falciparum* infection (e.g., malaria) as well as other parasite infections, B-ALL, bT, sickle cell anemia, mood disorders, or brain disorders associated with chromatin-mediated neuroplasticity.

In one aspect, featured is a use of a compound of formula (I) or a salt (e.g., a pharmaceutically acceptable salt) thereof as defined anywhere herein, in the preparation of a medicament for the treatment of: a disease or disorder mediated by HDAC1 or HDAC2; a disease or disorder mediated by HDAC3; a disease or disorder mediated by HDAC3 and HDAC1 or HDAC2; a disease or disorder mediated by HDAC1 and HDAC2 and HDAC3; a neurological disorder such as Friedreich's ataxia, myotonic dystrophy, spinal muscular atrophy, fragile X syndrome, Huntington's disease, spinocerebellar ataxia, Kennedy's disease, amyotrophic lateral sclerosis, Niemann Pick, Pitt Hopkins disease, spinal and bulbar muscular atrophy, and Alzheimer's disease; a cancer (e.g. cutaneous T cell lymphoma, B cell lymphomas, B-ALL, and colorectal cancer); an inflammatory disease (e.g., psoriasis, rheumatoid arthritis, and osteoarthritis); a memory impairment condition; mood disorder, brain disorders with altered chomatin-mediated neuroplasticity, sickle cell anemia, β-thalassemia, post-traumatic stress disorder; a drug addiction; an infectious disease such as HIV; a *Plasmodium falciparum* infection (e.g., malaria) as well as other parasite infections.

In some embodiments, the subject can be a subject in need thereof (e.g., a subject identified as being in need of such treatment, such as a subject having, or at risk of having, one or more of the diseases or conditions described herein). Identifying a subject in need of such treatment can be in the judgment of a subject or a health care professional and can be subjective (e.g. opinion) or objective (e.g. measurable by a test or diagnostic method). In some embodiments, the subject can be a mammal. In certain embodiments, the subject can be a human.

In one aspect, methods of making compounds described herein are featured. In embodiments, the methods include taking any one of the intermediate compounds described herein and reacting it with one or more chemical reagents in one or more steps to produce a compound of formula (I) or a salt (e.g., a pharmaceutically acceptable salt) thereof as defined anywhere herein.

Some of the formula (I) compounds described herein have enhanced (e.g., increased, e.g., increased by a factor of about 2 or more, e.g., compared to other o-aminoanilide HDAC inhibitors) stabilities in acid. In some embodiments, the formula (I) compounds have enhanced resistances to degradation, e.g., less than about 25% degradation (e.g., less than about 20% degradation, less than about 15% degradation, or less than about 10% degradation) when exposed to acidic pH, e.g., acidic conditions intended to mimic those in the stomach, e.g., incubation (e.g., as a 10 μM solution) at 50° C. and at a pH of about 2.0 for about four hours. The resistance of compounds to degradation or metabolism at acidic pH can be a useful feature for a pharmaceutical agent (e.g., a drug). Increased stability at low pH can allow, for example, process preparation steps, such as salt formation, to occur without significant degradation of the desired salt. In addition, it is preferable that orally administered pharmaceuticals are stable to the acidic pH of the stomach. In some embodiments, compounds display enhanced stability when exposed to acidic pH with stability half-lives greater than e.g. 12 h or e.g. 18 h or e.g. 24 h at pH 2 and 50° C.

In some embodiments, the formula (I) compounds described herein selectively inhibit HDAC3, e.g., selectively inhibit HDAC3 over HDAC1 and HDAC2 (e.g. exhibiting 5-fold or greater selectivity, e.g. exhibiting 25-fold or greater selectivity). While not wishing to be bound by theory, it is believed that HDAC3-selective inhibitors can increase expression of frataxin, and could therefore be useful in the treatment of neurological conditions (e.g., neurological conditions associated with reduced frataxin expression, such as Friedreich's ataxia). It is also believed that HDAC3 inhibition plays an important role in memory consolidation (McQuown S C et al., J Neurosci, 31:764 (2011)). Selective inhibitors of HDAC3 could provide advantages for treatment of neurological conditions over the use of broad-spectrum HDAC inhibitors by reducing toxicities associated with inhibition of other HDACs. Such specific HDAC3 inhibitors would provide a higher therapeutic index, resulting in better tolerance by patients during chronic or long-term treatment.

In some further embodiments, compounds selectively inhibit HDAC 1 and/or HDAC2 (e.g., exhibiting 5-fold or greater selectivity, e.g. exhibiting 25-fold or greater selectivity).

In some embodiments, the formula (I) compounds described herein inhibit HDAC1, HDAC2, and HDAC3. While not wishing to be bound by theory, it is believed that HDAC3-selective inhibitors can increase expression of frataxin, and could therefore be useful in the treatment of neurological conditions (e.g., neurological conditions associated with reduced frataxin expression, such as Friedreich's ataxia).

In some embodiments, the formula (I) compounds described herein have been shown to inhibit class I histone deacetylases and this inhibition has resulted in an in vitro increased frataxin mRNA expression in Friedreich's ataxia patient peripheral blood mononuclear cells (PBMCs) and in neurons derived from induced pluripotent stem cells generated from Friedreich's ataxia patient cell line.

In some aspects, compounds disclosed herein inhibit in vitro proliferation of colorectal cancer cells in a dose-dependent fashion. In further embodiments, compounds disclosed herein which are specific for HDAC3 inhibition and show distribution to the CNS are expected to increase long term memory in vivo using the novel object recognition paradigm.

In some embodiments, the formula (I) compounds described herein exhibit enhanced brain penetration. For example, brain/plasma ratios of greater than about 0.25 (e.g., greater than about 0.50, greater than about 1.0, greater than about 1.5, or greater than about 2.0) are observed when mice are dosed with some of the formula (I) compounds described herein. Such compounds are therefore expected to be particularly suitable for therapies targeting the brain (e.g., neurological conditions such as Friedreich's ataxia, myotonic dystrophy, spinal muscular atrophy, fragile X syndrome, Huntington's disease, Niemann Pick, Pitt Hopkins, spinocerebellar ataxia, Kennedy's disease, amyotrophic lateral sclerosis, spinal and bulbar muscular atrophy, and Alzheimer's disease; a memory impairment condition; post-traumatic stress disorder; a drug addiction).

In some embodiments, the formula (I) compounds described herein selectively inhibit HDAC3, e.g., selectively inhibit HDAC3 over HDAC1 and HDAC2 (e.g exhibiting 5-fold or greater selectivity, e.g. exhibiting 25-fold or greater selectivity) and exhibit enhanced brain penetration (e.g., as described above).

In some embodiments, the formula (I) compounds described herein selectively inhibit HDAC1 and/or HDAC2, e.g., selectively inhibit HDAC1 and/or HDAC2 over HDAC3 (e.g exhibiting 5-fold or greater selectivity, e.g. exhibiting 25-fold or greater selectivity) and exhibit enhanced brain penetration (e.g., as described above).

Embodiments can also include any one or more of the features described in the detailed description and in the claims.

Definitions

The term "hepatocyte" refers to preparations, e.g., commercially available preparations, of liver tissue derived cells that can be obtained from mouse, rat, dog, monkey, or human liver tissue.

The term "mammal" includes organisms, which include mice, rats, cows, sheep, pigs, rabbits, goats, horses, monkeys, dogs, cats, and humans.

"An effective amount" refers to an amount of a compound that confers a therapeutic effect (e.g., treats, e.g., controls, relieves, ameliorates, alleviates, or slows the progression of; or prevents, e.g., delays the onset of or reduces the risk of developing, a disease, disorder, or condition or symptoms thereof) on the treated subject. The therapeutic effect may be objective (i.e., measurable by some test or marker) or subjective (i.e., subject gives an indication of or feels an effect). An effective amount of the compound described above may range from about 0.01 mg/kg to about 1000 mg/kg, (e.g., from about 0.1 mg/kg to about 100 mg/kg, from about 1 mg/kg to about 100 mg/kg). Effective doses will also vary depending on route of administration, as well as the possibility of co-usage with other agents.

The term "halo" or "halogen" refers to any radical of fluorine, chlorine, bromine or iodine.

In general, and unless otherwise indicated, substituent (radical) prefix names are derived from the parent hydride by either (i) replacing the "ane" in the parent hydride with the suffix "yl;" or (ii) replacing the "e" in the parent hydride with the suffix "yl;" (here the atom(s) with the free valence, when specified, is (are) given numbers as low as is consistent with any established numbering of the parent hydride). Accepted contracted names, e.g., furyl, pyridyl, and piperidyl, and trivial names, e.g., phenyl and thienyl are also used herein throughout. Conventional numbering/lettering systems are also adhered to for substituent numbering.

The following definitions are used, unless otherwise described. Specific and general values listed below for radicals, substituents, and ranges, are for illustration only; they do not exclude other defined values or other values within defined ranges for the radicals and substituents. Alkyl, alkoxy, and the like denote both straight and branched groups.

As used herein, the term "alkyl," employed alone or in combination with other terms, refers to a saturated hydrocarbon group that may be straight-chain or branched. In some embodiments, the alkyl group contains 1 to 12, 1 to 8, or 1 to 6 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, n-heptyl, n-octyl, and the like. In some embodiments, the alkyl moiety is methyl, ethyl, n-propyl, isopropyl, n-butyl, isobutyl, tert-butyl, n-pentyl, isopentyl, neopentyl, n-hexyl, or 2,4,4-trimethylpentyl.

Throughout the definitions, the term "Cy-Cz" (e.g., C1-C6 and the like) is used, wherein y and z are integers and indicate the number of carbons, wherein y-z indicates a range which includes the endpoints.

As referred to herein, the term "alkoxy group" refers to a group of formula —O(alkyl). Alkoxy can be, for example, methoxy, ethoxy, propoxy, isopropoxy, butoxy, iso-butoxy, sec-butoxy, pentoxy, 2-pentoxy, 3-pentoxy, or hexyloxy.

As used herein, the term "aryl," employed alone or in combination with other terms, refers to a monocyclic aromatic hydrocarbon moiety or a polycyclic hydrocarbon moiety (e.g., having 2, 3 or 4 fused linked rings) that includes at least one aromatic ring. Examples include, but are not limited to, phenyl, 1-naphthyl, 2-naphthyl, indanyl and tetralinyl. In some embodiments, aryl groups have from 6 to 10 carbon atoms.

As referred to herein, "heteroaryl" refers to an aromatic monocyclic or fused bicyclic, or polycyclic ring comprising 5-10 ring atoms that includes at least one aromatic ring, each of which containing at least one (typically one to about three) independently selected nitrogen, oxygen, or sulfur ring atoms (independently selected when more than one ring is present). Examples of heteroaryl groups include, but are not limited to pyridyl, pyrazolyl, pyrrolyl, 2-oxo-indolyl, quinolinyl, isoquinolinyl, tetrahydro-isoquinolinyl, benzofuranyl, indolyl, benzodioxanyl, benzodioxolyl (aka. methylenedioxyphenyl) and corresponding difluoro ($CF_2$) analog, thiazolyl, 2-oxopyridinyl, pyridinyl N-oxide, pyrimidinyl, thienyl, furanyl, oxazolyl, isoxazolyl, pyridazinyl, imidazolyl, pyrazinyl, isothiazolyl, 1,2-thiazinyl-1,1-dioxide, benzimidazolyl, thiadiazolyl, benzopyranyl, benzothiazolyl, benzotriazolyl, benzoxazolyl, benzothienyl, oxadiazolyl, triazolyl, tetrazolyl, dioxoindolyl (isatin), phthalimido; heteroaryls that contain a bridgehead nitrogen ring atom and optionally other heteroatom ring atoms, such as indolizinyl, pyrrolopyrimidinyl, pyrazolopyridinyl, imidazopyridinyl, imidazopyriazinyl, triazolopyridinyl, imidazothiazolyl, imidazooxazolyl); and the dihydro and tetrahydro congeners of the fully unsaturated ring systems.

As used herein, the phrase "optionally substituted" means unsubstituted (e.g., substituted with a H) or substituted. As used herein, the term "substituted" means that a hydrogen atom is removed and replaced by a substituent. It is understood that substitution at a given atom is limited by valency. The use of a substituent (radical) prefix name such as alkyl without the modifier "optionally substituted" or "substituted" is understood to mean that the particular substituent is unsubstituted. However, the use of "fluoro Cy-Cz alkyl" without the modifier "optionally substituted" or "substituted" is still understood to mean an alkyl group, in which at least one hydrogen atom is replaced by fluoro.

Unless indicated otherwise, the nomenclature of substituents that are not explicitly defined herein are arrived at by naming the terminal portion of the functionality followed by the adjacent functionality toward the point of attachment. In generally, the point of attachment for a substituent is indicated by the last term in the group. For example, (heterocyclyl)-(C1-C6) alkyl refers to a moiety of heterocyclyl -alkylene-, wherein the alkylene linker has 1 to 6 carbons, and the substituent is attached through the alkylene linker.

As used herein, the term "cycloalkyl," employed alone or in combination with other terms, refers to a saturated, cyclic hydrocarbon moiety comprising 3-10 carbon atoms. Exemplary cycloalkyl groups include, without limitation, cyclopropyl, cyclobutyl, cyclopentyl, cyclohexyl, and cycloheptyl. It is understood that when two substituents are joined to form a cycloalkyl group, it may be a cycloalkylene.

As used herein, the term "cycloalkenyl," employed alone or in combination with other terms, refers to a partially saturated, cyclic hydrocarbon moiety comprising 3-10 carbon atoms. An exemplary cycloalkenyl group is cyclohexenyl. It is understood that when two substituents are joined to form a cycloalkenyl group, it may be a cycloalkenylene.

As used herein, the term "cyano," employed alone or in combination with other terms, refers to a group of formula —CN, wherein the carbon and nitrogen atoms are bound together by a triple bond.

As used herein, the term "halo Cy-Cz alkyl" and the like employed alone or in combination with other terms, refers to an alkyl group having from one halogen atom to 2n+1 halogen atoms which may be the same or different, where "n" is the number of carbon atoms in the alkyl group. In some embodiments, the halogen atoms are fluoro atoms.

As used herein, "haloalkoxy," employed alone or in combination with other terms, refers to a group of formula —O-haloalkyl. An example haloalkoxy group is $OCF_3$. In some embodiments, the halogen atoms are fluoro atoms.

As used herein, the term "heterocyclyl" employed alone or in combination with other terms, refers to a saturated ring system comprising 3-10 ring atoms, which has carbon ring atoms and at least one heteroatom ring atom selected from nitrogen, sulfur, and oxygen (independently selected when more than one is present). When the heterocyclyl group contains more than one heteroatom, the heteroatoms may be the same or different. Heterocyclyl groups can include mono- or bicyclic or polycyclic (e.g., having 2 fused rings) ring systems. Heterocyclyl groups can also include bridgehead heterocycloalkyl groups. As used herein, "bridgehead heterocyclyl group" refers to a heterocyclyl moiety containing at least one bridgehead heteroatom (e.g., nitrogen). In some embodiments, the carbon atoms or hetereoatoms in the ring(s) of the heterocycloalkyl group can be oxidized to form a carbonyl, or sulfonyl group (or other oxidized linkage) or a nitrogen atom can be quaternized. It is understood that when two substituents are joined to form a heterocycloalkyl group, it may be a heterocycloalkylene.

As to any of the above groups that contain one or more substituents, it is understood, of course, that such groups do not contain any substitution or substitution patterns that are sterically impractical and/or synthetically unfeasible. In addition, the compounds described herein include all stereochemical isomers arising from the substitution of these compounds.

Unless otherwise defined, all technical and scientific terms used herein have the same meaning as commonly understood by one of ordinary skill in the art. Although methods and materials similar or equivalent to those described herein can be used in the practice or testing of embodiments described herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the disclosure will be apparent from the following detailed description, and from the claims.

It is appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable sub-combination.

Thus, for ease of exposition, it is also understood that where in this specification, a group is defined by "as defined anywhere herein" (or the like), the definitions for that particular group include the first occurring and broadest generic definition as well as any sub-generic and specific definitions delineated anywhere in this specification. Also, for ease of exposition, the definition "substituent other than hydrogen" refers collectively to the non-hydrogen possibilities for that particular variable.

DETAILED DESCRIPTION

This disclosure features compounds having formula (I), or a pharmaceutically acceptable salt thereof:

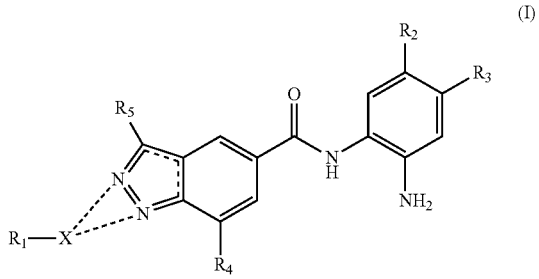

compositions (e.g., pharmaceutical compositions) containing the same and methods of using the same.

I. COMPOUNDS

A. Variable X

1.

In some embodiments, X is —Y—[C($R^a$)$_2$]$_a$-A-[C($R^b$)$_2$]$_b$—B—. Embodiments can also include one or more of the features described in [a]-[d] below.

a.

A is a bond and/or B is a bond (in some embodiments, each of A and B is a bond; or one of A and B (e.g., B) is a bond, and the other of A and B (e.g., A) is other than a bond, e.g., 0 or NR$^f$, e.g., O; in embodiments, each of A and B is other than S(O)$_m$).

Each occurrence of $R^a$ and $R^b$ (when present) is independently selected from H, F, OH, C1-C6 alkyl, C3-C6 cycloalkyl, NH$_2$, OCO—(C1-C6 alkyl), OCO—(C3-C6 cycloalkyl), C1-C6 alkoxy C1-C6 fluoroalkoxy, and cyano.

Each occurrence of $R^a$ and $R^b$ (when present) is independently selected from H, F, C1-C6 alkyl, and C3-C6 cycloalkyl.

Each occurrence of $R^a$ and $R^b$ (when present) is H.

One or more (e.g., one) of the following apply:

any two $R^a$, together with the carbons to which each is attached, together form C3-C6 cycloalkyl or heterocyclyl including 3-6 ring atoms, in which one of the heterocyclyl ring atoms is selected from O; S(O)$_m$ and NR$^g$; in these embodiments, any remaining occurrences of $R^a$ and any occurrence of $R^b$ are each independently defined according to any one or more of the preceding or following definitions pertaining to $R^a$ and $R^b$; or one $R^a$ and one $R^b$, together with the carbons to which each is attached, form C3-C6 cycloalkyl or heterocyclyl including 3-6 ring atoms, in which one of the heterocyclyl ring atoms is selected from O; S(O)$_m$ and NR$^g$; in these embodiments, the other $R^a$, the other $R^b$, and any other remaining occurrences of $R^a$ and $R^b$ are each independently defined according to any one or more of the preceding or following definitions pertaining to $R^a$ and $R^b$; or any two $R^b$, together with the carbons to which each is attached, form C3-C6 cycloalkyl or heterocyclyl including 3-6 ring atoms, in which one of the ring atoms is selected from O; S(O)$_m$ and NR$^g$; in these embodiments, each occurrence of $R^a$ and any other remaining occurrences of $R^b$ are each independently defined according to any one or more of the preceding definitions pertaining to $R^a$ and $R^b$.

b.

In some embodiments, Y is CR$^c$=CR$^d$ (in some embodiments, the double bond between CR$^c$ and CR$^d$ has the trans configuration; in other embodiments, the double bond between CR$^c$ and CR$^d$ has the cis configuration). Embodiments can include one or more of the following features.

The double bond between CR$^c$ and CR$^d$ has the trans configuration. Each of R$^c$ and R$^d$ is, independently, selected from H, F, OH, C1-C6 alkyl, C3-C5 cycloalkyl, NH$_2$, OCO—(C1-C6 alkyl), OCO—(C3-C5 cycloalkyl), C1-C6 alkoxy, C1-C6 fluoroalkoxy, and cyano. In certain embodiments, each of R$^c$ and R$^d$ is H.

A is a bond and/or B is a bond (in some embodiments, each of A and B is a bond).

Each of $R^a$ and $R^b$ can be as defined anywhere herein (see, for example, the $R^a$ and $R^b$ features described above in section [I][A][1][a]).

a is 1 or 2 (e.g., 1). b is 0 or 1 (e.g., 0).

a is 1 or 2, e.g., 1; and b is 0 or 1, e.g., 0 (in further embodiments, each of A and B is also a bond.

b is 0 (in embodiments, a is 1 or 2, e.g., 1; in further embodiments, each of A and B is also a bond).

X is —CH=CH—C($R^a$)$_2$—. In certain embodiments, each $R^a$ is hydrogen. In other embodiments, each $R^a$ is a substituent other than hydrogen (e.g., C1-C6 alkyl), and each $R^a$ can be the same or different, e.g., the same. For example, each $R^a$ can be the same C1-C6 alkyl, such as CH$_3$.

X is —CH=CH—CH($R^a$)—. In certain embodiments, $R^a$ is hydrogen; in other embodiments, $R^a$ is a substituent other than hydrogen (e.g., as described above).

X is —CH=CH—C($R^a$)$_2$—C($R^a$)$_2$. In certain embodiments, each $R^a$ is hydrogen. In other embodiments, each $R^a$ is a substituent other than hydrogen (e.g., C1-C6 alkyl), and each $R^a$ can be the same or different, e.g., the same. For example, each $R^a$ can be the same C1-C6 alkyl, such as CH$_3$. In still other embodiments, in one germinal pair of $R^a$'s, each $R^a$ is hydrogen; and in the other germinal pair of $R^a$'s, each $R^a$ is a substituent other than hydrogen (e.g., as described above).

X is —CH=CHCH($R^a$)CH($R^a$). In certain embodiments, each $R^a$ is hydrogen; in other embodiments, each $R^a$ is a substituent other than hydrogen; in still other embodiments, one $R^a$ is hydrogen, and the other is a substituent other than hydrogen.

For example, X is —CH=CH—CH$_2$— or —CH=CH—CH$_2$—CH$_2$— (e.g., in the foregoingmbodiments, the double bond can have the trans configuration; and further each of A and B can be a bond). In certain embodiments, X is —CH=CH—CH$_2$— (e.g., trans).

c.

In some embodiments, Y is O, NR$^e$, or S(O)$_m$; e.g., Y is O or NR$^e$. Embodiments can include one or more of the following features.

Y is O.

Y is NR$^e$ (e.g., R$^e$ is C1-C6 alkyl).

A is a bond and/or B is a bond (in some embodiments, each of A and B is a bond).

Each of R$^a$ and R$^b$ can be as defined anywhere herein (see, for example, the R$^a$ and R$^b$ features described above in section [I][A][1][a]).

a is 2 or 3 (e.g., 2) and b is optionally other than 0 (e.g., 1 or 2); in embodiments, A is a bond; or A is other than a bond, e.g., O or NR$^f$, e.g., O and B is a bond. Some examples are provided in the following: a is 2 or 3 (e.g., 2), b is 0; and each of A and B is a bond. a is 2 or 3 (e.g., 2), b is other than 0 (e.g., 1 or 2), and each of A and B is a bond. a is 2 or 3 (e.g., 2), b is other than 0 (e.g., 2 or 3), A is other than a bond, e.g., O or NR$^f$, e.g., O, and B is a bond.

For example, X is —O—(CH$_2$)$_{2-3(e.g.,2)}$ or —N(CH$_3$)—(CH$_2$)$_{2-3(e.g., 2)}$.

d.

In some embodiments, Y is a bond. Embodiments can include one or more of the following features.

A is a bond, O, or NR$^e$ (e.g., A is a bond or O, e.g., A is a bond) and/or B is a bond. In certain embodiments, A is a bond and B is a bond.

Each of R$^a$ and R$^b$ can be as defined anywhere herein (see, for example, the R$^a$ and R$^b$ features described above in section [I][A][1][a]).

b is 0 (in embodiments, a can be 1, 2, or 3 (e.g., 1) and one or more of the following can apply: A is a bond, A is other than a bond, such as O; B is a bond, each of R$^a$ is H; e.g., A is a bond, a is 1, B is a bond; e.g., X is CH$_2$).

b is 1, 2, or 3 (in embodiments, a can be 1, 2, or 3 and one or more of the following can apply: A is a bond, A is other than a bond, such as O;B is a bond, each of R$^a$ is H, each of R$^b$ is H). In certain of these embodiments, X has a span of not more than 4 atoms.

2.

In some embodiments, X is a bond.

B. Variables R4 and R5

In some embodiments, R4 is hydrogen or halo (e.g., chloro).

In some embodiments, R4 is hydrogen.

In some embodiments, R5 is hydrogen.

In some embodiments, each of R4 and R5 is H.

In some embodiments, each of R4 and R5 is a substituent other than H.

C. Variable R1

1.

In some embodiments, R1 is C6-C10 aryl, which is optionally substituted with from 1-3 R$^o$. In certain embodiments, R1 is phenyl or naphthyl (e.g., phenyl), which is optionally substituted with from 1-3 R$^o$ (in embodiments, each R$^o$ is independently selected from F, OH, C1-C6 alkyl, fluoro(C1-C6) alkyl C3-C6 cycloalkyl, NH$_2$, C1-C6 alkoxy, C1-C6 fluoroalkoxy, and cyano).

In other embodiments, R1 is C8-C10 aryl, which contains a phenyl ring fused to a non-aromatic ring and which is optionally substituted with from 1-3 R$^o$ (e.g., optionally substituted indanyl or tetralinyl).

2.

In some embodiments, R1 is monocyclic or bicyclic heteroaryl including from 5-10 ring atoms, which is optionally substituted with from 1-3 R$^o$; wherein from 1-4 of the ring atoms is/are a heteroatom independently selected from O, N, N—H, N—R$^o$, and S.

In certain embodiments, R1 is monocyclic heteroaryl, such as pyridyl.

In other embodiments, R1 is bicyclic heteroaryl, such as those that are fully aromatic such as indolyl and the like.

In still other embodiments, R1 is bicyclic heteroaryl that contains a bridgehead nitrogen ring atom and optionally other heteroatom ring atoms, such as indolizinyl, pyrrolopyrimidinyl, pyrazolopyridinyl, imidazopyridinyl, imidazopyriazinyl, triazolopyridinyl, imidazothiazolyl, imidazooxazolyl.

Other examples of R1 heteroaryl groups include, without limitation, pyrazolyl, pyrrolyl, 2-oxo-indolyl, quinolinyl, isoquinolinyl, tetrahydro-isoquinolinyl, benzofuranyl, benzodioxanyl, benzodioxolyl (aka. methylenedioxyphenyl) and corresponding difluoro (CF$_2$) analog, thiazolyl, 2-oxopyridinyl, pyridinyl N-oxide, pyrimidinyl, thienyl, furanyl, oxazolyl, isoxazolyl, pyridazinyl, imidazolyl, pyrazinyl, isothiazolyl, 1,2-thiazinyl-1,1-dioxide, benzimidazolyl, thiadiazolyl, benzopyranyl, benzothiazolyl, benzotriazolyl, benzoxazolyl, benzothienyl, oxadiazolyl, triazolyl, tetrazolyl, dioxoindolyl (isatin), phthalimido, and the dihydro and tetrahydro congeners of the fully unsaturated ring systems.

3.

In some embodiments, R1 is heterocyclyl including from 4-10 ring atoms, which is optionally substituted with from 1-3 R$^o$; wherein from 1-4 of the ring atoms is/are a heteroatom independently selected from O, N, N—H, N—R$^o$, and S (e.g., bicyclic heterocyclyl containing a bridgehead nitrogen ring atom and optionally other heteroatom ring atoms).

Examples of R1 heterocyclyl groups include, without limitation, piperidinyl, morpholinyl, pyrrolidinyl, azetidinyl, azepanyl, isoxazolidinyl, oxazolidinyl, thiazolidinyl, imidazolinyl, quinuclidinyl, isothiazolidinyl, tetrahydrofuranyl, tetrahydropyranyl, thiamorpholinyl, thiamorpholinyl sulfoxide, thiamorpholinyl sulfone, dioxanyl, tropanyl and other bridged bicyclic amines, quiniclidinyl.

4.

In some embodiments, R1 is H.

5.

In some embodiments, R1 is C3-C10 (e.g., C3-C8, C3-C6, C3-C5) cycloalkyl or C3-C10 (e.g., C3-C8, C3-C6, C3-C5)cycloalkenyl, each of which is optionally substituted with from 1-3 R$^o$.

In some embodiments, R1 is C3-C10 cycloalkyl, which is optionally substituted with from 1-3 R$^o$.

In some embodiments, R1 is C3-C8 cycloalkyl, which is optionally substituted with from 1-3 R$^o$.

In some embodiments, R1 is C3-C6 cycloalkyl, which is optionally substituted with from 1-3 R$^o$.

In some embodiments, R1 is C3-C5 cycloalkyl, which is optionally substituted with from 1-3 R$^o$.

In some embodiments, R1 is unsubstituted C3-C10 cycloalkyl. In some embodiments, R1 is unsubstituted C3-C8 cycloalkyl. In some embodiments, R1 is unsubstituted C3-C6 cycloalkyl. In some embodiments, R1 is unsubstituted C3-C5 cycloalkyl.

Examples of R1 cycloalkyl include, without limitation, cyclopropyl, cyclobutyl, cyclopentyl, cyclohexyl, 2,6-dimethylcyclohexyl, 2,2,6,6-tetramethylcyclohexyl.

In some embodiments, R1 is cyclopropyl, which is optionally substituted with from 1-3 R$^o$. In some embodiments, R1 is unsubstituted cyclopropyl.

D. Variables R2 and R3

1.

In some embodiments, R2 is a substituent other than hydrogen (e.g., phenyl, substituted phenyl, thienyl, thiazolyl, and pyrazol-1-yl), and R3 is hydrogen. In certain embodiments, the compounds can exhibit selectivity for HDAC 1 and/or 2.

2.

In some embodiments, R2 is hydrogen, and R3 is a substituent other than hydrogen (e.g., fluoro). In certain embodiments, the compounds can exhibit selectivity for HDAC 3.

3.

In some embodiments, each of R2 and R3 is hydrogen.

E. Non-Limiting Combinations

In some embodiments, variables, X, R1, R2, R3, R4, R5, and $R^o$ (and their attendant sub-definitions) can be combined as provided below:

(a)

X is:
- (i) —Y—[C($R^a$)$_2$]-A-[C($R^b$)$_2$]$_b$—B—;
- (ii) direct bond; or
- (iii) C=O, C($R^j$)$_2$—C(=O), C(=O)—C($R^j$)$_2$, SO$_2$—N$R^k$, N$R^k$—SO$_2$, C(=O)N$R^k$ or N$R^k$—C(=O);

R1 is:
- (i) monocyclic or bicyclic heteroaryl including from 5-10 ring atoms, which is optionally substituted with from 1-3 $R^o$; wherein from 1-4 of the ring atoms are a heteroatom independently selected from O, N, N—H, N—$R^o$, and S;
- (ii) C6-C10 aryl, which is optionally substituted with from 1-3 $R^o$;
- (iii) C3-C10 cycloalkyl or C3-C10 cycloalkenyl, each of which is optionally substituted with from 1-3 $R^o$;
- (iv) heterocyclyl including from 3-10 ring atoms, which is optionally substituted with from 1-3 $R^o$; wherein from 1-4 of the ring atoms are a heteroatom independently selected from O, N, N—H, N—$R^o$, and S; or
- (v) hydrogen;

$R^o$ is independently selected from the group consisting of halogen; C1-C6 alkyl; fluoro(C1-C6)alkyl; hydroxyl; hydroxy($C_1$-$C_4$)alkyl; C1-C6 alkoxy; fluoro(C1-C6) alkoxy; (C1-C6 alkyl)C(O)—; (C1-C6 alkyl)NH—; (C1-C6 alkyl)$_2$N—; —N*)($R^{o'}$)$_2$, wherein $R^{o'}$—N*—$R^{o'}$ together form a saturated ring having 5 or 6 ring atoms, in which 1 or 2 ring atoms are optionally a heteroatom independently selected from NH, N(C1-C6alkyl), O, or S; cyano; phenyl; heteroaryl including from 5-6 ring atoms, wherein from 1-4 of the ring atoms are a heteroatom independently selected from O, N, N—H, N—$R^{o''}$ and S, each of which is optionally substituted with from 1-3 $R^{o''}$; and SO$_2$—(C1-C6)alkyl;

R4 is hydrogen or halo;

R5 is hydrogen; and (i) each of R2 and R3 is hydrogen; or (ii) R2 is hydrogen, and R3 is fluoro; or (iii) R2 is a substituent other than hydrogen, and R3 is hydrogen;

(b)

X is —Y—[C($R^a$)$_2$]$_a$-A-[C($R^b$)$_2$]$_b$—B—;

R1 is:
- (i) monocyclic or bicyclic heteroaryl including from 5-10 ring atoms, which is optionally substituted with from 1-3 $R^o$; wherein from 1-4 of the ring atoms are a heteroatom independently selected from O, N, N—H, N—$R^o$, and S;
- (ii) C6-C10 aryl, which is optionally substituted with from 1-3 $R^o$; or
- (iii) C3-C10 cycloalkyl or C3-C10 cycloalkenyl, each of which is optionally substituted with from 1-3 $R^o$;
- (iv) heterocyclyl including from 3-10 ring atoms, which is optionally substituted with from 1-3 $R^o$; wherein from 1-4 of the ring atoms are a heteroatom independently selected from O, N, N—H, N—$R^o$, and S; or
- (v) hydrogen;

$R^o$ is independently selected from the group consisting of halogen; C1-C6 alkyl; fluoro(C1-C6)alkyl; hydroxyl; hydroxy($C_1$-$C_4$)alkyl; C1-C6 alkoxy; fluoro(C1-C6) alkoxy; (C1-C6 alkyl)C(O)—; (C1-C6 alkyl)NH—; (C1-C6 alkyl)$_2$N—; —N*)($R^{o'}$)$_2$, wherein $R^{o'}$—N*—$R^{o'}$ together form a saturated ring having 5 or 6 ring atoms, in which 1 or 2 ring atoms are optionally a heteroatom independently selected from NH, N(C1-C6alkyl), O, or S; cyano; phenyl; heteroaryl including from 5-6 ring atoms, wherein from 1-4 of the ring atoms are a heteroatom independently selected from O, N, N—H, N—$R^{o''}$, and S, each of which is optionally substituted with from 1-3 $R^{o''}$; and SO$_2$—(C1-C6)alkyl;

R4 is hydrogen or halo;

R5 is hydrogen; and (i) each of R2 and R3 is hydrogen; or (ii) R2 is hydrogen, and R3 is fluoro; or (iii) R2 is a substituent other than hydrogen, and R3 is hydrogen;

(c)

X is —Y—[C($R^a$)$_2$]$_a$-A-[C($R^b$)$_2$]$_b$—B—, and Y is a bond;

R1 is:
- (i) monocyclic or bicyclic heteroaryl including from 5-10 ring atoms, which is optionally substituted with from 1-3 $R^o$; wherein from 1-4 of the ring atoms are a heteroatom independently selected from O, N, N—H, N—$R^o$, and S;
- (ii) C6-C10 aryl, which is optionally substituted with from 1-3 $R^o$; or
- (iii) C3-C10 cycloalkyl or C3-C10 cycloalkenyl, each of which is optionally substituted with from 1-3 $R^o$;
- (iv) heterocyclyl including from 3-10 ring atoms, which is optionally substituted with from 1-3 $R^o$; wherein from 1-4 of the ring atoms are a heteroatom independently selected from O, N, N—H, N—$R^O$, and S; or
- (v) hydrogen;

$R^o$ is independently selected from the group consisting of halogen, C1-C6 alkyl, and fluoro(C1-C6)alkyl;

R4 is hydrogen or halo;

R5 is hydrogen; and (i) each of R2 and R3 is hydrogen; or (ii) R2 is hydrogen, and R3 is fluoro; or (iii) R2 is a substituent other than hydrogen, and R3 is hydrogen;

(d)

X is —Y—[C($R^a$)$_2$]$_a$-A-[C($R^b$)$_2$]$_b$—B—, Y is a bond, and each occurrence of $R^a$ and $R^b$ is independently selected from H, F, OH, C1-C6 alkyl, C3-C6 cycloalkyl, NH$_2$, OCO—(C1-C6 alkyl), OCO—(C3-C6 cycloalkyl), C1-C6 alkoxy, C1-C6 fluoroalkoxy, and cyano;

R1 is:
- (i) monocyclic or bicyclic heteroaryl including from 5-10 ring atoms, which is optionally substituted with from 1-3 $R^o$; wherein from 1-4 of the ring atoms are a heteroatom independently selected from O, N, N—H, N—$R^o$, and S;
- (ii) C6-C10 aryl, which is optionally substituted with from 1-3 $R^o$; or (iii) C3-C10 cycloalkyl or C3-C10 cycloalkenyl, each of which is optionally substituted with from 1-3 R°;
(iv) heterocyclyl including from 3-10 ring atoms, which is optionally substituted with from 1-3 R°; wherein from 1-4 of the ring atoms are a heteroatom independently selected from O, N, N—H, N—R°, and S; or
(v) hydrogen;

R° is independently selected from the group consisting of halogen, C1-C6 alkyl, and fluoro(C1-C6)alkyl;

R4 is hydrogen or halo;

R5 is hydrogen; and (i) each of R2 and R3 is hydrogen; or (ii) R2 is hydrogen, and R3 is fluoro; or (iii) R2 is a substituent other than hydrogen, and R3 is hydrogen;

(e)

X is:
  (i) —Y—[C(R$^a$)$_2$]$_a$-A-[C(R$^b$)$_2$]$_b$—B—;
  (ii) direct bond; or
  (iii) C═O, C(R$^j$)$_2$—C(═O), or C(═O)—C(R$^j$)$_2$, SO$_2$—NR$^k$, NR$^k$—SO$_2$, C(═O)NR$^k$ and NR$^k$—C(═O);

R1 is C3-C10 cycloalkyl or C3-C10 cycloalkenyl, optionally substituted with from 1-3 R°;

R° is independently selected from the group consisting of halogen, C1-C6 alkyl, and fluoro(C1-C6)alkyl;

R4 is hydrogen or halo;

R5 is hydrogen; and (i) each of R2 and R3 is hydrogen; or (ii) R2 is hydrogen, and R3 is fluoro; or (iii) R2 is a substituent other than hydrogen, and R3 is hydrogen;

(f)

X is —Y—[C(R$^a$)$_2$]$_a$-A-[C(R$^b$)$_2$]$_b$—B—;

R1 is C3-C10 cycloalkyl or C3-C10 cycloalkenyl, optionally substituted with from 1-3 R°;

R° is independently selected from the group consisting of halogen; C1-C6 alkyl; fluoro(C1-C6)alkyl; hydroxyl; hydroxy(C$_1$-C$_4$)alkyl; C1-C6 alkoxy; fluoro(C1-C6)alkoxy; (C1-C6 alkyl)C(O)—; (C1-C6 alkyl)NH—; (C1-C6 alkyl)$_2$N—; —N*(R°')$_2$, wherein R°'—N*—R°' together form a saturated ring having 5 or 6 ring atoms, in which 1 or 2 ring atoms are optionally a heteroatom independently selected from NH, N(C1-C6alkyl), O, or S; cyano; phenyl; heteroaryl including from 5-6 ring atoms, wherein from 1-4 of the ring atoms are a heteroatom independently selected from O, N, N—H, N—R°'', and S, each of which is optionally substituted with from 1-3 R°''; and SO$_2$—(C1-C6)alkyl;

R4 is hydrogen or halo;

R5 is hydrogen; and (i) each of R2 and R3 is hydrogen; or (ii) R2 is hydrogen, and R3 is fluoro; or (iii) R2 is a substituent other than hydrogen, and R3 is hydrogen;

(g)

X is —Y—[C(R$^a$)$_2$]$_a$-A-[C(R$^b$)$_2$]$_b$—B—;

R1 is C3-C10 cycloalkyl or C3-C10 cycloalkenyl, optionally substituted with from 1-3 R°;

R° is independently selected from the group consisting of: halogen; C1-C6 alkyl; fluoro(C1-C6)alkyl; hydroxyl; hydroxy(C$_1$-C$_4$)alkyl; C1-C6 alkoxy; fluoro(C1-C6)alkoxy; (C1-C6 alkyl)NH—; (C1-C6 alkyl)$_2$N—; cyano; and SO$_2$—(C1-C6)alkyl;

R4 is hydrogen or halo;

R5 is hydrogen; and (i) each of R2 and R3 is hydrogen; or (ii) R2 is hydrogen, and R3 is fluoro; or (iii) R2 is a substituent other than hydrogen, and R3 is hydrogen;

(h)

X is —Y—[C(R$^a$)$_2$]$_a$-A-[C(R$^b$)$_2$]$_b$—B—, and Y is a bond;

R1 is C3-C10 cycloalkyl or C3-C10 cycloalkenyl, optionally substituted with from 1-3 R°;

R° is independently selected from the group consisting of halogen, C1-C6 alkyl, and fluoro(C1-C6)alkyl;

R4 is hydrogen or halo;

R5 is hydrogen; and (i) each of R2 and R3 is hydrogen; or (ii) R2 is hydrogen, and R3 is fluoro; or (iii) R2 is a substituent other than hydrogen, and R3 is hydrogen;

(i)

X is —Y—[C(R$^a$)$_2$]$_a$-A-[C(R$^b$)$_2$]$_b$—B—, Y is a bond, and each occurrence of R$^a$ and R$^b$ is independently selected from H, F, OH, C1-C6 alkyl, C3-C6 cycloalkyl, NH$_2$, OCO—(C1-C6 alkyl), OCO—(C3-C6 cycloalkyl), C1-C6 alkoxy, C1-C6 fluoroalkoxy, and cyano;

R1 is C3-C10 cycloalkyl or C3-C10 cycloalkenyl, optionally substituted with from 1-3 R°;

R° is independently selected from the group consisting of: halogen; C1-C6 alkyl; fluoro(C1-C6)alkyl; hydroxyl; hydroxy(C$_1$-C$_4$)alkyl; C1-C6 alkoxy; fluoro(C1-C6)alkoxy; (C1-C6 alkyl)NH—; (C1-C6 alkyl)$_2$N—; cyano; and SO$_2$—(C1-C6)alkyl;

R4 is hydrogen or halo;

R5 is hydrogen; and (i) each of R2 and R3 is hydrogen; or (ii) R2 is hydrogen, and R3 is fluoro; or (iii) R2 is a substituent other than hydrogen, and R3 is hydrogen;

(j)

X is:
  (i) —Y—[C(R$^a$)$_2$]$_a$-A-[C(R$^b$)$_2$]$_b$—B—;
  (ii) direct bond; or
  (iii) C═O, C(R$^j$)$_2$—C(═O), or C(═O)—C(R$^j$)$_2$, SO$_2$—NR$^k$, NR$^k$—SO$_2$, C(═O)NR$^k$ and NR$^k$—C(═O);

R1 is monocyclic or bicyclic heteroaryl including from 5-10 ring atoms, optionally substituted with from 1-3 R°; wherein from 1-4 of the ring atoms are a heteroatom independently selected from O, N, N—H, N—R°, and S;

R° is independently selected from the group consisting of: halogen; C1-C6 alkyl; fluoro(C1-C6)alkyl; hydroxyl; hydroxy(C$_1$-C$_4$)alkyl; C1-C6 alkoxy; fluoro(C1-C6)alkoxy; (C1-C6 alkyl)NH—; (C1-C6 alkyl)$_2$N—; cyano; and SO$_2$—(C1-C6)alkyl;

R4 is hydrogen or halo;

R5 is hydrogen; and (i) each of R2 and R3 is hydrogen; or (ii) R2 is hydrogen, and R3 is fluoro; or (iii) R2 is a substituent other than hydrogen, and R3 is hydrogen;

(k)

X is —Y—[C(R$^a$)$_2$]$_a$-A-[C(R$^b$)$_2$]$_b$—B—;

R1 is monocyclic or bicyclic heteroaryl including from 5-10 ring atoms, optionally substituted with from 1-3 R°; wherein from 1-4 of the ring atoms are a heteroatom independently selected from O, N, N—H, N—R°, and S;

R° is independently selected from the group consisting of: halogen; C1-C6 alkyl; fluoro(C1-C6)alkyl; hydroxyl; hydroxy(C$_1$-C$_4$)alkyl; C1-C6 alkoxy; fluoro(C1-C6)alkoxy; (C1-C6 alkyl)NH—; (C1-C6 alkyl)$_2$N—; cyano; and SO$_2$—(C1-C6)alkyl;

R4 is hydrogen or halo;

R5 is hydrogen; and (i) each of R2 and R3 is hydrogen; or (ii) R2 is hydrogen, and R3 is fluoro; or (iii) R2 is a substituent other than hydrogen, and R3 is hydrogen;

(l)

X is —Y—[C($R^a$)$_2$]$_a$-A-[C($R^b$)$_2$]$_b$—B—, and Y is a bond;

R1 is monocyclic or bicyclic heteroaryl including from 5-10 ring atoms, optionally substituted with from 1-3 $R^o$; wherein from 1-4 of the ring atoms are a heteroatom independently selected from O, N, N—H, N—$R^o$, and S;

$R^o$ is independently selected from the group consisting of: halogen; C1-C6 alkyl; fluoro(C1-C6)alkyl; hydroxyl; hydroxy($C_1$-$C_4$)alkyl; C1-C6 alkoxy; fluoro(C1-C6) alkoxy; (C1-C6 alkyl)NH—; (C1-C6 alkyl)$_2$N—; cyano; and SO$_2$—(C1-C6)alkyl;

R4 is hydrogen or halo;

R5 is hydrogen; and (i) each of R2 and R3 is hydrogen; or (ii) R2 is hydrogen, and R3 is fluoro; or (iii) R2 is a substituent other than hydrogen, and R3 is hydrogen;

(m)

X is —Y—[C($R^a$)$_2$]$_a$-A-[C($R^b$)$_2$]$_b$—B—, Y is a bond, and each occurrence of $R^a$ and $R^b$ is independently selected from H, F, OH, C1-C6 alkyl, C3-C6 cycloalkyl, NH$_2$, OCO—(C1-C6 alkyl), OCO—(C3-C6 cycloalkyl), C1-C6 alkoxy, C1-C6 fluoroalkoxy, and cyano;

R1 is monocyclic or bicyclic heteroaryl including from 5-10 ring atoms, optionally substituted with from 1-3 $R^o$; wherein from 1-4 of the ring atoms are a heteroatom independently selected from O, N, N—H, N—$R^o$, and S;

$R^o$ is independently selected from the group consisting of: halogen; C1-C6 alkyl; fluoro(C1-C6)alkyl; hydroxyl; hydroxy($C_1$-$C_4$)alkyl; C1-C6 alkoxy; fluoro(C1-C6) alkoxy; (C1-C6 alkyl)NH—; (C1-C6 alkyl)$_2$N—; cyano; and SO$_2$—(C1-C6)alkyl;

R4 is hydrogen or halo;

R5 is hydrogen; and (i) each of R2 and R3 is hydrogen; or (ii) R2 is hydrogen, and R3 is fluoro; or (iii) R2 is a substituent other than hydrogen, and R3 is hydrogen;

(n)

X is:

(i) —Y—[C($R^a$)$_2$]$_a$-A-[C($R^b$)$_2$]$_b$—B—;

(ii) direct bond; or (iii) C=O, C($R^j$)$_2$—C(=O), C(=O)—C($R^j$)$_2$, SO$_2$—NR$^k$, NR$^k$—SO$_2$, C(=O)NR$^k$ and NR$^k$—C(=O);

R1 is C6-C10 aryl, optionally substituted with from 1-3 $R^o$;

$R^o$ is independently selected from the group consisting of: halogen; C1-C6 alkyl; fluoro(C1-C6)alkyl; hydroxyl; hydroxy($C_1$-$C_4$)alkyl; C1-C6 alkoxy; fluoro(C1-C6) alkoxy; (C1-C6 alkyl)NH—; (C1-C6 alkyl)$_2$N—; cyano; and SO$_2$—(C1-C6)alkyl;

R4 is hydrogen or halo;

R5 is hydrogen; and (i) each of R2 and R3 is hydrogen; or (ii) R2 is hydrogen, and R3 is fluoro; or (iii) R2 is a substituent other than hydrogen, and R3 is hydrogen;

(o)

X is —Y—[C($R^a$)$_2$]$_a$-A-[C($R^b$)$_2$]$_b$—B—;

R1 is C6-C10 aryl, optionally substituted with from 1-3 $R^o$;

$R^o$ is independently selected from the group consisting of: halogen; C1-C6 alkyl; fluoro(C1-C6)alkyl; hydroxyl; hydroxy($C_1$-$C_4$)alkyl; C1-C6 alkoxy; fluoro(C1-C6) alkoxy; (C1-C6 alkyl)NH—; (C1-C6 alkyl)$_2$N—; cyano; and SO$_2$—(C1-C6)alkyl;

R4 is hydrogen or halo;

R5 is hydrogen; and (i) each of R2 and R3 is hydrogen; or (ii) R2 is hydrogen, and R3 is fluoro; or (iii) R2 is a substituent other than hydrogen, and R3 is hydrogen;

(p)

X is —Y—[C($R^a$)$_2$]$_a$-A-[C($R^b$)$_2$]$_b$—B—;

R1 is C6-C10 aryl, optionally substituted with from 1-3 $R^o$;

$R^o$ is independently selected from the group consisting of: halogen; C1-C6 alkyl; fluoro(C1-C6)alkyl; hydroxyl; hydroxy($C_1$-$C_4$)alkyl; C1-C6 alkoxy; fluoro(C1-C6) alkoxy; (C1-C6 alkyl)NH—; (C1-C6 alkyl)$_2$N—; cyano; and SO$_2$—(C1-C6)alkyl;

R4 is hydrogen or halo;

R5 is hydrogen; and (i) each of R2 and R3 is hydrogen; or (ii) R2 is hydrogen, and R3 is fluoro; or (iii) R2 is a substituent other than hydrogen, and R3 is hydrogen;

(q)

X is —Y—[C($R^a$)$_2$]$_a$-A-[C($R^b$)$_2$]$_b$—B—, and Y is a bond;

R1 is C6-C10 aryl, optionally substituted with from 1-3 $R^o$;

$R^o$ is independently selected from the group consisting of: halogen; C1-C6 alkyl; fluoro(C1-C6)alkyl; hydroxyl; hydroxy($C_1$-$C_4$)alkyl; C1-C6 alkoxy; fluoro(C1-C6) alkoxy; (C1-C6 alkyl)NH—; (C1-C6 alkyl)$_2$N—; cyano; and SO$_2$—(C1-C6)alkyl;

R4 is hydrogen or halo;

R5 is hydrogen; and (i) each of R2 and R3 is hydrogen; or (ii) R2 is hydrogen, and R3 is fluoro; or (iii) R2 is a substituent other than hydrogen, and R3 is hydrogen; or (r)

X is —Y—[C($R^a$)$_2$]$_a$-A-[C($R^b$)$_2$]$_b$—B—, Y is a bond, and each occurrence of $R^a$ and $R^b$ is independently selected from H, F, OH, C1-C6 alkyl, C3-C6 cycloalkyl, NH$_2$, OCO—(C1-C6 alkyl), OCO—(C3-C6 cycloalkyl), C1-C6 alkoxy, C1-C6 fluoroalkoxy, and cyano;

R1 is C6-C10 aryl, optionally substituted with from 1-3 $R^o$;

$R^o$ independently selected from the group consisting of: halogen; C1-C6 alkyl; fluoro(C1-C6)alkyl; hydroxyl; hydroxy($C_1$-$C_4$)alkyl; C1-C6 alkoxy; fluoro(C1-C6) alkoxy; (C1-C6 alkyl)NH—; (C1-C6 alkyl)$_2$N—; cyano; and SO$_2$—(C1-C6)alkyl;

R4 is hydrogen or halo;

R5 is hydrogen; and (i) each of R2 and R3 is hydrogen; or (ii) R2 is hydrogen, and R3 is fluoro; or (iii) R2 is a substituent other than hydrogen, and R3 is hydrogen.

Embodiments can include any one or more of the following features.

The compound or salt according can have formula (Ia):

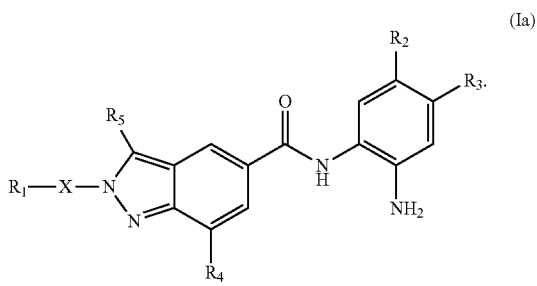

The compound or salt can have formula (Ib):

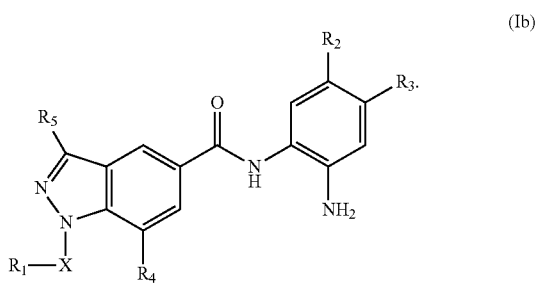

A can be a bond.

Each occurrence of $R^a$ and $R^b$ (when present) can be independently selected from H, F, C1-C6 alkyl, and C3-C6 cycloalkyl.

Each occurrence of $R^a$ and $R^b$ (when present) can be H.
a can be 1.
b can be 0.
a can be 1, and b can be 0. In embodiments, X can be $CH_2$.
b is 1, 2, or 3. In embodiments, a can also be 1; e.g., X can be $(CH_2)_{2-4}$.

R1 can be C3-C10 cycloalkyl, which is optionally substituted with from 1-3 $R^o$; e.g., R1 can be C3-C6 cycloalkyl, which is optionally substituted with from 1-3 $R^o$; e.g., R1 can be cyclopropyl, which is optionally substituted with from 1-3 $R^o$; e.g., R1 can be unsubstituted C3-C6 cycloalkyl; e.g., R1 can be unsubstituted cyclopropyl.

In various embodiments, the compound has a structure of formula (Ia) and —X—$R_1$ is $CH_2$phenyl, and the phenyl is optionally substituted with one or more substituents selected from halo (e.g., fluoro) and methyl. In some embodiments, —$XR_1$ is $CH_2$pyridyl, and the pyridyl is optionally substituted with one or more substituents selected from halo (e.g., fluoro) and methyl. In some embodiments, —$XR_1$ is $CH_2$cycloalkyl (e.g., cyclopropyl, cyclopentyl, or cyclohexyl). In some cases, —$XR_1$ is $CH_2$cyclopropyl. The cycloalkyl can optionally be substituted with one or more of C1-C3alkyl, C1-C3alkoxy, and halo. In some embodiments, —$XR_1$ is $CH_2$pyrazolyl, and the pyrazolyl is optionally substituted with one or more substituents selected from methyl and halo (e.g., fluoro). In various embodiments, $R_2$ and $R_3$ are each hydrogen. In some embodiments, $R_2$ is hydrogen and $R_3$ is halo (e.g., fluoro). In various embodiments, $R_4$ is hydrogen.

In various embodiments, the compound has a structure of formula (Ib) and —X—$R_1$ is $CH_2$phenyl, and the phenyl is optionally substituted with one or more substituents selected from halo (e.g., fluoro) and methyl. In some embodiments, —$XR_1$ is $CH_2$pyridyl, and the pyridyl is optionally substituted with one or more substituents selected from halo (e.g., fluoro) and methyl. In some embodiments, —$XR_1$ is $CH_2$cycloalkyl (e.g., cyclopropyl, cyclopentyl, or cyclohexyl). In some cases, —$XR_1$ is $CH_2$cyclopropyl. The cycloalkyl can optionally be substituted with one or more of C1-C3alkyl, C1-C3alkoxy, and halo. In some embodiments, —$XR_1$ is $CH_2$pyrazolyl, and the pyrazolyl is optionally substituted with one or more substituents selected from methyl and halo (e.g., fluoro). In various embodiments, $R_2$ and $R_3$ are each hydrogen. In some embodiments, $R_2$ is hydrogen and $R_3$ is halo (e.g., fluoro). In various embodiments, $R_4$ is hydrogen.

In some embodiments, the compound or salt disclosed herein can have a structure of formula (2a):

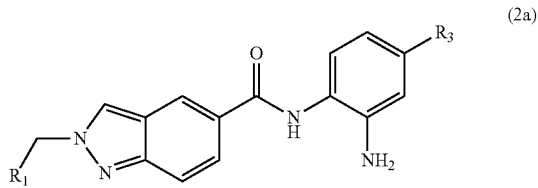

wherein:
R1 is C3-C6 cycloalkyl, phenyl, or heteroaryl with 5-6 ring atoms, wherein R1 is optionally substituted with 1-3 groups independently selected from Cl, F, and C1-C4 alkyl; and
R3 is H or F.

In other embodiments for compounds of formula (2a), R1 is cyclopropyl, phenyl, or heteroaryl with 5-6 ring atoms and 1-2 N atoms, wherein the phenyl and heteroaryl are optionally substituted with 1-2 groups independently selected from F, and C1-C4 alkyl. In further embodiments, R1 is cyclopropyl, phenyl, pyridyl, or pyrazolyl, wherein the phenyl, pyridyl and pyrazolyl groups are optionally substituted with 1-2 groups independently selected from F, and C1-C4 alkyl.

In various embodiments, the compound or salt disclosed herein has a structure of formula (2b):

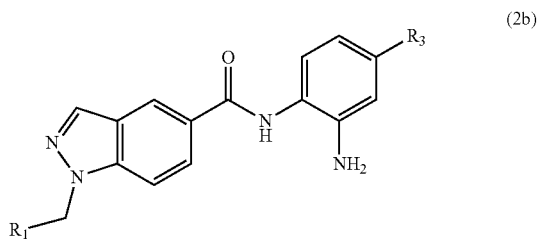

wherein:
R1 is C3-C6 cycloalkyl, phenyl, or heteroaryl with 5-6 ring atoms, wherein R1 is optionally substituted with 1-3 groups independently selected from Cl, F, and C1-C4 alkyl; and
R3 is H or F.

In other embodiments for compounds of formula (2b), R1 is cyclopropyl, phenyl, or heteroaryl with 5-6 ring atoms and 1-2 N atoms, wherein the phenyl and heteroaryl are optionally substituted with 1-2 groups independently selected from F, and C1-C4 alkyl. In further embodiments, R1 is cyclopropyl, phenyl, pyridyl, or pyrazolyl, wherein the phenyl, pyridyl and pyrazolyl groups are optionally substituted with 1-2 groups independently selected from F, and C1-C4 alkyl.

In some embodiments, the compound is one or more of those delineated in Table 1 below. In some embodiments, the compound is one selected from A1-A16 and A24. In some embodiments, the compound is one selected from A1-A16. In some embodiments, the compound is selected from A6-A8, A10, A12, and A24. In some embodiments, the compound is selected from A6-A8, A10, and A12. In some embodiments, the compound is selected from A1, A4-A8, and A13-A15. In some embodiments, the compound is selected from A2, A3, A9, and A10.

TABLE 1

A1
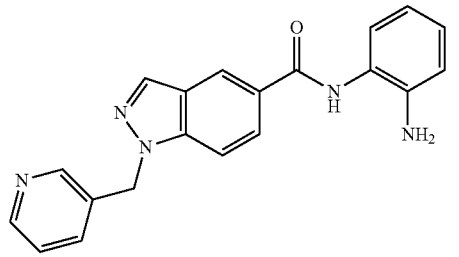 [SMILES: Nc1ccccc1NC(=O)c1ccc2c(cnn2Cc2cccnc2)c1]

A2
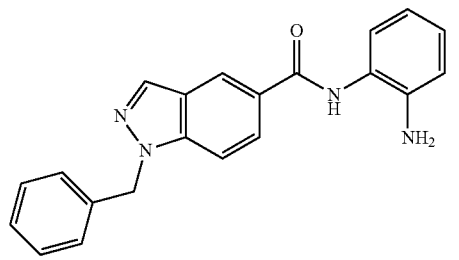 [SMILES: Nc1ccccc1NC(=O)c1ccc2c(cnn2Cc2ccccc2)c1]

A3
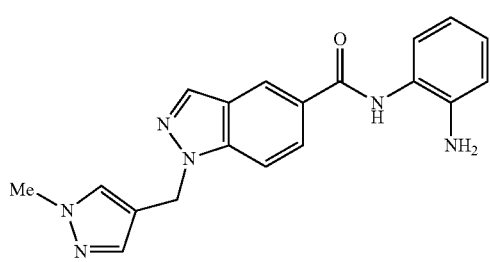 [SMILES: Cn1cc(Cn2ncc3cc(C(=O)Nc4ccccc4N)ccc32)cn1]

A4
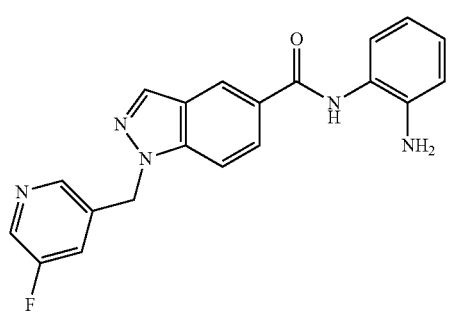 [SMILES: Nc1ccccc1NC(=O)c1ccc2c(cnn2Cc2cncc(F)c2)c1]

TABLE 1-continued

A5
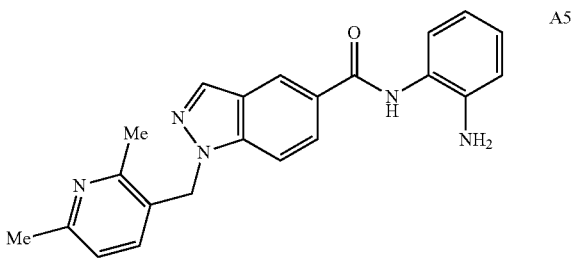

A6
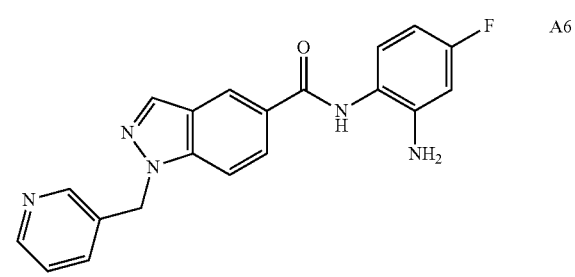

A7
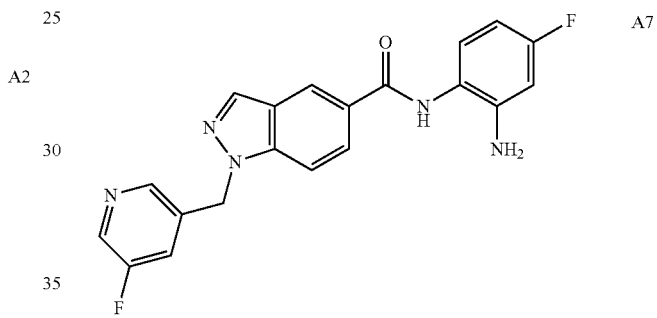

A8
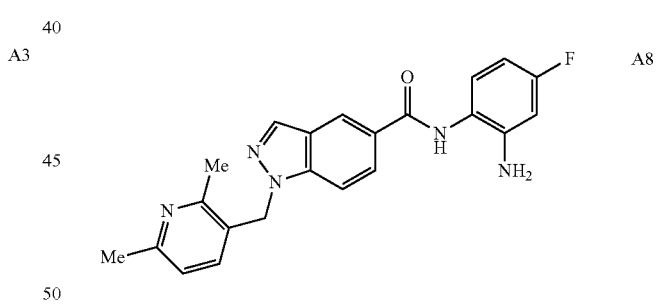

A9
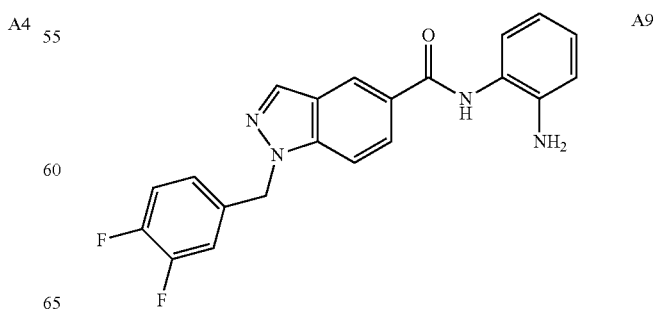

TABLE 1-continued
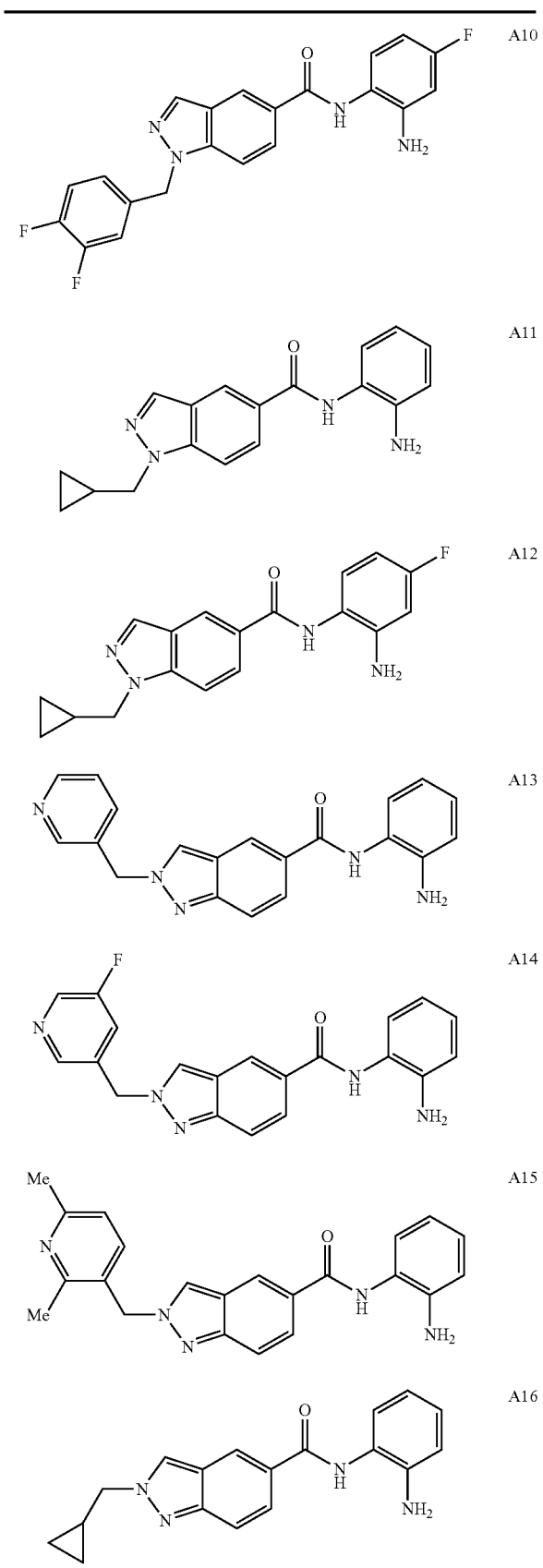
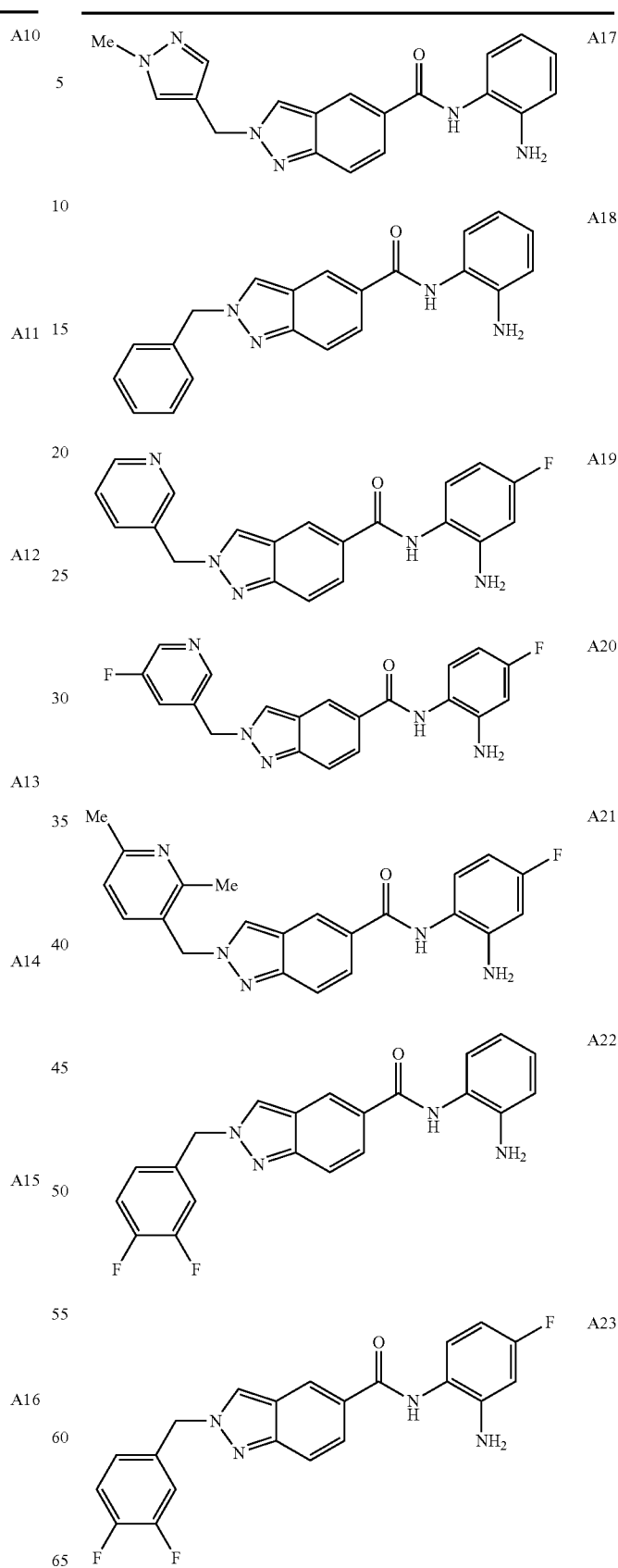

TABLE 1-continued

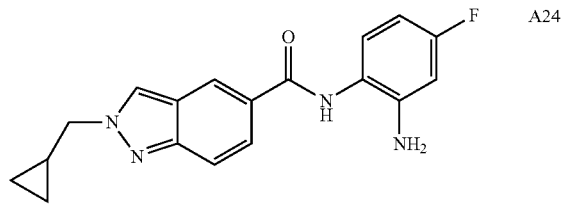

A24

II. Compound Forms

Compounds of formula (I) described herein may contain one or more asymmetric centers and thus occur as racemates and racemic mixtures, single enantiomers, individual diastereomers and diastereomeric mixtures. While shown without respect to the stereochemistry in formula (I), compounds disclosed herein include optical isomers enantiomers and diastereomers; as well as the racemic and resolved, enantiomerically pure stereoisomers; as well as other mixtures of the stereoisomers and pharmaceutically acceptable salts thereof. The use of these compounds is intended to cover the racemic mixture or either of the chiral stereoisomers.

Compounds of formula (I) described herein may also contain linkages (e.g., carbon-carbon bonds, carbon-nitrogen bonds such as amide bonds) wherein bond rotation is restricted about that particular linkage, e.g. restriction resulting from the presence of a ring or double bond. Accordingly, all cis/trans and E/Z isomers and rotational isomers are expressly included herein.

One skilled in the art will also recognize that it is possible for tautomers to exist for the compounds described herein. Contemplated are all such tautomers even though not shown in the formulas herein. All such isomeric forms of such compounds are expressly included herein.

Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in their entireties. It is also understood that this disclosure contemplated all possible regio-isomers, and mixtures thereof, which can be obtained in pure form by standard separation procedures known to those skilled in the art, and include, but are not limited to, column chromatography, thin-layer chromatography, and high-performance liquid chromatography, for all compounds disclosed herein (e.g., compounds of formula (1), (1a), (1b), (2a) and (2b)).

The compounds described herein also include the various hydrate and solvate forms of the compounds.

Compounds described herein can also include all isotopes of atoms occurring in the intermediates or final compounds. Isotopes include those atoms having the same atomic number but different mass numbers. For example, isotopes of hydrogen include tritium and deuterium.

The compounds described herein also include pharmaceutically acceptable salts of the compounds disclosed herein. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient. Pharmaceutically acceptable salts, including mono- and bi-salts, include, but are not limited to, those derived from organic and inorganic acids such as, but not limited to, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8] each of which is incorporated herein by reference in their entireties.

In some embodiments, the compounds are prodrugs. As used herein, "prodrug" refers to a moiety that releases a compound described herein when administered to a patient. Prodrugs can be prepared by modifying functional groups present in the compounds in such a way that the modifications are cleaved, either in routine manipulation or in vivo, to the parent compounds. Examples of prodrugs include compounds as described herein that contain one or more molecular moieties appended to a hydroxyl, amino, sulfhydryl, or carboxyl group of the compound, and that when administered to a patient, cleave in vivo to form the free hydroxyl, amino, sulfhydryl, or carboxyl group, respectively. Examples of prodrugs include, but are not limited to, acetate, formate and benzoate derivatives of alcohol and amine functional groups in the compounds described herein. Preparation and use of prodrugs is discussed in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference in their entireties.

III. Synthesis of Compounds of Formula (I)

The compounds described herein can be prepared in a variety of ways known to one skilled in the art of organic synthesis. The compounds described herein can be synthesized using the methods as hereinafter described below, together with synthetic methods known in the art of synthetic organic chemistry or variations thereon as appreciated by those skilled in the art.

In some embodiments, the compounds described herein can be prepared using the starting materials indicated in Table 2 below and the appropriately substituted indazole.

TABLE 2

| Compound | R-X or aldehyde | diamine | MS | NMR |
|---|---|---|---|---|
| A1 | 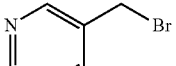 | 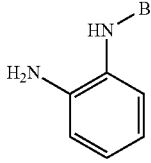 | ES+ (M + H)+ 344 | 1H NMR (DMSO-d6) δ: 10.60 (s, 1H), 8.83 (s, 1H), 8.78 (m, 1H), 8.65 (s, 1H), 8.37 (s, 1H), 8.17 (d, J = 8.7 Hz, 2H), 7.97 (d, J = 8.7, 1H), 7.86 (m, 1H), 7.58 (d. J = 8.1 Hz, 1H), 7.46 (d, J = 7.5 Hz, 1H), 7.4-7.3 (m, 2H), 5.93 (s, 2H) |
| A2 | 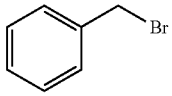 | 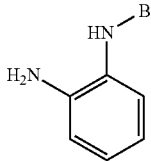 | ES+ (M + H)+ 343 | 1H NMR (DMSO-d6) δ: 10.34 (br. s, 1H), 8.56 (s, 1H), 8.31 (s, 1H), 8.04 (d, J = 9 Hz, 1H), 7.84 (d, J = 9 Hz, 1H), 7.44 (br. d, 1H), 7.35-7.15 (m, 8H), 5.72 (s, 2H) |
| A3 | 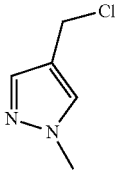 | 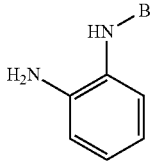 | ES+ (M + H)+ 347 | 1H NMR (DMSO-d6) δ: 10.60 (s, 1H), 8.60 (s, 1H), 8.24 (s, 1H), 8.11 (d, J = 9 Hz, 1H), 7.89 (d, J = 9 Hz, 1H), 7.68 (s, 1H), 7.58 (br. d, J = 7.8, 1H), 7.5-7.3 (m, 4H), 5.53 (s, 2H), 3.73 (s, 3H) |
| A4 | 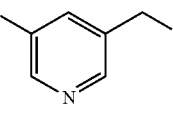 | 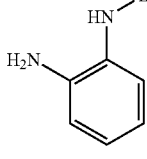 | ES+ (M + H)+ 362 | 1H NMR (CD3OD) δ: 8.72 (br. s, 1H), 8.63 (m, 1H), 8.58 (s, 1H), 8.34 (s, 1H), 8.17 (dd, J = 9, 1.5 Hz, 1H), 7.90 (m, 1H), 7.85 (d. J = 9 Hz, 1H), 7.6-7.4 (m, 4H), 5.92 (s, 2H) |
| A5 | 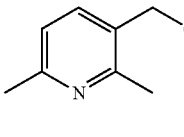 | 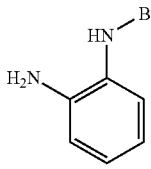 | ES+ (M + H)+ 372 | 1H NMR (CD3OD) δ: 8.65 (s, 1H), 8.33 (br. s, 1H), 8.18 (d, J = 8.7 Hz, 1H), 7.90 (2 d, J = 8.7, 8.1 Hz, 2H), 7.66 (d. J = 8.1 Hz, 1H), 7.6-7.4 (m, 4H), 5.91 (s, 2H), 2.86 (s, 3H), 2.74 (s, 3H) |
| A6 | 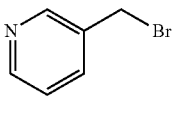 | 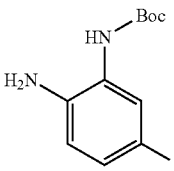 | ES+ (M + H)+ 362 | 1H NMR (CD3OD) δ: 8.88 (s, 1H), 8.83 (d, J = 5.7 Hz, 1H), 8.61 (s, 1H), 8.52 (d, J = 8.1 Hz, 1H), 8.34 (s, 1H), 8.16 (dd, J = 8.7, 1.5 Hz, 1H), 8.08 (dd, J = 8.1, 6 Hz, 1H), 7.87 (d. J = 8.7 Hz, 1H), 7.46 (m, 1H), 7.18 (m, 2H), 5.99 (s, 2H) |
| A7 | 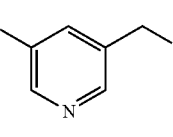 | 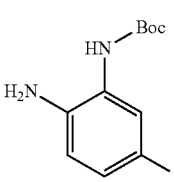 | ES+ (M + H)+ 380 | 1H NMR (CD3OD) δ: 8.71 (br. s, 1H), 8.62 (m, 1H), 8.57 (s, 1H), 8.33 (s, 1H), 8.15 (dd, J = 8.7, 1.5 Hz, 1H), 7.99 (br. m, 1H), 7.83 (d. J = 8.7 Hz, 1H), 7.53 (m, 1H), 7.38-7.24 (m, 2H), 5.91 (s, 2H) |

TABLE 2-continued

| Compound | R-X or aldehyde | diamine | MS | NMR |
|---|---|---|---|---|
| A8 | 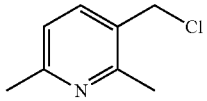 | 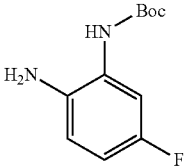 [SMILES: CC(C)(C)OC(=O)Nc1cc(F)ccc1N] | ES⁺ (M + H)⁺ 390 | ¹H NMR (CD₃OD) δ: 8.62 (s, 1H), 8.32 (s, 1H), 8.16 (dd, J = 9, 1.5 Hz, 1H), 7.92 (d, J = 8.1 Hz, 1H), 7.84 (d, J = 8.4 Hz, 1H), 7.66 (d. J = 8.4 Hz, 1H), 7.48 (br. m, 1H), 7.21 (br. m, 2H), 5.90 (s, 2H), 2.86 (s, 3H), 2.75 (s, 3H) |
| A9 | 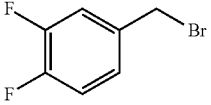 | 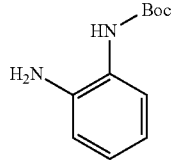 | ES⁺ (M + H)⁺ 379 | ¹H NMR (CD₃OD) δ: 8.60 (m, 1H), 8.28 (s, 1H), 8.11 (dd, J = 9, 1.5 Hz, 1H), 7.73 (d, J = 9 Hz, 1H), 7.6-7.4 (m, 4H), 7.3-7.0 (m, 3H), 5.69 (s, 2H) |
| A10 | 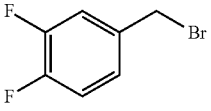 | 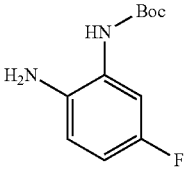 [SMILES: CC(C)(C)OC(=O)Nc1cc(F)ccc1N] | ES⁺ (M + H)⁺ 397 | ¹H NMR (CD₃OD) δ: 8.58 (m, 1H), 8.27 (s, 1H), 8.09 (dd, J = 9, 1.5 Hz, 1H), 7.72 (d, J = 9 Hz, 1H), 7.48 (br. dd, 1H), 7.3-7.0 (m, 5H), 5.69 (s, 2H) |
| A11 | 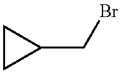 | 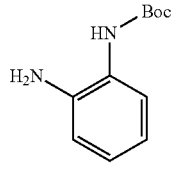 | ES⁺ (M + H)⁺ 307 | ¹H NMR (DMSO-d₆) δ: 10.59 (s, 1H), 8.60-8.65 (m, 1H), 8.27 (d, J = 0.8 Hz, 1H), 8.11 (dd, J = 8.8, 1.6 Hz, 1H), 7.85 (d, J = 8.9 Hz, 1H), 7.33-7.62 (m, 4H), 4.37 (d, J = 7.0 Hz, 2H), 1.25-1.36 (m, 1H), 0.47-0.54 (m, 2H), 0.38-0.44 (m, 2H) |
| A12 | 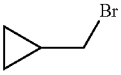 | 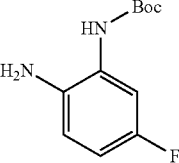 [SMILES: CC(C)(C)OC(=O)Nc1cc(F)ccc1N] | ES⁺ (M + H)⁺ 325 | ¹H NMR (CD₃OD) δ: 8.57 (s, 1H), 8.21 (s, 1H), 8.10 (dd, J = 9, 1.5 Hz, 1H), 7.75 (d, J = 9 Hz, 1H), 7.52 (dd, J = 9, 5.1 Hz, 1H), 7.35-7.25 (m, 2H), 4.38 (d, J = 6.9 Hz, 2H), 1.35 (m, 1H), 0.57 (m, 2H), 0.45 (m, 2H) |
| A13 | 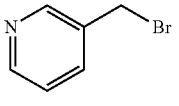 | 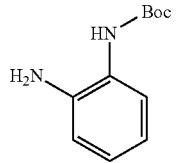 | ES⁺ (M + H)⁺ 344 | ¹H NMR (DMSO-d₆) δ: 10.59 (s, 1H), 8.96 (br. s, 1H), 8.89 (s, 1H), 8.84 (br. d, 1H), 8.71 (s, 1H), 8.41 (br. d, 1H), 7.96 (dd, 1H), 7.91 (d, J = 9 Hz, 1H), 7.68 (d. J = 9 Hz, 1H), 7.61 (d, J = 7.8 Hz, 1H), 7.50 (d, J = 7.8 Hz, 1H), 7.42 (t, J = 7.8 Hz, 1H), 7.33 (t, J = 7.8 Hz, 1H), 5.94 (s, 2H) |
| A14 | 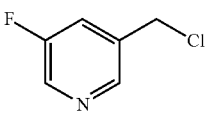 | 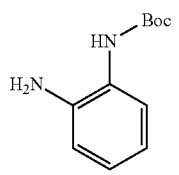 | ES⁺ (M + H)⁺ 362 | ¹H NMR (CD₃OD) δ: 8.76 (s, 2H), 8.67 (s, 1H), 8.62 (m, 1H), 8.09 (m, 1H), 7.98 (dd, J = 9, 1.5 Hz, 1H), 7.74 (d, J = 9 Hz, 1H), 7.6-7.4 (m, 4H), 5.92 (s, 2H) |

TABLE 2-continued

| Compound | R-X or aldehyde | diamine | MS | NMR |
|---|---|---|---|---|
| A15 | | H₂N-C₆H₄-NH-Boc | ES⁺ (M + H)⁺ 372 | ¹H NMR (CD₃OD) δ: 8.77 (s, 1H), 8.63 (dd, J = 1.8, 0.9 Hz, 1H), 8.14 (d, J = 8.4 Hz, 1H), 7.97 (dd, J = 9, 1.8 Hz, 1H), 7.71 (2 d, J = 9, 8.4 Hz, 2H), 7.6-7.4 (m, 4H), 5.96 (s, 2H), 2.87 (s, 3H), 2.76 (s, 3H) |
| A16 | cyclopropylmethyl-Br | H₂N-C₆H₄-NH-Boc | ES⁺ (M + H)⁺ 307 | ¹H NMR (DMSO-d₆) δ: 10.61 (s, 1H), 8.70 (dd, J = 1.6, 0.8 Hz, 1H), 8.69 (d, J = 0.7 Hz, 1H), 7.93 (dd, J = 9.1, 1.7 Hz, 1H), 7.71 (d, J = 9.0 Hz, 1H), 7.34-7.67 (m, 4H), 4.34 (d, J = 7.3 Hz, 2H), 1.38-1.48 (m, 1H), 0.56-0.61 (m, 2H), 0.45-0.50 (m, 2H) |

Compounds described herein can be conveniently prepared in accordance with the procedures outlined in the Examples section, from commercially available starting materials, compounds known in the literature, or readily prepared intermediates, by employing conventional synthetic methods and procedures known to those skilled in the art. Conventional synthetic methods and procedures for the preparation of organic molecules and functional group transformations and manipulations can be readily obtained from the relevant scientific literature or from standard textbooks in the field. It will be appreciated that, where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds described herein.

Synthetic chemistry transformations useful in synthesizing the compounds described herein are known in the art and include, for example, those such as described in R. C. Larock, *Comprehensive Organic Transformations*, 2d.ed., Wiley-VCH Publishers (1999); P. G. M. Wuts and T. W. Greene, *Protective Groups in Organic Synthesis*, 4th Ed., John Wiley and Sons (2007); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof. Preparation of compounds can involve the protection and deprotection of various chemical groups. The need for protection and deprotection, and the selection of appropriate protecting groups can be readily determined by one skilled in the art. The chemistry of protecting groups can be found, for example, in Wuts P G M and Greene T W, 2006, Greene's Protective Groups in Organic Synthesis, Fourth Edition, John Wiley & Sons, Inc., Hoboken, N.J., USA, which is incorporated herein by reference in its entirety. Adjustments to the protecting groups and formation and cleavage methods described herein may be adjusted as necessary in light of the various substituents.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent freezing temperature to the solvent boiling temperature. A given reaction can be carried out in one solvent or a mixture of more than one solvent. Depending on the particular reaction step, suitable solvents for a particular reaction step can be selected.

The processes described herein can be monitored according to any suitable method known in the art. For example, product formation can be monitored by spectroscopic means, such as nuclear magnetic resonance spectroscopy (e.g., ¹H and/or ¹³C NMR) infrared spectroscopy, spectrophotometry (e.g., UV-visible), or mass spectrometry, or by chromatography such as high performance liquid chromatography (HPLC) or thin layer chromatography.

The compounds described herein can be separated from a reaction mixture and further purified by a method such as column chromatography, high-performance liquid chromatography (HPLC), or recrystallization.

One of skill in the art will recognize that there are additional methods of producing the compounds of formula (I) in addition to those described in the Examples section.

IV. Use

A histone deacetylase (HDAC), as described herein, can be any polypeptide having features characteristic of polypeptides that catalyze the removal of the acetyl group (deacetylation) from acetylated target proteins. Features characteristic of HDACs are known in the art (see, for example, Finnin et al., 1999, Nature, 401:188). Thus, an HDAC can be a polypeptide that represses gene transcription by deacetylating the ε-amino groups of conserved lysine residues located at the N-termini of histones, e.g., H3, H4, H2A, and H2B, which form the nucleosome. HDACs also deacetylate other proteins such as p53, E2F, α-tubulin, and MyoD (see, for example, Annemieke et al., 2003, Biochem. J., 370:737). HDACs can also be localized to the nucleus and certain HDACs can be found in both the nucleus and also the cytoplasm.

Compounds of formula (I) described herein may interact with any HDAC. In some embodiments, the compounds of formula (I) described herein will have at least about 2-fold (e.g., at least about 5-fold, 10-fold, 15-fold, or 20-fold) greater activity to inhibit one or more class I HDACS (e.g., HDAC1, HDAC2, or HDAC3) as compared to one or more other HDACs (e.g., one or more HDACs of class IIa, IIb, or IV).

In various embodiments, the compound of formula (I) is selective for HDAC 1, compared to HDAC2 and HDAC3. In various embodiments, the compound of formula (I) is selective for HDAC 2, compared to HDAC1 and HDAC3. In various embodiments, the compound of formula (I) is selective for HDAC 3, compared to HDAC1 and HDAC2. In various embodiments, the compound of formula (I) is selective for HDAC1 and HDAC2, compared to HDAC3. In various embodiments, the compound of formula (I) is selective for HDAC1 and HDAC3, compared to HDAC2. In various embodiments, the compound of formula (I) is selective for HDAC2 and HDAC3, compared to HDAC1.

One aspect features a method of treating a cancer in patient in need thereof, comprising administering a therapeutically effective amount of an HDAC inhibitor as described herein, or pharmaceutically, acceptable salt thereof. In some embodiments, the cancer is a solid tumor, neoplasm, carcinoma, sarcoma, leukemia, or lymphoma. In some embodiments, leukemias include acute leukemias and chronic leukemias such as acute lymphocytic leukemia (ALL), B-cell acute lymphoblastic leukemia (B-ALL), acute myeloid leukemia, chronic lymphocytic leukemia (CLL), chronic myelogenous leukemia (CML) and Hairy Cell Leukemia; lymphomas such as cutaneous T-cell lymphomas (CTCL), noncutaneous peripheral T-cell lymphomas, lymphomas associated with human T-cell lymphotrophic virus (fTLV) such as adult T-cell leukemia/lymphoma (ATLL), Hodgkin's disease and non-Hodgkin's lymphomas, large-cell lymphomas, diffuse large B-cell lymphoma (DLBCL); Burkitt's lymphoma; primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genitor-urinary cancers (e.g., prostate, bladder, renal, uterine, ovarian, testicular, rectal and colon), lung cancer, breast cancer.

In some embodiments, the cancer is (a) Cardiac: sarcoma (angiosarcoma, fibrosarcoma, rhabdomyosarcoma, liposarcoma), myxoma, rhabdomyoma, fibroma, lipoma and teratoma; (b) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; (c) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); (d) Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (e) Liver: hepatoma (hepatocellular carcinoma), cholangiocarcinoma, hepatoblastoma, angiosarcoma, hepatocellular adenoma, hemangioma; (f) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors; (g) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord (neurofibroma, meningioma, glioma, sarcoma); (h) Gynecological: uterus (endometrial carcinoma), cervix (cervical carcinoma, pre-tumor cervical dysplasia), ovaries (ovarian carcinoma, serous cystadenocarcinoma, mucinous cystadenocarcinoma), unclassified carcinoma (granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma), embryonal rhabdomyosarcoma, fallopian tubes (carcinoma); (i) Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); (j) Skin: malignant melanoma, basal cell carcinoma, squamous cell carcinoma, Karposi's sarcoma, moles dysplastic nevi, lipoma, angioma, dermatofibroma, keloids, psoriasis; and (k) Adrenal glands: neuroblastoma conditions.

In another aspect, provided is a method of treating an inflammatory disorder in patient in need thereof, comprising administering a therapeutically effective amount of a compound of formula (I) as described herein, or pharmaceutically, acceptable salt thereof. In some embodiments, the inflammatory disorder is an acute and chronic inflammatory disease, autoimmune disease, allergic disease, disease associated with oxidative stress, and diseases characterized by cellular hyperproliferation. Non-limiting examples are inflammatory conditions of a joint including rheumatoid arthritis (RA) and psoriatic arthritis; inflammatory bowel diseases such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs, ischemic injury, including cerebral ischemia (e.g., brain injury as a result of trauma, epilepsy, hemorrhage or stroke, each of which may lead to neurodegeneration); HIV, heart failure, chronic, acute or malignant liver disease, autoimmune thyroiditis; systemic lupus erythematosus, Sjorgren's syndrome, lung diseases (e.g., ARDS); acute pancreatitis; amyotrophic lateral sclerosis (ALS); Alzheimer's disease; cachexia/anorexia; asthma; atherosclerosis; chronic fatigue syndrome, fever; diabetes (e.g., insulin diabetes or juvenile onset diabetes); glomerulonephritis; graft versus host rejection (e.g., in transplantation); hemorrhagic shock; hyperalgesia: inflammatory bowel disease; multiple sclerosis; myopathies (e.g., muscle protein metabolism, esp. in sepsis); osteoarthritis; osteoporosis; Parkinson's disease; pain; pre-term labor; psoriasis; reperfusion injury; cytokine-induced toxicity (e.g., septic shock, endotoxic shock); side effects from radiation therapy, temporal mandibular joint disease, tumor metastasis; or an inflammatory condition resulting from strain, sprain, cartilage damage, trauma such as burn, orthopedic surgery, infection or other disease processes.

Allergic diseases and conditions, include but are not limited to respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies, and the like.

In another aspect, provided is a method of preventing or treating a memory-related disorder in patient in need thereof, comprising administering a therapeutically effective amount of a compound of formula (I) as described herein, or pharmaceutically, acceptable salt thereof. Compounds of formula (I) can be used to treat patients with memory impairments associated with direct cognitive disorders such as amnesia, dementia and delirium; anxiety disorders such as phobias, panic disorders, psychosocial stress (e.g. as seen in disaster, catastrophe or violence victims), obsessive-compulsive disorder, generalized anxiety disorder and post-traumatic stress disorder; mood disorders such as depression and bipolar disorder; and psychotic disorders such as schizophrenia and delusional disorder. Memory impairment, a hallmark of neurodegenerative diseases such as, but not limited to, Parkinson's, Alzheimer's, Huntington's, amyotrophic lateral sclerosis (ALS), spinocerebellar ataxia, as well as aging, can also be treated by using compounds of formula (I). In addition, compounds as disclosed herein can be used to treat drug addiction through extinction of drug-seeking behavior.

In another aspect, the present disclosure provides a method of preventing or treating a hemoglobin disorder in patient in need thereof, comprising administering a therapeutically effective amount of a compound of formula (I) as described herein, or pharmaceutically, acceptable salt thereof. Compounds of formula (I) can be used to treat patients with sickle cell anemia or β-thalassemia. In various cases, the compound is a selective HDAC 1 and/or HDAC 2 inhibitor and is used to prevent or treat the hemoglobin disorder (e.g., sickle cell anemia or β-thalassemia).

In a further aspect, this application features methods of treating a neurological condition (e.g., Friedreich's ataxia (FRDA), myotonic dystrophy, spinal muscular atrophy, fragile X syndrome, Huntington's disease, a spinocerebellar ataxia, Kennedy's disease, amyotrophic lateral sclerosis, Niemann Pick, Pitt Hopkins disease, spinal and bulbar muscular atrophy, Alzheimer's disease or schizophrenia, bipolar disorder, and related diseases) that include administering a compound of formula (I) described herein to a patient having a neurological condition.

In another aspect, this application features the use of a compound of formula (I) described herein in the preparation of a medicament for the treatment or prevention of a neurological condition (e.g., Friedreich's ataxia, myotonic dystrophy, spinal muscular atrophy, fragile X syndrome, Huntington's disease, a spinocerebellar ataxia, Kennedy's disease, amyotrophic lateral sclerosis, Niemann Pick, Pitt Hopkins disease, spinal and bulbar muscular atrophy, or Alzheimer's disease); a memory-affecting condition or disease, a cancer; or an inflammatory disorder, or a *Plasmodium falciparum* infection (e.g., malaria).

In a further aspect, the application provides a kit for the treatment or prevention of a disorder selected from a neurological disorder (e.g., Friedreich's ataxia, myotonic dystrophy, spinal muscular atrophy, fragile X syndrome, Huntington's disease, a spinocerebellar ataxia, Kennedy's disease, amyotrophic lateral sclerosis, spinal and bulbar muscular atrophy, or Alzheimer's disease), a memory-affecting condition or disease, a cancer, an inflammatory disorder, or a *Plasmodium falciparum* infection (e.g., malaria) in a patient in need thereof, comprising (i) a compound of formula (I) described herein or a pharmaceutically acceptable salt thereof; and (ii) instructions comprising a direction to administer said compound to said patient.

In some embodiments of the above methods, the methods further include assaying the activity of the candidate compound to increase expression of one or more genes whose expression is decreased in the neurological condition (e.g., frataxin, huntingtin, brain derived neurotrophic factor (BDNF), peroxisome proliferator-activated receptor-gamma, coactivator 1, alpha (PGC1A), ataxin, fragile X mental retardation (FMR1), dystrophia myotonica protein kinase (DMPK), or androgen receptor). In some embodiments, the activity of the candidate compound to increase expression of one or more genes whose expression is decreased in the neurological condition is measured in an animal, e.g., an animal model of the neurological condition.

In some embodiments of the above methods, the method is repeated for a plurality of test compounds (e.g., at least 10, 20, 50, 100, 200, 500, or 1000 test compounds).

In another aspect, this application features methods of treating a neurological condition (e.g., Friedreich's ataxia, myotonic dystrophy, spinal muscular atrophy, fragile X syndrome, Huntington's disease, spinocerebellar ataxias, Kennedy's disease, amyotrophic lateral sclerosis, spinal and bulbar muscular atrophy, or Alzheimer's disease) that include performing any of the above methods, formulating the candidate compound in a pharmaceutical composition, and administering the pharmaceutical composition to a patient having a neurological condition.

HDAC inhibitors have been shown to have antimalarial activity (Andrews et al., 2000, Int. J. Parasitol., 30:761-768; Andrews et al., Antimicrob. Agents Chemother., 52:1454-61). Certain embodiments include methods of treating a *Plasmodium falciparum* infection (e.g., malaria) in a patient in need thereof.

HDAC inhibitors may also be useful to treat infectious disease such as viral infections. For example, treatment of HIV infected cells with HDAC inhibitors and anti-retroviral drugs can eradicate virus from treated cells (Blazkova j et al J Infect Dis. 2012 Sep. 1; 206(5):765-9; Archin N M et al Nature 2012 Jul. 25, 487(7408):482-5). Certain embodiments include methods of treating a HIV infection in subjects in need thereof.

V. Pharmaceutical Compositions

HDAC inhibitors can be administered neat or formulated as pharmaceutical compositions. Pharmaceutical compositions include an appropriate amount of the HDAC inhibitor in combination with an appropriate carrier and optionally other useful ingredients.

Acceptable salts of the formula (I) compounds described herein include, but are not limited to, those prepared from the following acids: alkyl, alkenyl, aryl, alkylaryl and alkenylaryl mono-, di- and tricarboxylic acids of 1 to 20 carbon atoms, optionally substituted by 1 to 4 hydroxyls; alkyl, alkenyl, aryl, alkylaryl and alkenylaryl mono-, di- and trisulfonic acids of 1 to 20 carbon atoms, optionally substituted by 1 to 4 hydroxyls; dibasic acids and mineral acids. Examples include hydrochloric; hydrobromic; sulfuric; nitric; phosphoric; lactic (including (+)-L-lactic, (+/−)-DL-lactic); fumaric; glutaric; maleic; acetic; salicyclic; p-toluenesulfonic; tartaric (including (+)-L-tartaric); citric; methanesulfonic; formic; malonic; succinic; naphthalene-2-sulfonic; and benzenesulfonic acids. Also, pharmaceutically-acceptable salts can be prepared as amine salts, ammonium salts, or alkaline metal or alkaline earth salts, such as sodium, potassium or calcium salts of the carboxylic acid group. These are formed from alkaline metal or alkaline earth metal bases or from amine compounds.

Pharmaceutical compositions of formula (I) compounds described herein suitable for oral administration can be in the form of (1) discrete units such as capsules, sachets, tablets, or lozenges each containing a predetermined amount of the HDAC inhibitor; (2) a powder or granules; (3) a bolus, electuary, or paste; (4) a solution or a suspension in an aqueous liquid or a non-aqueous liquid; or (5) an oil-in-water liquid emulsion or a water-in-oil liquid emulsion. Compositions suitable for topical administration in the mouth, for example buccally or sublingually, include lozenges. Compositions suitable for parenteral administration include aqueous and non-aqueous sterile suspensions or injection solutions. Compositions suitable for rectal administration can be presented as a suppository.

Pharmaceutical compositions of formula (I) compounds described herein can be formulated using a solid or liquid carrier. The solid or liquid carrier should be compatible with the other ingredients of the formulation and not deleterious to the recipient. If the pharmaceutical composition is in tablet form, then the HDAC inhibitor is mixed with a carrier having the necessary compression properties in suitable proportions and compacted in the shape and size desired. If the composition is in powder form, the carrier is a finely divided solid in admixture with the finely divided active ingredient. The powders and tablets can contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins. A solid carrier can include one or more substances that can act as flavoring agents, lubricants, solubilizers, suspending agents, fillers, glidants, compression aids, binders or tablet-disintegrating agents. A suitable carrier can also be an encapsulating material.

If the composition is a solution, suspension, emulsion, syrup, elixir, or pressurized composition, then liquid carriers can be used. In this case, the HDAC inhibitor is dissolved or suspended in a pharmaceutically acceptable liquid carrier. Suitable examples of liquid carriers for oral and parenteral administration include (1) water; (2) alcohols, e.g. monohydric alcohols and polyhydric alcohols such as glycols, and their derivatives; and (3) oils, e.g. fractionated coconut oil and arachis oil. For parenteral administration, the carrier can also be an oily ester such as ethyl oleate and isopropyl myristate. Liquid carriers for pressurized compositions include halogenated hydrocarbon or other pharmaceutically acceptable propellants. The liquid carrier can contain other suitable pharmaceutical additives such as solubilizers; emulsifiers; buffers; preservatives; sweeteners; flavoring agents; suspending agents; thickening agents; colors; viscosity regulators; stabilizers; osmo-regulators; cellulose derivatives such as sodium carboxymethyl cellulose; antioxidants; and bacteriostatics. Other carriers include those used for formulating lozenges such as sucrose, acacia, tragacanth, gelatin and glycerin as well as those used in formulating suppositories such as cocoa butter or polyethylene glycol.

If the composition is to be administered intravenously or intraperitoneally by infusion or injection, solutions of the HDAC inhibitor can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms. The composition suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium as described above. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin. Sterile injectable solutions are prepared by incorporating the HDAC inhibitor in the required amount in the appropriate solvent with some of the other ingredients enumerated above, as required, followed by filter sterilization. In the case of sterile powders for the preparation of sterile injectable solutions, the preferred methods of preparation are vacuum drying and the freeze-drying techniques, which yield a powder of the HDAC inhibitor, plus any additional desired ingredient present in the previously sterile-filtered solutions.

Pharmaceutical compositions can be in unit-dose or multi-dose form or in a form that allows for slow or controlled release of the HDAC inhibitor. Each unit-dose can be in the form of a tablet, capsule or packaged composition such as, for example, a packeted powder, vial, ampoule, prefilled syringe or sachet containing liquids. The unit-dose form also can be the appropriate number of any such compositions in package form. Pharmaceutical compositions in multi-dose form can be packaged in containers such as sealed ampoules and vials. In this case, the HDAC inhibitor can be stored in a freeze-dried (lyophilized) condition requiring only the addition of a sterile liquid carrier immediately prior to use. In addition, extemporaneous injection solutions and suspensions can be prepared from sterile powders, granules and tablets of the kind previously described.

VI. Examples

Synthesis of Formula (I) Compounds/General Synthetic Scheme

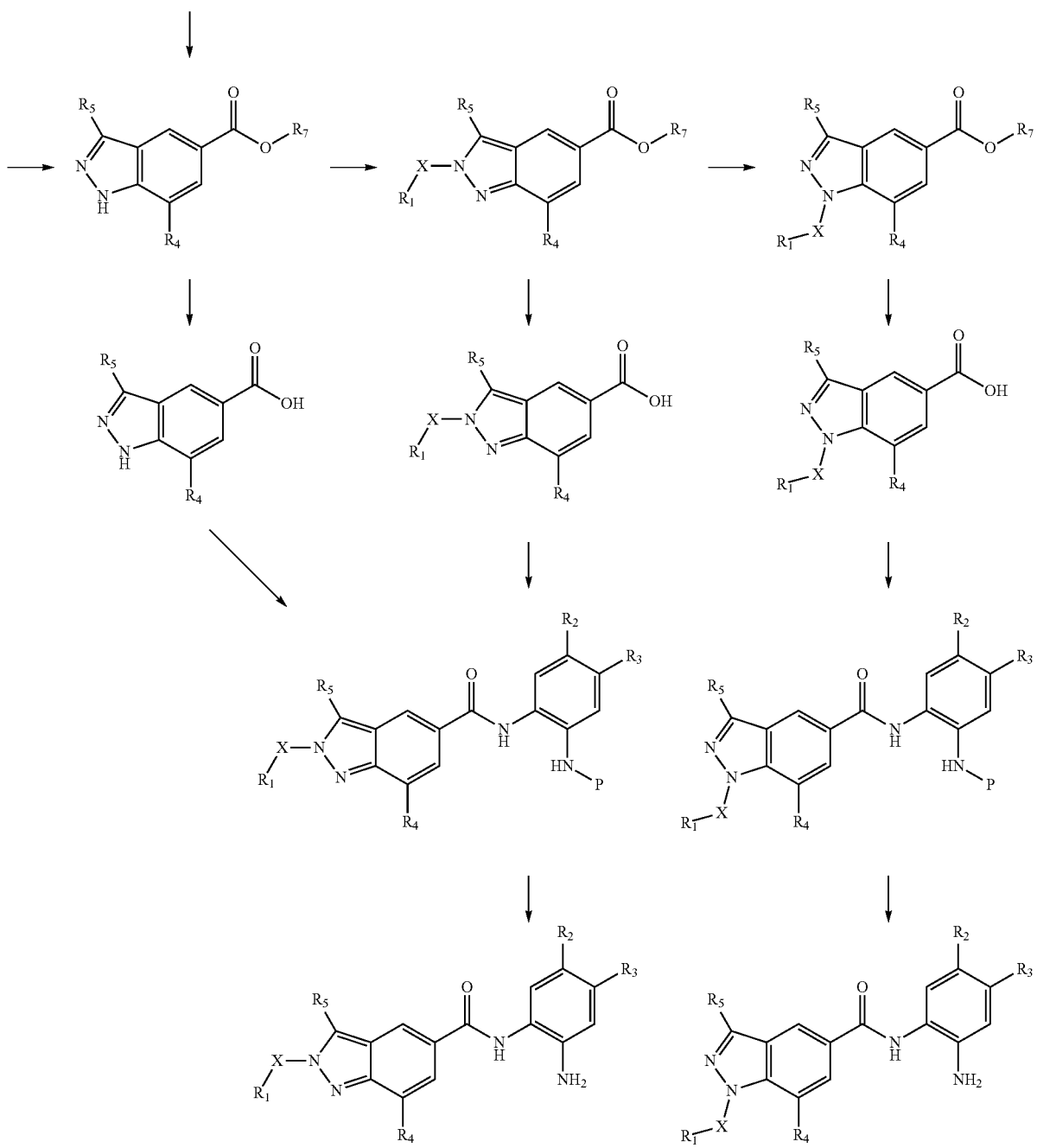

Compounds described herein, of formulae (Ia) and (Ib), where R1, X, R2, R3, R4, R5 are defined as described anywhere herein, can be obtained by reaction of an optionally substituted indazole carboxylate ester ($R_7$ e.g. $C_1$-$C_4$ alkyl, phenyl, benzyl, allyl) with an $R_1$—X— containing moiety using methods well known by those skilled in the art, such as, but not limited to, Heck coupling, Suzuki coupling, alkylation, acylation (see for example Joule J A and Mills K, Heterocyclic Chemistry, Fifth Edition, John Wiley & Sons, Inc., Hoboken, N.J., USA). The substituted or unsubstituted indazole carboxylate can be prepared by methods well known to those skilled in the art and summarized for example in Wiley R. H., Behr L. C., Fusco R., Jarboe C. H., Chemistry of Heterocyclic Compounds: Pyrazoles, Pyrazolines, Pyrazolidines, Indazoles and Condensed Rings, Volume 22, John Wiley & Sons, Inc., Hoboken, N.J., USA. Alternatively $R_1$—X substitution can be introduced when the indazole ring is built. After deprotection of ester $COOR_7$ (using a method appropriate for $R_7$ such as, but not limited to, saponification, hydrogenation, acid hydrolysis) a substituted or unsubstituted N-(o-aminophenyl)amide is prepared by an amide-forming reaction of the acrylic acid with a protected or unprotected substituted or unsubstituted o-phenylenediamine, where P is a protecting group as defined in Wuts P G M and Greene T W, 2006, Greene's Protective Groups in Organic Synthesis, Fourth Edition, John Wiley & Sons, Inc., Hoboken, N.J., USA. Alternatively, the indazole ester can be deprotected to generate a carboxylic acid which can be reacted with a protected or unprotected, substituted or unsubstituted, o-phenylenediamine. The intermediate amide can then be reacted with a reagent delivering the R₁—X moiety using methods well known to those skilled in the art as described above. Compounds disclosed herein can be obtained after deprotection if required using methods well known to those skilled in the art and which are described for example in Wuts P G M and Greene T W, 2006, Greene's Protective Groups in Organic Synthesis, Fourth Edition, John Wiley & Sons, Inc., Hoboken, N.J., USA.

EXAMPLE 1

Synthesis of N-(2-aminophenyl)-1-((5-fluoropyridin-3-yl)methyl)-1H-indazole-5-carboxamide, A4

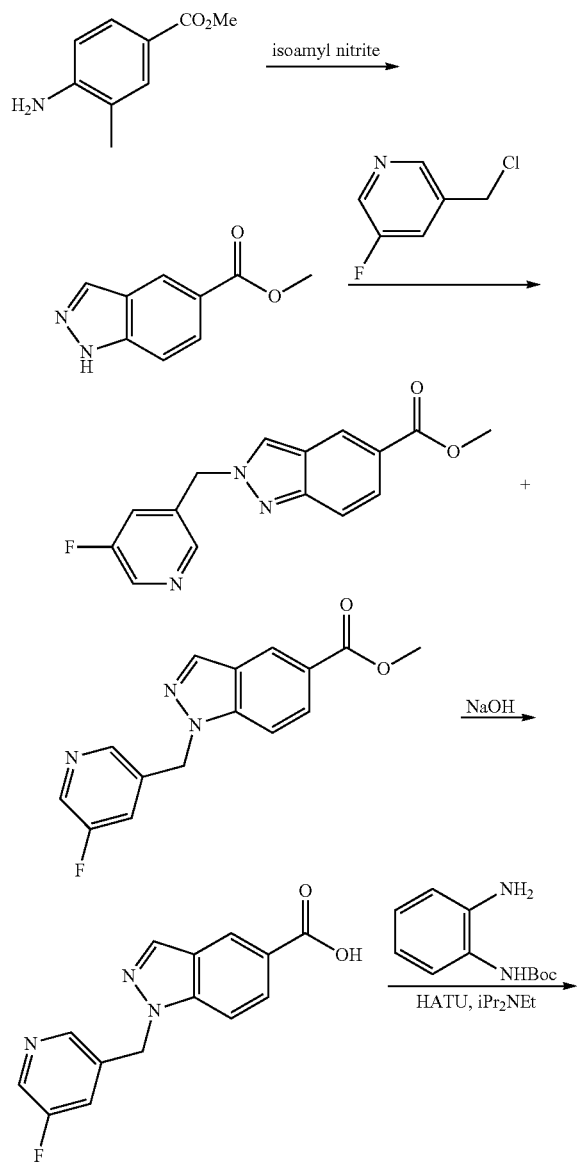

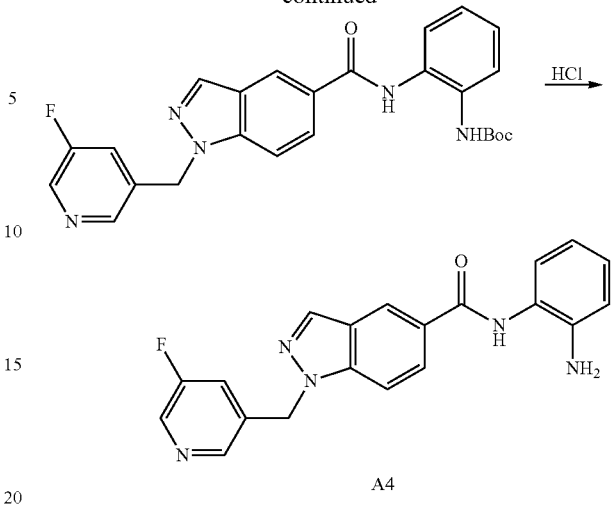

Methyl indazole-5-carboxylate: Isoamyl nitrite (26.8 g, 22.8 mmol) was added to a mixture of methyl 4-amino-3-methylbenzoate (3.4 g, 20.8 mmol) in acetic acid (AcOH, 20 mL). The reaction mixture was stirred at room temperature for 1h then at 80° C. for 5 h. It was concentrated and the residue was purified by silica gel column chromatography (Hexanes/EtOAc 10:1 to 2:1) to give pure methyl 1H-indazole-5-carboxylate.

Methyl 1-((5-fluoropyridin-3-yl)methyl)-1H-indazole-5-carboxylate: To a solution of methyl 1H-indazole-5-carboxylate (694 mg, 3.94 mmol) in DMF (20 mL) was added 3-(chloromethyl)-5-fluoropyridine (3.94 mmol, 1.2 eq, prepared from the alcohol with $SOCl_2$) and $Cs_2CO_3$ (3.85 g) at room temperature. After stirring 3 h at 65° C., the reaction mixture was quenched with aqueous ammonium chloride. The mixture (combined with a small scale reaction) was diluted with $H_2O$, extracted with dichloromethane, washed with sat. $NaHCO_3$ and brine. It was then dried over $Na_2SO_4$, filtered, and concentrated. The residue was purified by column chromatography (Hexanes:EtOAc 7:1 to 0:1) to give regioisomeric products methyl 1-((5-fluoropyridin-3-yl)methyl)-1H-indazole-5-carboxylate (422 mg) and methyl 2-((5-fluoropyridin-3-yl)methyl)-2H-indazole-5-carboxylate (230 mg), the former being carried forward in this synthetic protocol, the latter being used to form regioisomer N-(2-aminophenyl)-2-((5-fluoropyridin-3-yl)methyl)-2H-indazole-5-carboxamide A14.

1-((5-fluoropyridin-3-yl)methyl)-1H-indazole-5-carboxylic acid: Aqueous NaOH (3N, 2 mL) was added to a solution of methyl 1-((5-fluoropyridin-3-yl)methyl)-1H-indazole-5-carboxylate (422 mg, 0.94 mmol) in MeOH/THF (1:1, 10 mL) at room temperature and the mixture was stirred overnight. After removal of the organic solvents under reduced pressure, the resulting aqueous phase was acidified to pH=2-3. The solid was collected by filtration and dried to give methyl 1-((5-fluoropyridin-3-yl)methyl)-1H-indazole-5-carboxylate (328 mg).

tert-Butyl (2-(1((5-fluoropyridin-3-yl)methyl)-1H-indazole-5-carboxamido) phenyl)carbamate: HATU (185 mg, 1.5 eq), DIPEA (0.226 mL), and tert-butyl (2-aminophenyl)carbamate (81 mg, 1.2 eq) were added to a solution of the acid prepared as described above (100 mg, 0.325 mmol) in DMF (3 mL) at 0° C. The mixture was allowed to warm up and was stirred for 16 h. It was quenched with aqueous ammonium chloride, diluted with water, extracted with dichloromethane, and washed with sat. $NaHCO_3$ and brine.

It was then dried over Na$_2$SO$_4$, filtered, and concentrated. The residue was purified by preparative HPLC to yield product tert-butyl (2-(1-((5-fluoropyridin-3-yl)methyl)-1H-indazole-5-carboxamido)phenyl)carbamate (130 mg).

N-(2-aminophenyl)-1-((5-fluoropyridin-3-yl)methyl)-1H-indazole-5-carboxamide, A4: The Boc-protected material (130 mg) was deprotected by incubation with HCl (4M in dioxane, 1 mL) in dioxane (3 mL) and MeOH (1 mL) at 0° C. for 2 h followed by overnight at room temperature. The mixture was then concentrated and the HC salt precipitated. It was filtered and washed with MeOH/EtOAc to yield A4 as the HCl salt (106 mg). HPLC/UV: purity>97%. LC/MS: m/z 362 (M+H)$^+$ $^1$H NMR (CD$_3$OD) δ: 8.72 (br. s, 1H), 8.63 (m, 1H), 8.58 (s, 1H), 8.34 (s, 1H), 8.17 (dd, J=9, 1.5 Hz, 1H), 7.90 (m, 1H), 7.85 (d. J=9 Hz, 1H), 7.6-7.4 (m, 4H), 5.92 (s, 2H).

HDAC Enzyme Inhibition

The HDAC activity inhibition assay was performed as follows to determine the ability of a test compound to inhibit HDAC enzymatic activity. Serial dilutions of HDAC inhibitors were prepared in HDAC assay buffer (25 mM Tris/HCl, pH 8.0, 137 mM NaCl, 2.7 mM KCl, mM MgCl$_2$, pH 8) in 96-well assay plates (Fisher scientific, #07-200-309) and were pre-incubated for 2 hours at room temperature in the presence of 125 µg/ml BSA and purified HDAC1 (BPS Bioscience, San Diego, Calif. #50051), HDAC2 (BPS Bioscience, #50053), or HDAC3/NcoR2 (BPS Bioscience, #50003) at concentrations of 1.25, 1.32, and 0.167 µg/mL, respectively. Following pre-incubation, Fluor-de-Lys™ substrate (Enzo Life Sciences, Plymouth Meeting, Pa., BML-KI104-0050) was added to a final concentration of 10 µM and plates were further incubated for 30 minutes at room temperature. The enzymatic reaction was stopped by addition of Trichostatin A (Sigma-Aldrich, St Louis, Mo., #T8552, final concentration: 100 nM) and trypsin (MP Biomedicals, Solon, Ohio, #02101179) was added to reach a final concentration of 100 µg/mL. After a 15 minute incubation at room temperature, fluorescence was recorded using a Spectramax M2 fluorometer (Molecular Devices, Sunnyvale, Calif.) with excitation at 365 nm and emission at 460 nm. IC50 values were calculated by using a sigmoidal dose-response (variable slope) equation in GraphPad Prism® 5 for Windows (GraphPad Software, La Jolla, Calif.). Results for selected compounds in the HDAC activity inhibition assay are presented in Table 5 (IC$_{50}$ ranges: IA>20 µM, A<1 µM, 1<B<5 µM, 5<C<10 µM, 10<D<20 µM, ND: not determined).

Acid Stability Determination

A 100 µM solution of test compound was prepared by dilution of a 10 mM DMSO stock solution in a 0.01 M solution of HCl in deionized water. Immediately after mixing, an aliquot (100 µL) was sampled and analyzed by HPLC/UV. The area under the compound peak was determined and used as the time zero reference point. The remainder of the acid sample was incubated at 50° C. and samples were taken after 2, 4, and 24 hours of incubation. On a few occasions, samples were taken at 30 rather than 24 hours. These were analyzed by the same HPLC/UV method and the area of the peak corresponding to the test compound was measured. Percent remaining at a given time point was then calculated as the ratio of the area under the peak after incubation to that at time zero times 100. In those cases where a 30 hour time point was recorded, the percent remaining at 24 hours was obtained by interpolation of the percent remaining versus time curve assuming a unimolecular process, i.e. a monoexponential decay. Percent remaining after 24 hours incubation are presented in Table 5 below, where A corresponds to more than 60%, B is between 40 and 60%, C covers 20 to 40% and D means less than 20%.

Brain Penetration Studies

Test compounds were prepared at either 0.5 mg/ml or 5 mg/ml in 30% hydroxypropyl-β-cyclodextrin, 100 mM sodium acetate pH 5.5, 5% DMSO. C57/BL6/J mice were dosed s.c. at 5 mg/kg or 50 mg/kg, or i.v. at 5 mg/kg. Animals were euthanized at pre-dose, 5, 15, 30 min, 1, 2 and 4 hours post-dose and plasma and brain obtained. Three animals per dose per time points were used. The levels of compound in the plasma and brain were determined by standard LC/MS/MS methods. Brain/plasma ratio (BPR) was calculated as the ratio of the C$_{max}$(brain)/C$_{max}$(plasma). The results are shown in Table 5, where IA corresponds to a BPR less than 0.1, D is between 0.1 and 0.2, C is 0.2 to 0.5, B comprises 0.5 to 1 and A is greater than 1.

In-cell Deacetylase Inhibition Assay (DAC Assay)

GM 15850(lymphoblastoid cells line) cells were seeded in 96-well plates at an appropriate density (100,000 cells/well) in 90 µL RPMI1640 medium containing 10% v/v fetal bovine serum (FBS), 1% v/v penicillin/streptomycin, and 1% v/v L-glutamine. Compound dilutions were made in 100% DMSO followed by parallel dilution in media with 2% DMSO. 10 µl of the compound dilutions were added to the cells to achieve the desired concentrations. The final concentration of DMSO in each well was 0.2%. The cells were incubated for 4 h at 37° C. with 5% CO$_2$. After incubation, the cells were centrifuged down and the supernatant was removed. The cell pellets were washed with 100 µL phosphate-buffered saline (PBS) and then lysed with 45 µL lysis buffer (HDAC assay buffer at pH 8.0 (25 mM Tris/HCl, 137 mM NaCl, 2.7 mM KCl, 1 mM MgCl$_2$)+1% v/v Igepal CA-630). To initiate the reaction, the HDAC substrate KI-104 (Enzo Life Sciences, Farmingdale, N.Y.) was added to a final concentration of 50 µM. The reaction was stopped after 30 min incubation by addition of 50 µL developer (6 mg/mL trypsin in HDAC assay buffer). The reaction was allowed to develop for 30 min at room temperature and the fluorescence signal was detected using a fluorometer (Spectramax M2, Molecular Devices, Sunnyvale, Calif.) with excitation and emission wavelengths of 360 nm and 470 nm respectively. The data was fitted to a sigmoidal dose response equation with variable slope in GraphPad Prism 5.0 (GraphPad Software, La Jolla, Calif.) to determine IC50. Bottom and top of the curve were fixed to the average fluorescence response of control wells with no cells and cells but no compound respectively. IC50's are reported in Table 5, where A stands for IC50 less than 1 µM, B between 1 and 5 µM, C from 5 to 10 µM, D from 10 to 20 µM, and IA for IC50 above 20 µM.

Effect of HDAC Inhibitors on Frataxin (FXN) mRNA Expression

Blood is collected from Friedreich's ataxia patient donors into tubes containing the anti-coagulant EDTA. Primary lymphocytes are isolated using Lymphocyte Separation Medium (MP Biomedicals, Solon, Ohio) following the manufacturer's instructions and including a few modifications made by Repligen. After a final wash in Phosphate Buffered Saline (PBS), the cells are distributed into a 6-well cell culture plate in cell growth medium. The test HDAC inhibitor compound is added to cells in a dose escalating manner (usually concentrations range from 1 to 10 µM) and 0.1% DMSO is added to one well of cells as a no treatment control. Cells are incubated for 48 hours at 37° C. in a CO$_2$ incubator; cell counts are taken using a Countess automated cell counter (Invitrogen, Carlsbad, Calif.). Equivalent numbers of cells for all treatment conditions are pelleted by centrifugation and resuspended in cell lysis buffer. Total RNA is isolated from approximately 1×10⁶ primary lymphocytes using a RNeasy Mini Kit (Qiagen, Valencia, Calif.), following the manufacturer's instructions and including an optional on-column DNAse digestion step. The isolation is performed either manually or using the QIAcube (Qiagen, Valencia, Calif.), an instrument that automates much of the isolation procedure. The RNA yield and concentration is determined using a Nanodrop spectrophotometer (Thermo Fisher Scientific, Waltham, Mass.) and depending on the RNA concentration, one of two protocols is used to measure frataxin (FXN) transcript levels. For samples containing at least 15 ng/μL RNA a TaqMan® Probe-based (Applied Biosystems, Carlsbad, Calif.) qRT-PCR method is used, while for samples containing less than 15 ng/μL RNA a SYBR Green qRT-PCR method is used. In the TaqMan® Probe-based method specific primer/probe pairs for FXN and GAPDH are multi-plexed in each reaction. In the SYBR Green method FXN and GAPDH are amplified in separate reactions. In both methods each RNA sample is analyzed in triplicate (preferably) or duplicate (minimally) using a one-step qRT-PCR master mix that contains all the components necessary for cDNA synthesis and PCR amplification in a single, continuous reaction. After cycling is complete, MxPro Software (Agilent Technologies, Santa Clara, Calif.) is used to analyze the collected data and determine the relative amount of FXN mRNA compared to a control sample. An adaptive baseline method is used for baseline correction whereby an algorithm automatically selects the appropriate baseline cycles for each well and each dye. An amplification-based threshold is set and the corresponding threshold cycle, or Ct, is obtained for calculating target concentration. The Ct values for each target gene (FXN and GAPDH) for each replicate series are averaged. The amount of FXN (or GAPDH) in the sample is determined as the relative quantity to the calibrator where the calibrator sample is assigned an arbitrary quantity of 1. The following equation is used: Relative quantity to the calibrator=$2^{-\Delta Ct}$ where $\Delta Ct$=(Ct_gene)unknown−(Ct_gene)calibrator, gene is either FXN or GAPDH, calibrator is a DMSO control sample, and unknown is a HDACi treated sample. The relative quantity of FXN is normalized to cell number and RNA input. Data is reported in Table 5 below, where the concentration required for a 2-fold increase in FXN mRNA is reported as A if less than 5 μM, B if between 5 and 10 μM, C if greater than 10 μM.

Hepatocyte Protocol

To assess the stability and metabolism of RGFP compounds and to quantify the metabolites in hepatocytes. This assay was designed to evaluate the metabolism of RGFP compounds, following their incubation with human, monkey, dog and rat hepatocytes by monitoring either parent drug disappearance or metabolite appearance using LC-MS/MS. The results are shown in Table 5 ((% Left in Hep: IA<10%, 50%<A, 50%>B>30%, 30%>C>10%, ND: not determined).

Equipment

Applied Biosystem Triple Quadrupole LC/MS/MS; Ice bucker, timer; 96 well plates; Falcon, Cat #353072; 96 well plates shaker; Various pipettes: 10 μL, 20 μL, 200 μL, and 1000 μL; Test tubes: Catalog #VWR 47729-572, 13×100 mm

TABLE 3

Materials and Reagents

| Item | Vendor | Catalog # |
| --- | --- | --- |
| Human Hepatocytes | Celsis | X008001 |
| Monkey Hepatocytes | Celsis | M00350 |
| Dog Hepatocytes | Celsis | M00205 |
| Rat Hepatocytes | Celsis | M00005 |
| Torpedo Antibiotix Mix | Invitro Technologies | Z99000 |
| In VitroGRO HT Medium | Celsis | Z99019 |
| In VitroGRO KHB | Celsis | Z99074 |
| Acetonitrile | Fisher | A-9981 |
| Methanol | Fisher | A-4521 |
| Trypan Blue Solution | Sigma Chemical | T-8154 |

Procedure: Turn on the water-bath heater to 37° C. Take out the KHB buffer and make sure it is at room temp before use. Prepare 2.5 mM concentration of RGFP compound in DMSO stock. Add 10 μL of above DMSO stock to 2490 μL KHB buffer; final concentration of RGFP compound will be 10 μM. Pre-warm 45 ml InVitro HT Medium to 37° C. in a sterile 50 ml conical tube. Add 1.0 mL Torpedo Antibiotic Mix per 45 mL InVitro HT medium. Transfer 13 mL of warm HT medium with Antibiotic Mix into a 15 mL conical tube. Carefully remove the hepatocyte vials from liquid nitrogen (liquid phase). Immediately immerse the vial into a 37° C. water bath. Shake gently until the ice melts entirely. Do not keep the cells in 37° C. water bath longer than necessary. Immediately empty contents of the vial into 13 ml of pre-warmed InVitro HT Medium with antibiotics. Rinse the vial with the HT media just transferred the hepatocytes to, in order to ensure complete transfer. Centrifuge the cell suspension at 600 RPM for 5 minutes at room temperature. Discard the supernatant by either pouring in one motion (do not pour partially and re-invert centrifuge tube) or aspirating using a vacuum pump. Add 1.0 ml of KHB (at room temperature) buffer to the tube of hepatocyte pellet. Loosen the cell pellet by gently swirling the centrifuge tube. Transfer 100 μL of above solution to a different tube and add 900 μL of KHB buffer to count the cells. Determine the total cell count and the number of viable cells using the Trypan Blue exclusion method. Once the cell count is obtained, multiply the number by 10 (attributing to the dilution factor). Add required volume of KHB buffer to the tube containing hepatocytes such that the final count will be 2 million cells/mL. Dispense 50 μL of 2 million cells/ml to a 96 well plate and then add 50 μl of DMSO stock to respective wells (such that, the concentration of RGFP compounds is 5 μM and number of cells are 100000 in each well). Place the plates on a shaker in a 37° C. incubator with 5% $CO_2$. Separate plates for each time point are advisable (Time points: 0 h, 1 h, 2 h, and 6 h). After each time point, add 100 μL of quenching solution. Quenching solution is an acetonitrile solution containing RGFP531 (10 μM) internal standard, 0.1% formic acid and phenylglyoxol (400 μM). The formic acid and phenylglyoxal is used for the identification and quantification of OPD as mentioned above. Pipette up and down a few times to ensure a complete stop of reaction. Transfer all the solution into a 1.5 ml tube, vortex thoroughly, and centrifuge at 14000 RPM at 4° C. for 5 minutes to precipitate cell debris. Transfer the 150 μL of supernatant to vials for analysis on LC-MS/MS.

LC-MS/MS parameters for RGFP compounds and metabolites including OPD: LC-MS/MS Parameters for API 2000 QTrap: System: HPLC 1100; Column: Gemini C18, 5 μM 4.6×50 mm; Column Temp: Ambient; MS: API 2000 QTrap (MI mode); Mobile Phase A: HPLC water with 0.05% Formic Acid; Mobile Phase B: Acetonitrile with 0.05% Formic Acid. Table 4 shows an exemplary HPLC method for compound A11, which can be modified for other compounds as disclosed herein.

TABLE 4

HPLC method for 2000QTrap LCMS

| Total time (min) | Flow Rate (ul/min) | A % | B % | C % | D % |
|---|---|---|---|---|---|
| 0 | 750 | 85 | 15 | 0 | 0 |
| 0.5 | 750 | 85 | 15 | 0 | 0 |
| 2.5 | 750 | 5 | 95 | 0 | 0 |
| 5 | 750 | 5 | 95 | 0 | 0 |
| 5.5 | 750 | 85 | 15 | 0 | 0 |
| 7.5 | 750 | 85 | 15 | 0 | 0 |

TABLE 5

| Coding | Structure | MW | clogP | tPSA | HDAC1 IC50 (uM) | HDAC2 IC50 (uM) | HDAC3 IC50 (uM) | BPR | Cmax brain (ng/mL) | DAC IC50 (uM) | % left 6 h Hum hep | acid formed (absolute) | OPD (ng/mL) | Fxn >2X uM | Acid Stability % Left 24 hr |
|---|---|---|---|---|---|---|---|---|---|---|---|---|---|---|---|
| A1 | indazole-benzylpyridine with anilide-NH2 | A | 1.51 | 83 | A | A | A | C | C | A | A | No acid | No OPD | ND | ND |
| A2 | indazole-benzyl with anilide-NH2 | A | 3.01 | 71 | A | A | A | A | C | A | B | No acid | No OPD | ND | B |
| A3 | indazole-methylpyrazolylmethyl with anilide-NH2 | A | 1.12 | 86 | A | A | A | C | C | A | A | A | No OPD | ND | ND |
| A4 | indazole-(5-fluoropyridin-3-yl)methyl with anilide-NH2 | A | 1.74 | 83 | A | A | A | C | C | A | A | No acid | No OPD | ND | ND |

TABLE 5-continued

| Coding | Structure | MW | clogP | tPSA | HDAC1 IC50 (uM) | HDAC2 IC50 (uM) | HDAC3 IC50 (uM) | BPR | Cmax brain (ng/mL) | DAC IC50 (uM) | % left 6 h Hum hep | acid formed (absolute) | OPD (ng/mL) | Fxn >2X uM | Acid Stability % Left 24 hr |
|---|---|---|---|---|---|---|---|---|---|---|---|---|---|---|---|
| A5 | 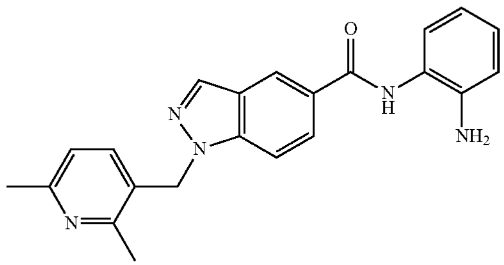 [SMILES: Cc1ccc(Cn2ncc3cc(C(=O)Nc4ccccc4N)ccc32)c(C)n1] | A | 2.51 | 83 | A | A | A | C | C | A | B | No acid | No OPD | ND | ND |
| A6 | 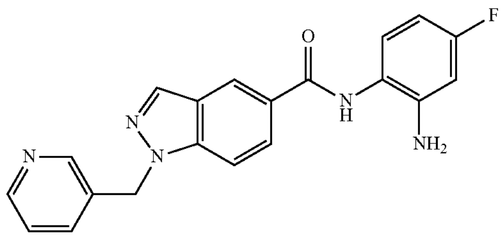 [SMILES: Nc1cc(F)ccc1NC(=O)c1ccc2c(cnn2Cc2cccnc2)c1] | A | 1.86 | 83 | A | A | A | ND | ND | B | B | No acid | No OPD | ND | A |
| A7 | 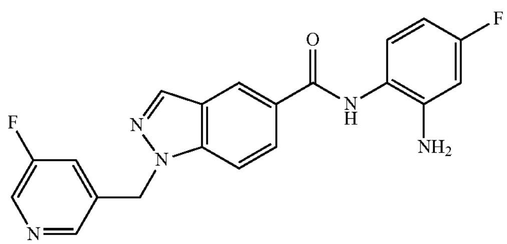 [SMILES: Nc1cc(F)ccc1NC(=O)c1ccc2c(cnn2Cc2cncc(F)c2)c1] | A | 2.08 | 83 | A | A | A | C | C | B | B | No Acid | No OPD | ND | B |
| A8 | 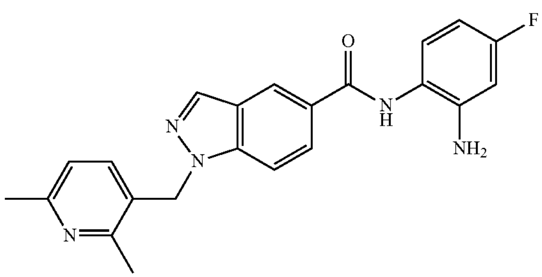 [SMILES: Cc1ccc(Cn2ncc3cc(C(=O)Nc4ccc(F)cc4N)ccc32)c(C)n1] | A | 2.85 | 83 | A | B | A | ND | ND | B | A | No Acid | No OPD | ND | A |

TABLE 5-continued

| Coding | Structure | MW | clogP | tPSA | HDAC1 IC50 (uM) | HDAC2 IC50 (uM) | HDAC3 IC50 (uM) | BPR | Cmax brain (ng/mL) | DAC IC50 (uM) | % left 6 h Hum hep | acid formed (absolute) | OPD (ng/mL) | Fxn >2X uM | Acid Stability % Left 24 hr |
|---|---|---|---|---|---|---|---|---|---|---|---|---|---|---|---|
| A9 | 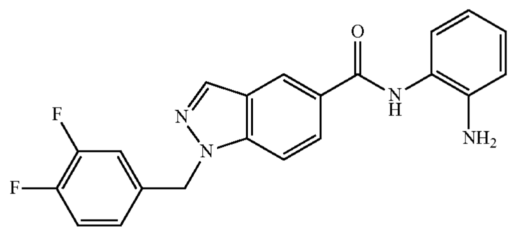 [SMILES: Nc1ccccc1NC(=O)c1ccc2c(cnn2Cc2ccc(F)c(F)c2)c1] | A | 3.22 | 71 | A | A | A | A | C | ND | B | No Acid | No OPD | A | A |
| A10 | 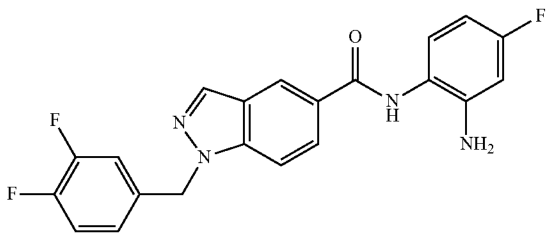 [SMILES: Nc1cc(F)ccc1NC(=O)c1ccc2c(cnn2Cc2ccc(F)c(F)c2)c1] | A | 3.57 | 71 | A | A | A | A | B | ND | C | No Acid | No OPD | ND | C |
| A11 | 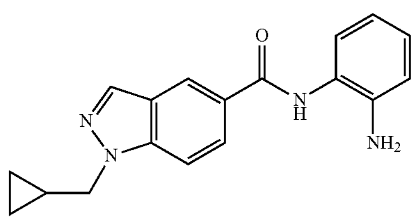 [SMILES: Nc1ccccc1NC(=O)c1ccc2c(cnn2CC2CC2)c1] | A | 2.21 | 71 | A | A | A | C | B | ND | B | No Acid | No OPD | ND | B |
| A12 | 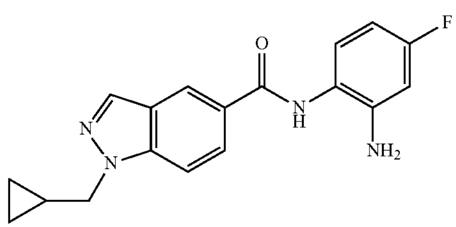 [SMILES: Nc1cc(F)ccc1NC(=O)c1ccc2c(cnn2CC2CC2)c1] | A | 2.56 | 71 | B | C | A | B | B | IA | C | No Acid | No OPD | C | B |

TABLE 5-continued

| Coding | Structure | MW | clogP | tPSA | HDAC1 IC50 (uM) | HDAC2 IC50 (uM) | HDAC3 IC50 (uM) | BPR | Cmax brain (ng/mL) | DAC IC50 (uM) | % left 6 h Hum hep | acid formed (absolute) | OPD (ng/mL) | Fxn >2X uM | Acid Stability % Left 24 hr |
|---|---|---|---|---|---|---|---|---|---|---|---|---|---|---|---|
| A13 | ![structure] | A | 1.51 | 83 | A | A | A | IA | C | A | A | A | No OPD | ND | ND |
| A14 | ![structure] | A | 1.74 | 83 | A | A | A | C | C | A | A | A | No OPD | ND | ND |
| A15 | ![structure] | A | 2.51 | 83 | A | B | A | IA | C | A | A | A | No OPD | ND | ND |

REFERENCES 1) 2012. o-Phenylenediamine [MAK Value Documentation, 1999]. The MAK Collection for Occupational Health and Safety. 216-235.
2) A Comprehensive Guide to the Hazardous Properties of Chemical Substances by Pradyot Patnaik, 3rd edition, Pg 257-258.
3) Weisburger E K, Russfield A B, Homburger F, Weisburger J H, Boger E, Van Dongen C G, Chu K C (1978) Testing of twenty-one environmental aromatic amines or derivatives for long-term toxicity or carcinogenicity. J Environ Pathol Toxicol 2: 325-356.
4) Sontag J M (1981) Carcinogenicity of substituted-benzenediamines (phenylenediamines) in rats and mice. J Nat Cancer Inst 66: 591-601.
5) Bioassay of 4-Chloro-o-phenylenediamine for possible caricogeneicty. National Cancer Institute CARCINO-GENESIS Technical Report Series No. 63, 1978.
6) Saruta N, Yamaguchi S, Matsuoka T (1962) Sarcoma produced by subdermal administration of metaphenylenediamine and metaphenylenediamine hydrochloride. *Kyushu J Med Sci*, 13: 175-179.

A number of embodiments have been described herein. Nevertheless, it will be understood that various modifications may be made without departing from the spirit and scope of the disclosure. Accordingly, other embodiments are within the scope of the following claims.

What is claimed:

1. A compound having formula (I), or a pharmaceutically acceptable salt thereof:

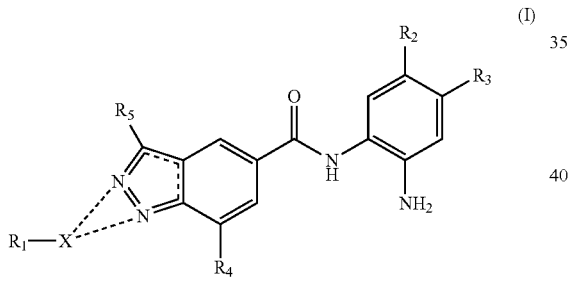

wherein:
$R_1$—X is attached to only one of the ring nitrogen atoms; X is:
(i) —Y—[C($R^a$)$_2$]$_a$-A-[C($R^b$)$_2$]$_b$—B—;
(ii) direct bond; or
(iii) C=O, C($R^j$)$_2$—C(=O), C(=O)—C($R^j$)$_2$, SO$_2$—NR$^k$, NR$^k$—SO$_2$, C(=O)NR$^k$ or NR$^k$—C(=O);

wherein:
Y is bond, CR$^c$=CR$^d$, O, NR$^e$, or S(O)$_m$;
each of A and B is, independently, a bond, O, NR$^f$, or S(O)$_m$;
a is 1, 2, or 3;
b is 0, 1, 2, or 3;
m is 0, 1, or 2;
each occurrence of R$^a$ and R$^b$ is independently selected from H, F, OH, C1-6 alkyl, C3-C6 cycloalkyl, NH$_2$, OCO—(C1-C6 alkyl), OCO—(C3-C6 cycloalkyl), C1-C6 alkoxy, C1-C6 fluoroalkoxy, and cyano; or
one or more of the following can apply with respect to R$^a$ and R$^b$:
any two R$^a$, together with the carbons to which each is attached, together form C3-C6 cycloalkyl or heterocyclyl including 3-6 ring atoms, in which one of the heterocyclyl ring atoms is selected from O, S(O)$_m$, and NR$^g$; or one R$^a$ and one R$^b$, together with the carbons to which each is attached, form C3-C6 cycloalkyl or heterocyclyl including 3-6 ring atoms, in which one of the heterocyclyl ring atoms is selected from O; S(O)m and NR$^g$; or any two R$^b$, together with the carbons to which each is attached, form C3-C6 cycloalkyl or heterocyclyl including 3-6 ring atoms, in which one of the ring atoms is selected from O; S(O)m and NR$^g$;

each of R$^c$ and R$^d$ is independently selected from H, F, OH, C1-6 alkyl, C3-C5 cycloalkyl, NH$_2$, OCO—(C1-C6 alkyl), OCO—(C3-C5 cycloalkyl), C1-C6 alkoxy, C1-6 fluoroalkoxy, and cyano;

or R$^c$ and R$^d$, together with the carbons to which each is attached form a C5-C7 cycloalkyl or heterocyclyl including 3-6 ring atoms, in which from 1-2 of the heterocyclyl ring atoms are independently selected from O, S(O)$_m$ and NR$^{g'}$;

each occurrence of R$^e$, R$^f$, R$^g$ and R$^{g'}$ is independently selected from H, C1-6 alkyl, —C(=O)H, —C(=O)R$^h$, C(=O)O(C1-C6 alkyl), C(=O)N(R$^i$)$_2$, and SO$_2$—R$^h$; wherein R$^h$ is selected from C1-C6 alkyl, CH$_2$-(heteroaryl including 5-10 ring atoms), CH$_2$—(C6-C10 aryl), and C6-C10 aryl; and each occurrence of R$^i$ is independently selected from H, C1-C6 alkyl, CH$_2$-(heteroaryl including 5-10 ring atoms), CH$_2$—(C6-C10 aryl), and C6-C10 aryl;

each occurrence of R$^j$ is independently selected from H, F, OH, C1-6 alkyl, C3-C6 cycloalkyl, NH$_2$, OCO—(C1-C6 alkyl), OCO—(C3-C6 cycloalkyl), C1-C6 alkoxy, C1-C6 fluoroalkoxy, and cyano;

or R$^j$—C—R$^j$ together form C3-C6 cycloalkyl or heterocyclyl including 3-6 ring atoms, in which one of the heterocyclyl ring atoms is selected from O; S(O)m and NR$^{j'}$;

each occurrence of R$^{j'}$ and R$^k$ is independently selected from H, C1-C6 alkyl, —C(=O)H, —C(=O)R$^m$, C(=O)O(C1-C6 alkyl), C(=O)N(R$^n$)$_2$, and SO$_2$—R$^m$, wherein R$^m$ is selected from C1-C6 alkyl, CH$_2$-(heteroaryl including 5-10 ring atoms), CH$_2$—(C6-C10 aryl), and C6-C10 aryl; and each occurrence of R$^n$ is independently selected from H, C1-C6 alkyl, CH$_2$-(heteroaryl including 5-10 ring atoms), CH$_2$—(C6-C10 aryl), and C6-C10 aryl, and wherein the aryl and heteroaryl portion in R$^m$ and R$^n$ can be optionally substituted with 1-3 independently selected substituents F, C1-C6 alkyl, fluoro C1-C6 alkyl, C3-C6 cycloalkyl, C1-C6 alkoxy, C1-C6 fluoroalkoxy, or cyano;

further wherein:
(a) when each of A and B is a bond, and b is 0, then X has the following formula:

—Y—[C(R$^a$)$_2$]$_a$—;

(b) when b is 0 or 1, then A and B cannot both be heteroatoms; and
(c) when A or B serves as the point of connection of X to the nitrogen ring atoms, then A or B cannot be a heteroatom;

R1 is:
(i) monocyclic or bicyclic heteroaryl including from 5-10 ring atoms, which is optionally substituted with from 1-3 R°; wherein from 1-4 of the ring atoms are a heteroatom independently selected from 0, N, N—H, N—R°, and S;
(ii) C6-C10 aryl, which is optionally substituted with from 1-3 R°;
(iii) C3-C10 cycloalkyl or C3-C10 cycloalkenyl, each of which is optionally substituted with from 1-6 R°; or
(iv) hydrogen;
R4 is H or R° and each occurrence of R° is independently selected from the group consisting of halogen; C1-C6 alkyl; fluoro(C1-C6)alkyl; hydroxyl; hydroxy($C_1$-$C_4$) alkyl; C1-C6 alkoxy; fluoro(C1-C6)alkoxy; (C1-C6 alkyl)C(O)—; (C1-C6 alkyl)NH—; (C1-C6 alkyl)$_2$N—; —N*(R°′)$_2$, wherein R°′—N*—R°′ together form a saturated ring having 5 or 6 ring atoms, in which 1 or 2 ring atoms are optionally a heteroatom independently selected from NH, N(C1-C6alkyl), O, or S; formyl; formyl($C_1$-$C_4$) alkyl; cyano; cyano($C_1$-$C_4$) alkyl; benzyl; benzyloxy; (heterocyclyl)—(C0-C6) alkyl, wherein the heterocyclyl portion includes 5 or 6 ring atoms, in which 1 or 2 of the ring atoms are a heteroatom independently selected from NH, N(alkyl), O, or S; phenyl; heteroaryl including from 5-6 ring atoms, wherein from 1-4 of the ring atoms are a heteroatom independently selected from O, N, N—H, N—R°″, and S, each of which is optionally substituted with from 1-3 R°″; SO$_2$—(C1-C6)alkyl; SO—(C1-C6)alkyl; and nitro;
each occurrence of R°″ is independently selected from the group consisting of halogen; C1-C6 alkyl; fluoro(C1-C6)alkyl; hydroxyl; hydroxy($C_1$-$C_4$)alkyl; C1-C6 alkoxy; fluoro(C1-C6)alkoxy; (C1-C6 alkyl)C(O)—; (C1-C6 alkyl)NH—; (C1-C6 alkyl)$_2$N—; formyl; formyl($C_1$-$C_4$) alkyl; cyano; cyano($C_1$-$C_4$) alkyl; benzyl; benzyloxy; (heterocyclyl)—(C0-C6) alkyl, wherein the heterocyclyl portion includes 5 or 6 ring atoms, in which 1 or 2 of the ring atoms are a heteroatom independently selected from NH, N(C1-C6alkyl), O, or S; phenyl; heteroaryl including from 5-6 ring atoms, wherein from 1-4 of the ring atoms are a heteroatom independently selected from O, N, N—H, N—(C1-C6 alkyl), and S; SO$_2$—(C1-C6)alkyl; SO—(C1-C6)alkyl; and nitro;
R5 is selected from the group consisting of: hydrogen, halogen; C1-06 alkyl; fluoro(C1-C6)alkyl; hydroxyl; hydroxy($C_1$-$C_4$)alkyl; (C1-C6 alkyl)C(O)—; formyl; formyl($C_1$-$C_4$) alkyl; cyano; cyano($C_1$-$C_4$) alkyl; benzyl; (heterocyclyl)-(C0-C6)alkyl, wherein the heterocyclyl portion includes 5 or 6 ring atoms, in which 1 or 2 of the ring atoms are a heteroatom independently selected from NH, N(C1-C6alkyl), O, or S; phenyl; heteroaryl including from 5-6 ring atoms, wherein from 1-4 of the ring atoms are a heteroatom independently selected from O, N, N—H, and S; SO$_2$—(C1-C6)alkyl; SO—(C1-C6)alkyl; and nitro;
R2 is selected from H, F, Cl, CF$_3$, CF$_2$CF$_3$, CH$_2$CF$_3$, OCF$_3$, OCHF$_2$, phenyl; or phenyl substituted with 1-3 R°; and
R3 is H, F, or Cl.

2. The compound or salt of claim 1, wherein X is —Y—[C(R$^a$)$_2$]$_a$-A-[C(R$^b$)$_2$]$_b$—B—.

3. The compound or salt according to claim 1, wherein X is CH$_2$.

4. The compound or salt according to claim 1, wherein X is (CH$_2$)$_{2-4}$.

5. The compound or salt according to claim 1, wherein X is —CH=CH—C(R$^a$)$_2$—or —CH=CHC(R$^a$)$_2$C(R$^a$)$_2$—.

6. The compound or salt according to claim 1, wherein X is —O—(CH$_2$)$_{2-3}$ or —N(CH$_3$)—(CH$_2$)$_{2-3}$.

7. The compound or salt according to claim 1, wherein X is a bond.

8. The compound or salt according to claim 1, wherein R2 is hydrogen, and R3 is F or Cl.

9. The compound or salt according to claim 1, wherein:
X is:
  (i) —Y—[C(R$^a$)$_2$]$_a$-A-[C(R$^b$)$_2$]$_b$—B—;
  (ii) direct bond; or
  (iii) C=O, C(R$^j$)$_2$—C(=O), C(=O)—C(R$^j$)$_2$, SO$_2$—NR$^k$, NR$^k$—SO$_2$, C(=O)NR$^k$ or NR$^k$—C(=O);
R1 is:
  (i) monocyclic or bicyclic heteroaryl including from 5-10 ring atoms, which is optionally substituted with from 1-3 R°; wherein from 1-4 of the ring atoms are a heteroatom independently selected from O, N, N—H, N—R°, and S;
  (ii) C6-C10 aryl, which is optionally substituted with from 1-3 R°;
  (iii) C3-C10 cycloalkyl or C3-C10 cycloalkenyl, each of which is optionally substituted with from 1-3 R°; or
  (iv) hydrogen;
R° is independently selected from the group consisting of halogen; C1-C6 alkyl; fluoro(C1-C6)alkyl; hydroxyl; hydroxy($C_1$-$C_4$)alkyl; C1-C6 alkoxy; fluoro(C1-C6) alkoxy; (C1-C6 alkyl)C(O)—; (C1-C6 alkyl)NH—; (C1-C6 alkyl)$_2$N—; —N*(R°′)$_2$, wherein R°′—N*—R°′ together form a saturated ring having 5 or 6 ring atoms, in which 1 or 2 ring atoms are optionally a heteroatom independently selected from NH, N(C1-C6alkyl), O, or S; cyano; phenyl; heteroaryl including from 5-6 ring atoms, wherein from 1-4 of the ring atoms are a heteroatom independently selected from O, N, N—H, N—R°″, and S, each of which is optionally substituted with from 1-3 R°″; and SO$_2$—(C1-C6)alkyl;
R4 is hydrogen or halo;
R5 is hydrogen; and
(i) each of R2 and R3 is hydrogen; or (ii) R2 is hydrogen, and R3 is fluoro; or (iii) R2 is a substituent other than hydrogen, and R3 is hydrogen.

10. The compound or salt according to claim 1, wherein:
X is —Y—[C(R$^a$)$_2$]$_a$-A-[C(R$^b$)$_2$]$_b$—B—;
R1 is:
  (i) monocyclic or bicyclic heteroaryl including from 5-10 ring atoms, which is optionally substituted with from 1-3 R°; wherein from 1-4 of the ring atoms are a heteroatom independently selected from O, N, N—H, N—R°, and S;
  (ii) C6-C10 aryl, which is optionally substituted with from 1-3 R°; or
  (iii) C3-C10 cycloalkyl or C3-C10 cycloalkenyl, each of which is optionally substituted with from 1-3 R°; or
  (iv) hydrogen;
R° is independently selected from the group consisting of halogen; C1-C6 alkyl; fluoro(C1-C6)alkyl; hydroxyl; hydroxy(C1-C4)alkyl; C1-C6 alkoxy; fluoro(C1-C6) alkoxy; (C1-C6 alkyl)C(O)—; (C1-C6 alkyl)NH—; (C1-C6 alkyl)$_2$N—; —N*(R°′)$_2$, wherein R°′—N*—R°′ together form a saturated ring having 5 or 6 ring atoms, in which 1 or 2 ring atoms are optionally a heteroatom independently selected from NH, N(C1-C6alkyl), 0, or S; cyano; phenyl; heteroaryl including from 5-6 ring atoms, wherein from 1-4 of the ring atoms are a heteroatom independently selected from O, N, N—H, N—R°", and S, each of which is optionally substituted with from 1-3 R°"; and SO$_2$—(C1-C6)alkyl;
R4 is hydrogen or halo;
R5 is hydrogen; and
(i) each of R2 and R3 is hydrogen; or (ii) R2 is hydrogen, and R3 is fluoro; or (iii) R2 is a substituent other than hydrogen, and R3 is hydrogen.

11. The compound or salt according to claim 1, wherein:
X is —Y—[C(R$^a$)$_2$]$_a$-A-[C(R$^b$)$_2$]$_b$—B—;
R1 is C3-C10cycloalkyl or C3-C10 cycloalkenyl, optionally substituted with from 1-3 R°;
R° is independently selected from the group consisting of: halogen; C1-C6 alkyl; fluoro(C1-C6)alkyl; hydroxyl; hydroxy(C$_1$-C$_4$)alkyl; C1-C6 alkoxy; fluoro(C1-C6) alkoxy; (C1-C6 alkyl)NH—; (C1-C6 alkyl)$_2$N—; cyano; and SO$_2$—(C1-C6)alkyl.;
R4 is hydrogen or halo;
R5 is hydrogen; and
(i) each of R2 and R3 is hydrogen; or (ii) R2 is hydrogen, and R3 is fluoro; or (iii) R2 is a substituent other than hydrogen, and R3 is hydrogen.

12. The compound or salt according to claim 1, wherein:
X is —Y—[C(R$^a$)$_2$]$_a$-A-[C(R$^b$)$_2$]$_b$—B—;
R1 is monocyclic or bicyclic heteroaryl including from 5-10 ring atoms, optionally substituted with from 1-3 R°; wherein from 1-4 of the ring atoms are a heteroatom independently selected from O, N, N—H, N—R°, and S;
R° is independently selected from the group consisting of: halogen; C1-C6 alkyl; fluoro(C1-C6)alkyl; hydroxyl; hydroxy(C$_1$-C$_4$)alkyl; C1-C6 alkoxy; fluoro(C1-C6) alkoxy; (C1-C6 alkyl)NH—; (C1-C6 alkyl)$_2$N—; cyano; and SO$_2$—(C1-C6)alkyl;
R4 is hydrogen or halo;
R5 is hydrogen; and
(i) each of R2 and R3 is hydrogen; or (ii) R2 is hydrogen, and R3 is fluoro; or (iii) R2 is a substituent other than hydrogen, and R3 is hydrogen.

13. The compound or salt according to claim 1, wherein:
X is —Y—[C(R$^a$)$_2$]$_a$-A-[C(R$^b$)$_2$]$_b$—B—;
R1 is C6-C10 aryl, optionally substituted with from 1-3 R°;
R° is independently selected from the group consisting of: halogen; C1-C6 alkyl; fluoro(C1-C6)alkyl; hydroxyl; hydroxy(C$_1$-C$_4$)alkyl; C1-C6 alkoxy; fluoro(C1-C6) alkoxy; (C1-C6 alkyl)NH—; (C1-C6 alkyl)$_2$N—; cyano; and SO$_2$—(C1-C6)alkyl;
R4 is hydrogen or halo;
R5 is hydrogen; and
(i) each of R2 and R3 is hydrogen; or (ii) R2 is hydrogen, and R3 is fluoro; or (iii) R2 is a substituent other than hydrogen, and R3 is hydrogen.

14. The compound or salt according to claim 1, wherein the compound or salt has formula (Ia):

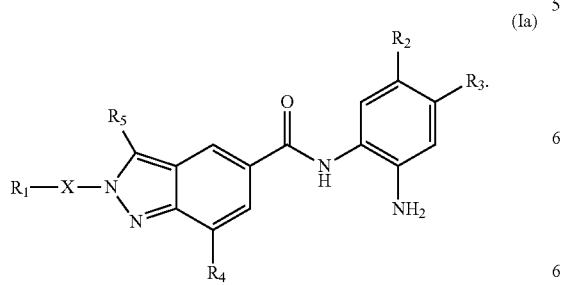

(Ia)

15. The compound or salt according to claim 1, wherein the compound or salt has formula (Ib):

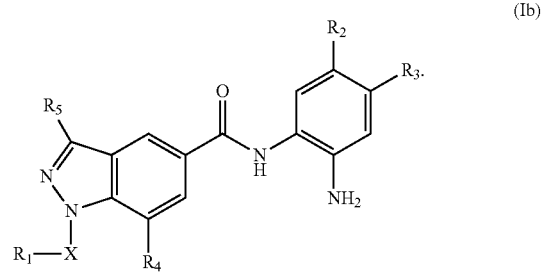

(Ib)

16. The compound or salt according to claim 9, wherein X is CH$_2$.

17. The compound or salt according to claim 9, wherein X is (CH$_2$)$_{2-4}$.

18. The compound or salt according to claim 9, wherein R1 is C3-C6 cycloalkyl, optionally substituted with from 1-3 R°.

19. The compound or salt according to claim 1, wherein the compound is selected from A1-A16.

20. The compound or salt according to claim 1, wherein —X—R$_1$ is CH$_2$phenyl, optionally substituted with one or more substituents selected from halo and methyl.

21. The compound or salt according to claim 1, wherein —XR$_1$, is CH$_2$pyridyl, optionally substituted with one or more substituents selected from halo and methyl.

22. The compound or salt according to claim 1, wherein —XR$_1$ is CH$_2$cyclopropyl, optionally substituted with one or more of C1-C3alkyl, C1-C3alkoxy, and halo.

23. The compound or salt according to claim 1, wherein —XR$_1$ is CH$_2$pyrazolyl, optionally substituted with one or more substituents selected from methyl and halo.

24. The compound or salt according to claim 1, wherein R$_2$ is hydrogen and R$_3$ is F or Cl.

25. A pharmaceutical composition comprising a compound, or pharmaceutically acceptable salt thereof, as claimed in claim 1 and a pharmaceutically acceptable carrier.

26. A method of inhibiting HDAC1, HDAC2, and HDAC3, the method comprising contacting a cell with an effective amount of a compound, or pharmaceutically acceptable salt thereof, as claimed in claim 1.

27. A method of treating Friedreich's ataxia in a patient in need thereof, the method comprising administering a compound, or pharmaceutically acceptable salt thereof, as claimed in claim 1 to said patient.

28. The compound or salt according to claim 1, wherein the compound or salt is selected from the group consisting of:

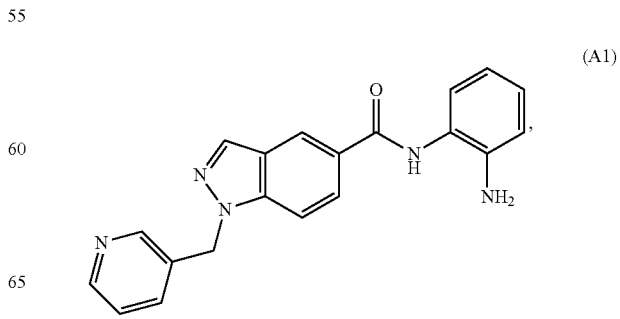

(A1)

-continued
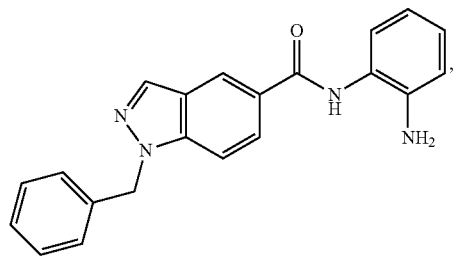
(A2)
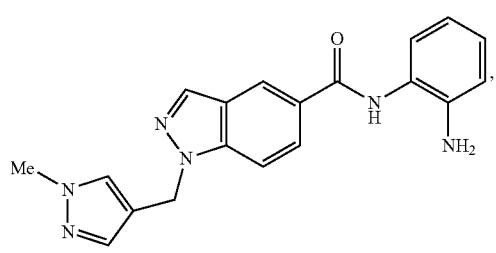
(A3)
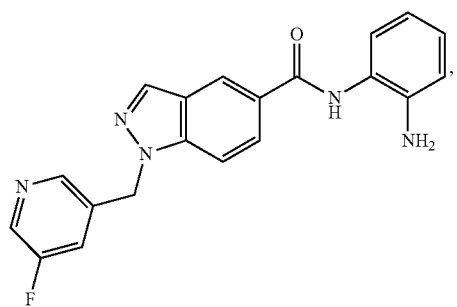
(A4)
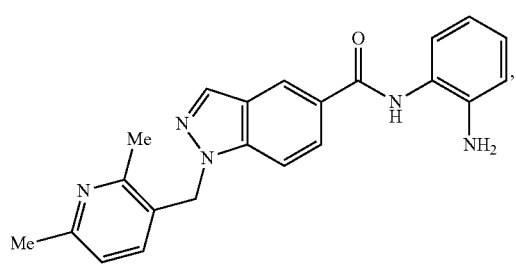
(A5)
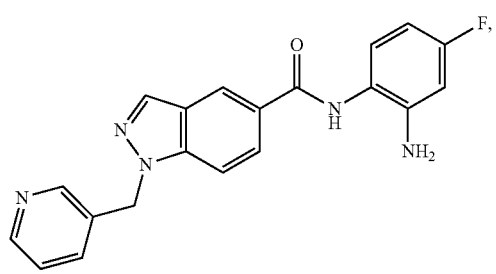
(A6)
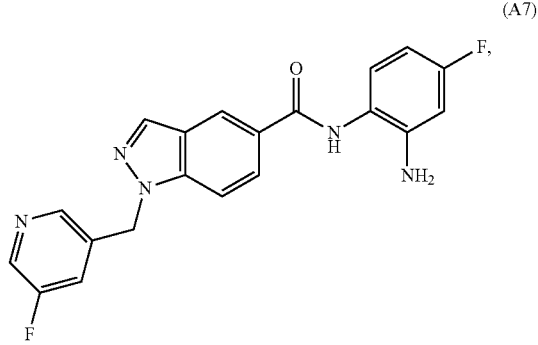
(A7)
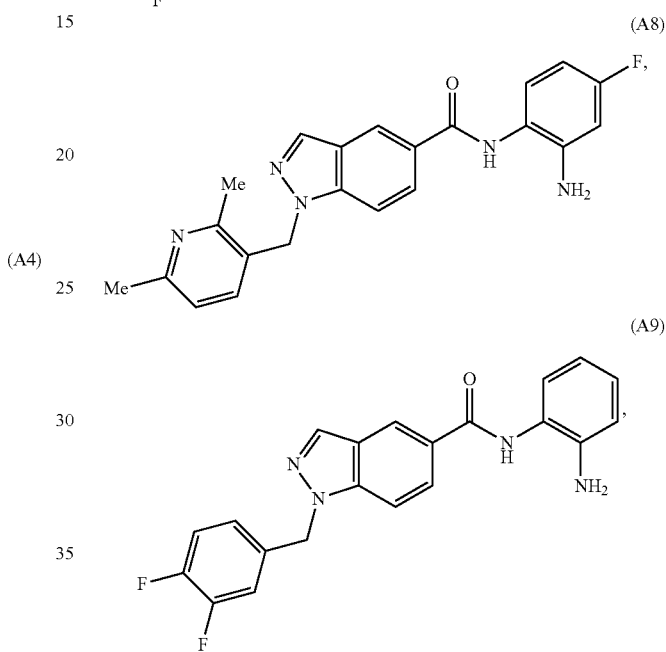
(A8)
(A9)
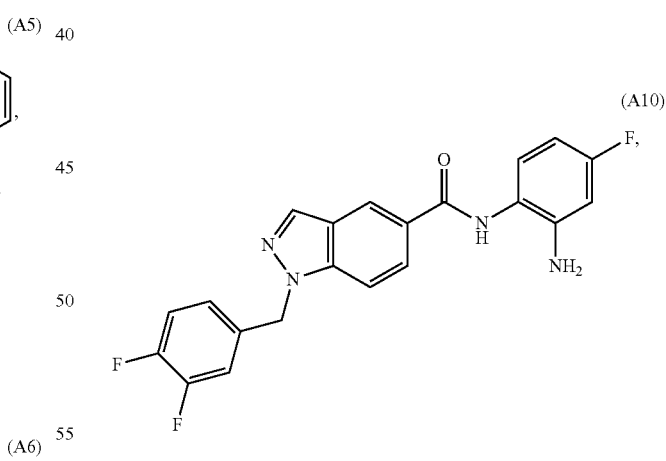
(A10)
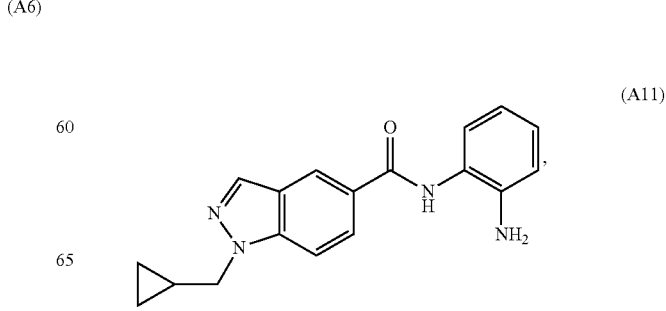
(A11)

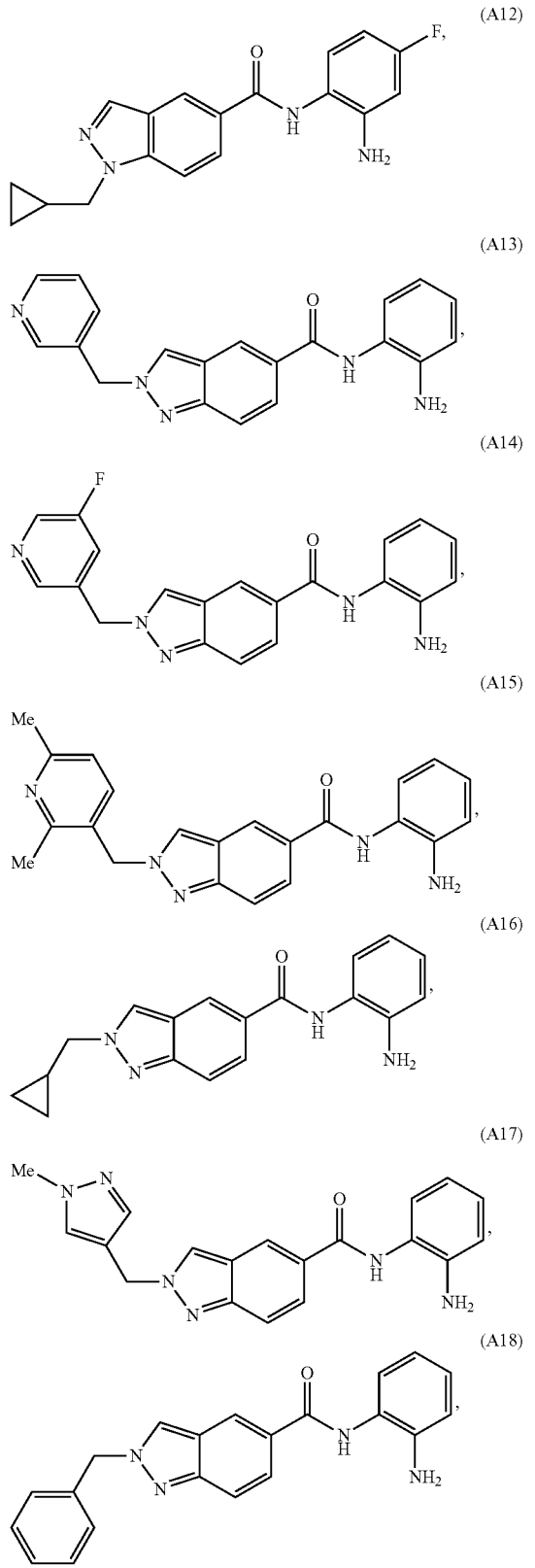
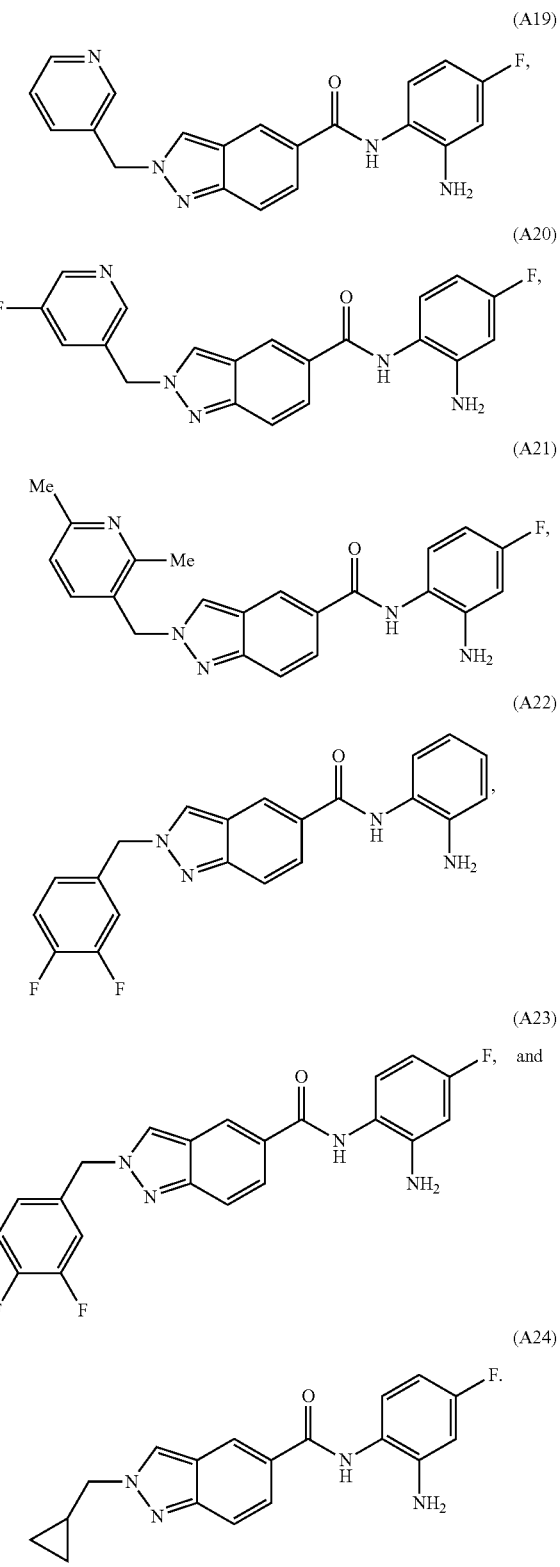

UNITED STATES PATENT AND TRADEMARK OFFICE
CERTIFICATE OF CORRECTION

PATENT NO. : 10,029,988 B2
APPLICATION NO. : 14/773472
DATED : July 24, 2018
INVENTOR(S) : Vincent Jacques et al.

It is certified that error appears in the above-identified patent and that said Letters Patent is hereby corrected as shown below:

In the Claims

At Column 64, Line 2, Claim 1 "$S(O)_m$," should be -- $S(O)_m$ --.

At Column 64, Line 15, Claim 1 "C1-6" should be -- C1-C6 --.

At Column 64, Line 17, Claim 1 "C1-6" should be -- C1-C6 --.

At Column 64, Line 24, Claim 1 "C1-6" should be -- C1-C6 --.

At Column 64, Line 34, Claim 1 "C1-6" should be -- C1-C6 --.

At Column 65, Line 2, Claim 1 "0, N," should be -- O, N, --.

At Column 65, Line 45, Claim 1 "C1-06" should be -- C1-C6 --.

At Column 65, Line 56, Claim 1 "H, F, CI," should be -- H, F, Cl, --.

At Column 66, Line 65, Claim 10 "C6alkyl), 0," should be -- C6 alkyl), O, --.

At Column 67, Line 15, Claim 11 "$SO_2$—(C1-C6)alkyl.;" should be -- $SO_2$—(C1-C6)alkyl; --.

At Column 68, Line 30, Claim 21 "—$XR_1$," should be -- —$XR_1$ --.

Signed and Sealed this
Nineteenth Day of February, 2019

Andrei Iancu
*Director of the United States Patent and Trademark Office*